(12) United States Patent
Rajendran et al.

(10) Patent No.: US 8,986,283 B2
(45) Date of Patent: Mar. 24, 2015

(54) CONTINUOUS ANESTHESIA NERVE CONDUCTION APPARATUS, SYSTEM AND METHOD THEREOF

(71) Applicant: Solodex LLC, Colorado Springs, CO (US)

(72) Inventors: Sundar Rajendran, Colorado Springs, CO (US); Dan Joel Kopacz, Colorado Springs, CO (US); Siddharth Desai, Ladera Ranch, CA (US)

(73) Assignee: Solo-Dex, LLC, Colorado Springs, CO (US)

( * ) Notice: Subject to any disclaimer, the term of this patent is extended or adjusted under 35 U.S.C. 154(b) by 0 days.

(21) Appl. No.: 14/035,940

(22) Filed: Sep. 24, 2013

(65) Prior Publication Data
US 2014/0025039 A1    Jan. 23, 2014

Related U.S. Application Data

(63) Continuation-in-part of application No. 14/006,962, filed as application No. PCT/US2012/038504 on May 18, 2012.

(60) Provisional application No. 61/724,539, filed on Nov. 9, 2012, provisional application No. 61/487,555, filed on May 18, 2011, provisional application No. 61/532,316, filed on Sep. 8, 2011.

(51) Int. Cl.
*A61M 31/00*     (2006.01)
*A61M 19/00*     (2006.01)
(Continued)

(52) U.S. Cl.
CPC ............ *A61M 19/00* (2013.01); *A61B 17/3401* (2013.01); *A61M 25/0606* (2013.01);
(Continued)

(58) Field of Classification Search
CPC ................... A61B 17/3401; A61B 2025/0008; A61N 1/36021; A61N 1/18; A61M 2025/09175
USPC ............... 604/512, 164.01, 500, 164.11, 264, 604/164.09, 170.02, 170.03
See application file for complete search history.

(56) References Cited

U.S. PATENT DOCUMENTS 4,515,168 A    5/1985   Chester et al.
4,615,472 A    10/1986  Nash
(Continued)

FOREIGN PATENT DOCUMENTS

EP        2091604         8/2009
WO    WO 2011/071892     6/2011

OTHER PUBLICATIONS

U.S. Appl. No. 14/321,793, filed Jul. 1, 2014, Rajendran et al.
(Continued)

*Primary Examiner* — Bhisma Mehta
*Assistant Examiner* — Hamza Darb
(74) *Attorney, Agent, or Firm* — Aspire IP; Scott J. Hawranek

(57) ABSTRACT

The invention generally relates to a continuous anesthesia nerve conduction apparatus and method thereof, and more particularly to a method and system for use in administering a continuous flow or intermittent bolus of anesthetic agent to facilitate a continuous or prolonged nerve block. In one embodiment, the apparatus includes a sheath having a proximal end, a distal end and at least one lumen extending from the proximal end to the distal end. The sheath also includes an embedded conductive element for transmitting an electrical signal from a proximal portion of the sheath to a distal portion of the sheath. A cannula is arranged in the at least one lumen of the sheath and has a distal end protruding from a distal portion of the sheath. The cannula is electrically coupled to at least a portion of the embedded conductive element and is configured to provide nerve stimulation.

29 Claims, 38 Drawing Sheets

(51) Int. Cl.
*A61B 17/34* (2006.01)
*A61M 25/06* (2006.01)
*A61N 1/36* (2006.01)
*A61M 5/142* (2006.01)
*A61M 25/00* (2006.01)
*A61M 25/01* (2006.01)
*A61M 25/09* (2006.01)
*A61N 1/05* (2006.01)

(52) U.S. Cl.
CPC ......... *A61B17/3415* (2013.01); *A61N 1/36021* (2013.01); *A61M 5/142* (2013.01); *A61M 25/0041* (2013.01); *A61M 25/0045* (2013.01); *A61M 25/0053* (2013.01); *A61M 25/00* (2013.01); *A61M 25/007* (2013.01); *A61M 25/0074* (2013.01); *A61M 25/0097* (2013.01); *A61M 25/0108* (2013.01); *A61M 25/0113* (2013.01); *A61M 25/065* (2013.01); *A61M 2025/0008* (2013.01); *A61M 2025/09175* (2013.01); *A61N 1/0551* (2013.01); *A61M 2202/048* (2013.01); *A61M 2205/0205* (2013.01); *A61M 2205/0233* (2013.01); *A61M 2205/054* (2013.01); *A61M 2205/10* (2013.01)
USPC .................. 604/512; 604/164.11; 604/164.01

(56) References Cited

U.S. PATENT DOCUMENTS

| | | | |
|---|---|---|---|
| 4,726,369 A | 2/1988 | Mar | |
| 4,775,367 A | 10/1988 | Schmidt | |
| 4,828,549 A | 5/1989 | Kvalo | |
| 4,840,184 A | 6/1989 | Garg | |
| 4,889,529 A | 12/1989 | Haindl | |
| 4,957,117 A | 9/1990 | Wysham | |
| 5,080,652 A | 1/1992 | Sancoff et al. | |
| 5,100,390 A | 3/1992 | Lubeck et al. | |
| 5,105,983 A | 4/1992 | Sancoff et al. | |
| 5,108,380 A | 4/1992 | Herlitze et al. | |
| 5,149,327 A | 9/1992 | Oshiyama | |
| 5,158,544 A | 10/1992 | Weinstein | |
| 5,279,563 A | 1/1994 | Brucker et al. | |
| 5,284,481 A | 2/1994 | Soika et al. | |
| 5,325,746 A | 7/1994 | Anderson | |
| 5,325,868 A | 7/1994 | Kimmelstiel | |
| 5,352,201 A | 10/1994 | Jemmott | |
| 5,364,373 A | 11/1994 | Waskonig et al. | |
| 5,405,334 A | 4/1995 | Roth et al. | |
| 5,405,344 A | 4/1995 | Williamson et al. | |
| 5,423,331 A | 6/1995 | Wysham | |
| 5,505,714 A | 4/1996 | Dassa et al. | |
| 5,512,052 A | 4/1996 | Jesch | |
| 5,558,652 A | 9/1996 | Henke | |
| 5,618,268 A | 4/1997 | Raines et al. | |
| 5,630,802 A | 5/1997 | Moellmann et al. | |
| 5,634,475 A | 6/1997 | Wolvek | |
| 5,695,470 A | 12/1997 | Roussigne et al. | |
| 5,697,904 A | 12/1997 | Raines et al. | |
| 5,730,150 A | 3/1998 | Peppel et al. | |
| 5,817,017 A | 10/1998 | Young et al. | |
| 5,843,048 A | 12/1998 | Gross | |
| 5,858,002 A | 1/1999 | Jesch | |
| 5,871,470 A | 2/1999 | McWha | |
| 5,899,891 A | 5/1999 | Racz | |
| 5,910,132 A | 6/1999 | Schultz | |
| 5,932,778 A | 8/1999 | Valente et al. | |
| 5,976,110 A | 11/1999 | Greengrass et al. | |
| 6,030,349 A | 2/2000 | Wilson et al. | |
| 6,117,115 A | 9/2000 | Hill et al. | |
| 6,165,164 A | 12/2000 | Hill et al. | |
| 6,179,816 B1 | 1/2001 | Mottola et al. | |
| 6,221,064 B1 | 4/2001 | Nadal | |
| 6,248,116 B1 | 6/2001 | Chevillon et al. | |
| 6,287,278 B1 | 9/2001 | Woehr et al. | |
| 6,342,059 B1 | 1/2002 | Chevillon et al. | |
| 6,428,514 B1 | 8/2002 | Goebel et al. | |
| 6,456,874 B1 | 9/2002 | Hafer et al. | |
| 6,511,506 B2 | 1/2003 | Chevillon et al. | |
| 6,585,704 B2 | 7/2003 | Luther et al. | |
| 6,613,014 B1 | 9/2003 | Chi | |
| 6,616,630 B1 | 9/2003 | Woehr et al. | |
| 6,626,885 B2 | 9/2003 | Massengale | |
| 6,635,033 B1 | 10/2003 | Hill et al. | |
| 6,709,419 B2 | 3/2004 | Woehr | |
| 6,730,083 B2 | 5/2004 | Freigang et al. | |
| 6,949,104 B2 | 9/2005 | Griffis et al. | |
| 6,973,346 B2 * | 12/2005 | Hafer et al. | 604/21 |
| 7,004,923 B2 | 2/2006 | Deniega et al. | |
| 7,027,873 B2 | 4/2006 | Pajunk et al. | |
| 7,120,487 B2 | 10/2006 | Nelson | |
| 7,125,397 B2 | 10/2006 | Woehr et al. | |
| 7,160,269 B2 | 1/2007 | Woehr | |
| 7,186,239 B2 | 3/2007 | Woehr | |
| 7,264,613 B2 | 9/2007 | Woehr et al. | |
| 7,322,961 B2 | 1/2008 | Forrest | |
| 7,322,962 B2 | 1/2008 | Forrest | |
| 7,374,554 B2 | 5/2008 | Menzi et al. | |
| 7,445,614 B2 | 11/2008 | Bunodiere et al. | |
| 7,465,291 B2 | 12/2008 | Massengale | |
| 7,500,965 B2 | 3/2009 | Menzi et al. | |
| 7,510,077 B2 | 3/2009 | Massengale et al. | |
| 7,524,305 B2 | 4/2009 | Moyer | |
| 7,596,045 B2 | 9/2009 | DeBrosse et al. | |
| 7,608,057 B2 | 10/2009 | Woehr et al. | |
| 7,611,487 B2 | 11/2009 | Woehr et al. | |
| 7,611,499 B2 | 11/2009 | Woehr et al. | |
| 7,625,360 B2 | 12/2009 | Woehr et al. | |
| 7,651,476 B2 | 1/2010 | Kohler | |
| 7,699,809 B2 | 4/2010 | Urmey | |
| 7,731,687 B2 | 6/2010 | Menzi et al. | |
| 7,806,849 B2 | 10/2010 | Woehr | |
| 7,815,604 B2 | 10/2010 | Massengale et al. | |
| 7,854,730 B2 | 12/2010 | Dal Porto et al. | |
| 7,887,733 B2 | 2/2011 | Moyer | |
| 7,905,862 B2 * | 3/2011 | Sampson | 604/164.01 |
| 7,959,623 B2 | 6/2011 | Massengale | |
| 7,972,313 B2 | 7/2011 | Woehr et al. | |
| 8,215,157 B2 | 7/2012 | Wang et al. | |
| 8,231,588 B2 | 7/2012 | Xia | |
| 8,287,496 B2 | 10/2012 | Racz | |
| 8,298,208 B2 | 10/2012 | Racz | |
| 2001/0016702 A1 | 8/2001 | Benjamin | |
| 2001/0017807 A1 | 8/2001 | Fujioka | |
| 2001/0032003 A1 | 10/2001 | Pecor | |
| 2002/0019608 A1 * | 2/2002 | Mason et al. | 604/133 |
| 2002/0022891 A1 | 2/2002 | Chevillon et al. | |
| 2002/0026209 A1 | 2/2002 | Hung | |
| 2002/0082583 A1 | 6/2002 | Lerner | |
| 2002/0188346 A1 | 12/2002 | Healy et al. | |
| 2003/0093104 A1 | 5/2003 | Bonner et al. | |
| 2003/0176888 A1 | 9/2003 | O'Connell | |
| 2004/0047807 A1 | 3/2004 | Meyer | |
| 2004/0049157 A1 * | 3/2004 | Plishka et al. | 604/164.09 |
| 2004/0059247 A1 | 3/2004 | Urmey | |
| 2004/0158210 A1 | 8/2004 | Staunton et al. | |
| 2004/0162522 A1 | 8/2004 | Woehr | |
| 2004/0181206 A1 | 9/2004 | Chiu et al. | |
| 2005/0020965 A1 | 1/2005 | Rioux et al. | |
| 2005/0043690 A1 | 2/2005 | Todd | |
| 2005/0043709 A1 | 2/2005 | Brimhall et al. | |
| 2005/0171478 A1 | 8/2005 | Selmon et al. | |
| 2005/0192638 A1 | 9/2005 | Gelfand et al. | |
| 2005/0245874 A1 * | 11/2005 | Carrez et al. | 604/160 |
| 2005/0257751 A1 | 11/2005 | Jackson et al. | |
| 2005/0277910 A1 | 12/2005 | Dolla et al. | |
| 2005/0283111 A1 | 12/2005 | Maurice | |
| 2006/0015068 A1 | 1/2006 | Amisar et al. | |
| 2006/0106367 A1 | 5/2006 | Massengale et al. | |
| 2006/0116638 A1 | 6/2006 | Woehr et al. | |
| 2006/0184125 A1 | 8/2006 | Woehr | |
| 2006/0206055 A1 | 9/2006 | Ice | |
| 2006/0217655 A1 | 9/2006 | Vitullo et al. | |
| 2006/0267063 A1 | 11/2006 | McDaniel | |

(56) References Cited

U.S. PATENT DOCUMENTS

| | | |
|---|---|---|
| 2006/0270980 A1 | 11/2006 | Menzi et al. |
| 2007/0088382 A1 | 4/2007 | Bei et al. |
| 2007/0100297 A1 | 5/2007 | Woehr et al. |
| 2007/0129689 A1 | 6/2007 | Woehr et al. |
| 2007/0156093 A1 | 7/2007 | Woehr |
| 2008/0021435 A1 | 1/2008 | Miller et al. |
| 2008/0045927 A1 | 2/2008 | Goebel et al. |
| 2008/0045932 A1 | 2/2008 | Beau et al. |
| 2008/0058702 A1 | 3/2008 | Arndt et al. |
| 2008/0065029 A1 | 3/2008 | Racz |
| 2008/0097317 A1 | 4/2008 | Alholm et al. |
| 2008/0172039 A1 | 7/2008 | Raines |
| 2008/0228133 A1 | 9/2008 | Hildebrand et al. |
| 2009/0000970 A1 | 1/2009 | Bordeau et al. |
| 2009/0054837 A1 | 2/2009 | Von Holst et al. |
| 2009/0105693 A1 | 4/2009 | Ben-David et al. |
| 2009/0218728 A1 | 9/2009 | Moyer |
| 2009/0259126 A1 | 10/2009 | Saal et al. |
| 2009/0326512 A1 | 12/2009 | Appling et al. |
| 2010/0003282 A1 | 1/2010 | Deem et al. |
| 2010/0010038 A1 | 1/2010 | Uchikawa et al. |
| 2010/0049171 A1 | 2/2010 | McQueen et al. |
| 2010/0087770 A1 | 4/2010 | Bock et al. |
| 2010/0130923 A1 | 5/2010 | Cleary et al. |
| 2010/0210997 A1 | 8/2010 | Gharib |
| 2010/0286657 A1 * | 11/2010 | Heck .......................... 604/508 |
| 2011/0034790 A1 | 2/2011 | Mourlas et al. |
| 2011/0054383 A1 | 3/2011 | Boezaart |
| 2011/0071480 A1 | 3/2011 | Katerkamp et al. |
| 2011/0106133 A1 | 5/2011 | O'Connell et al. |
| 2011/0112511 A1 | 5/2011 | Singer |
| 2011/0166526 A1 | 7/2011 | Kuracina et al. |
| 2011/0201930 A1 | 8/2011 | Guzman |
| 2011/0218518 A1 | 9/2011 | Eichmann et al. |
| 2012/0059308 A1 | 3/2012 | Hsu et al. |
| 2012/0078175 A1 | 3/2012 | Vreeman |
| 2012/0232389 A1 | 9/2012 | Guzman |
| 2013/0084319 A1 | 4/2013 | Priewe et al. |
| 2013/0096505 A1 | 4/2013 | Urmey |
| 2014/0073926 A1 | 3/2014 | Rajendran et al. |

OTHER PUBLICATIONS

U.S. Appl. No. 14/321,795, filed Jul. 1, 2014, Rajendran et al.

"Contiplex C: As Simple as a Single Shote with the Power of a Catheter," available at http://www.bbraun.com/cps/rde/xchg/bbraun-com/hs.xsl/13128.html, 2 pages, Sep. 21, 2014.

International Search Report for International (PCT) Application No. PCT/US13/61507 mailed Feb. 24, 2014, 6 pages.

Written Opinion for International (PCT) Application No. PCT/US13/61507 mailed Feb. 24, 2014, 15 pages.

International Search Report and Written Opinion for International (PCT) Application No. PCT/US12/38504 mailed Feb. Sep. 6, 2012, 21 pages.

Extended European Search Report for European Application No. 12786621.8 dated Jan. 9, 2015, 5 pages.

\* cited by examiner

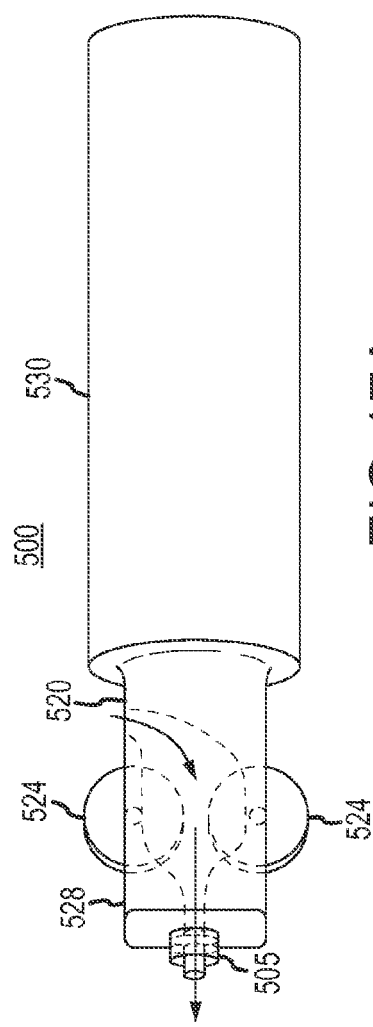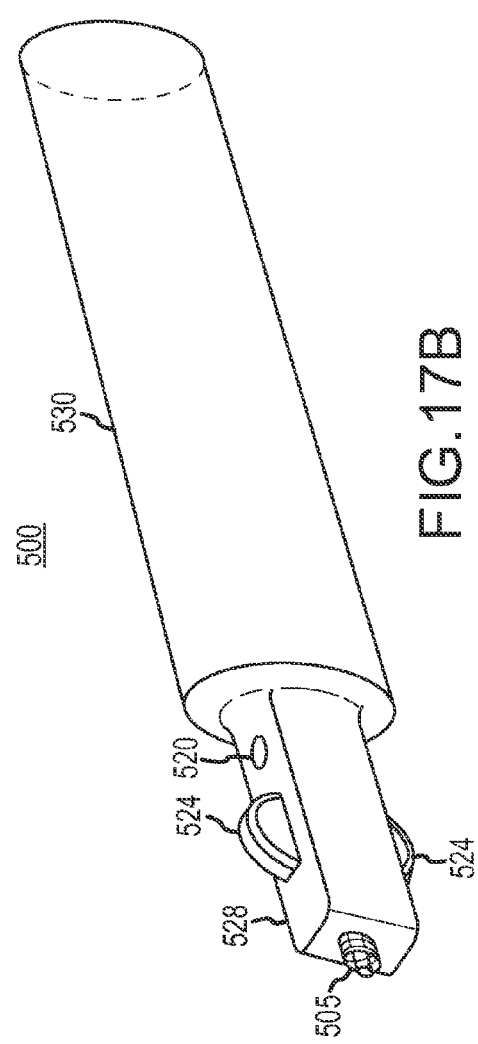

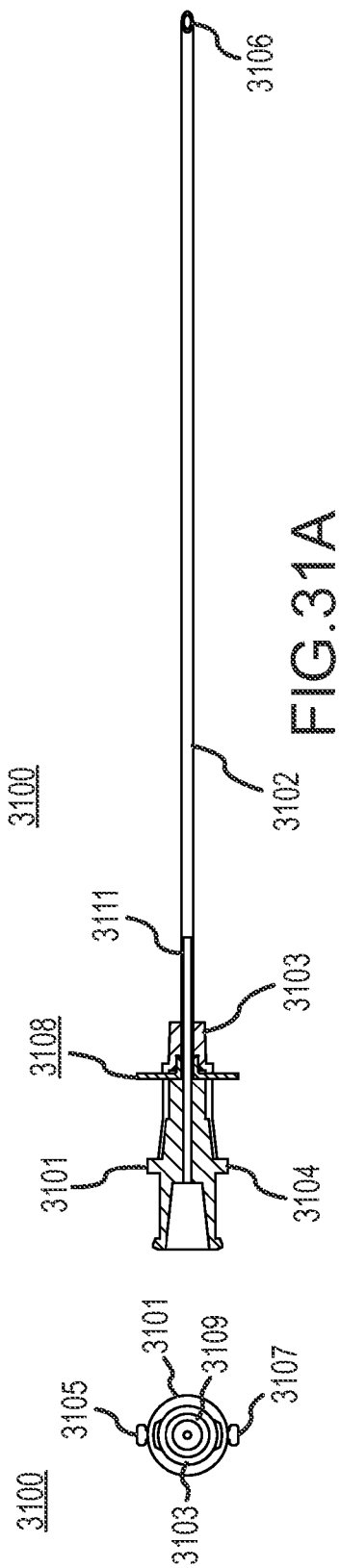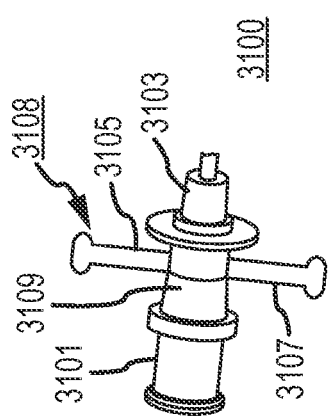
FIG.31A
FIG.31B
FIG.31C

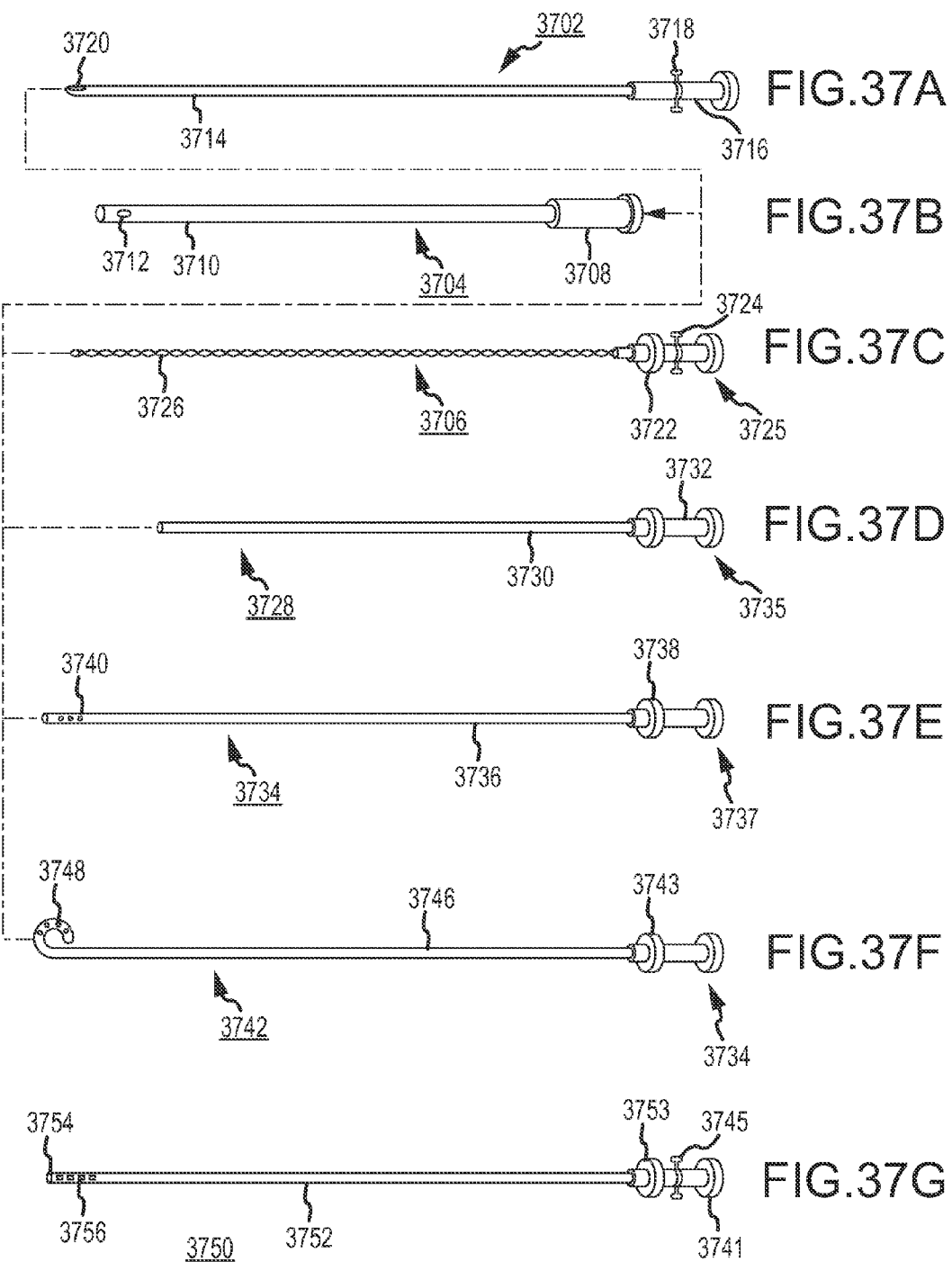

CONTINUOUS ANESTHESIA NERVE CONDUCTION APPARATUS, SYSTEM AND METHOD THEREOF

This application is a continuation-in-part of U.S. patent application Ser. No. 14/006,962, filed on Sep. 23, 2013, and also claims the benefit under 35 U.S.C. §119(e) of U.S. Provisional Patent Application No. 61/724,539, filed on Nov. 9, 2012; U.S. patent application Ser. No. 14/006,962 is the National Stage of International Application No. PCT/US2012/038504, filed May 18, 2012, which claims the benefit under 35 U.S.C. §119(e) of U.S. Provisional Patent Application No. 61/487,555, filed on May 18, 2011, and U.S. Provisional Patent Application No. 61/532,316, filed on Sep. 8, 2011; each of these applications are hereby incorporated by reference for all purposes as if fully set forth herein.

BACKGROUND OF THE INVENTION

1. Field of the Invention

The invention generally relates to a continuous anesthesia nerve conduction apparatus, system and method thereof, and more particularly to a method and system for use in administering a continuous flow or intermittent bolus of anesthetic agent to facilitate a continuous or prolonged nerve block.

2. Discussion of the Related Art

Currently, regional anesthesia techniques have been employed to selectively anesthetize a nerve or groups of nerves to provide pain relief to patients following a medical-surgical procedure or trauma. Anesthetic agents, such as local anesthetic medication, are administered in close proximity to nerve(s) that innervate the affected region of the body. These nerves are located deep within the tissues and a hollow bore hypodermic needle is used to deliver the anesthetic medication to the nerve(s).

In continuous regional anesthetic procedures, in lieu of a needle, a catheter and needle are inserted adjacent to the nerve(s). The needle is removed after the catheter placement, and the catheter may be left in position for several days so that anesthetic medication can be repeatedly or continuously delivered to the targeted nerve(s). These nerve blocks are only efficacious if the anesthetic medication can be delivered consistently in close enough proximity to the nerve(s) so as to impart its action on the nerve(s).

U.S. Pat. No. 5,976,110 discloses an epidural needle that can be coupled to a nerve stimulator. The nerve stimulator is configured to provide an electrical current that activates the targeted nerve(s) as the needle gets into close proximity of the nerve(s). An epidural catheter is inserted through the lumen of the epidural needle and advanced until the distal tip extends several centimeters past the distal tip of the needle. The epidural catheter is placed without any visualization aid and is assumed to be in close enough proximity to the targeted nerve due to the needle tip position.

U.S. Pat. No. 6,456,874 discloses an epidural catheter configured to emit an electrical impulse. Placement of the catheter tip and confirmation of the catheter tip placement is obtained by stimulating the targeted nerve(s) via the nerve stimulator.

In addition to the use of peripheral nerve stimulation for nerve localization, ultrasound imaging has become a common method to position needles and catheters in close proximity to nerve(s).

The related art has a number of disadvantages. The ultrasound probe is best managed by the operator of the needle and/or catheter. As such, to maintain real-time imaging, one of the operator's hands needs to be occupied handling the ultrasound transducer. However, the procedure is difficult with the related art devices as both hands are required for advancing a catheter through the needle. Therefore, during this procedure the ultrasound probe must be put down and the visualization at that point is lost.

Alternatively, another clinician is required or some sort of mechanical holding means may be utilized. These alternatives both have disadvantages. The ultrasound image is a two-dimensional image with an image plane of typically less than one millimeter. The mechanical holding devices, i.e., an articulating probe holder often is not effective because patient movement can cause the image to distort or deviate, thereby preventing reliable real-time imaging of the catheter exiting the needle and also preventing visual confirmation of the position of the catheter tip. Moreover, the related art catheter devices frequently employ Touhy tipped needles that tend to cause the catheter to curve away from the tip of the needle and out of the two-dimensional visualization plane as the catheter exits the needle. Therefore, images of the needle with the catheter exiting the needle are not typically obtained and the relationship to the targeted nerve(s) is not conclusively obtained.

Another disadvantage of the related art is the need for two hands to manage the catheter advancement, as both hands require sterile gloves and sterile procedural adherence. Thus, the ultrasound device will need to be sterile, which requires additional setup such as sterile sleeves for the ultrasound probe, sterile ultrasound gel, extensive draping, and additional personnel. This additional setup adds to the complexity, inefficiency, timeliness, and cost of clinicians performing this technique.

The related art catheters themselves also have disadvantages. For example, in order for the needle to be withdrawn while trying to maintain the catheter in place, the catheter needs to be about twice the length of the needle. This added length makes the catheter unwieldy, expensive, and difficult to use. The catheter also requires a lubricious exterior so that it will easily slide through the needle. The lubricious exterior of the catheter makes it difficult to adhere to the skin of the patient, which leads to easy dislodgement from its position adjacent to the nerve(s).

In addition, passing the catheter through the lumen of a large bore needle, the catheter's diameter is such that it is smaller than that of the puncture made by the needle through the tissue. The catheter diameter size being smaller than the needle can lead to leakage of medication at the insertion site during medication infusion, increasing the chance of catheter dislodgement.

There is a need for an improved continuous anesthesia nerve conduction apparatus, system and method that substantially obviates one or more of the problems due to limitations and disadvantages of the related art.

SUMMARY OF THE INVENTION

Accordingly, the invention is directed to continuous anesthesia nerve conduction apparatus, system and method that substantially obviates one or more of the problems due to limitations and disadvantages of the related art.

An advantage of the invention is that the procedure may be performed by one proficient in the art in approximately the same time or less than it takes to perform a single-injection nerve block with a needle alone. In most cases, the procedure may be performed in less than approximately ten minutes.

Another advantage of the invention is that the procedure does not require a full sterile setup, thereby reducing the time of the procedure.

Still another advantage of the invention is to provide an apparatus and method for performing continuous nerve blocks under real-time ultrasound guidance that may be performed with a single hand by one operator.

Yet another advantage of the invention is to provide an apparatus and method that allows for easy handling with secure fixation to prevent dislodgement and minimize leakage during infusion.

Still yet another advantage is to provide an apparatus and method that allows for a single operator to easily and efficiently place a continuous nerve conduction catheter while simultaneously visualizing the catheter placement under ultrasound guidance, e.g., with markings or markers as described herein.

Still another advantage is to provide an apparatus and method that allows for peripheral nerve stimulation capability to be performed simultaneously with visualization and with one handed operation.

Another advantage is to provide peripheral nerve stimulation emitting from a needle and/or the catheter. The catheter stimulation may be used for secondary confirmation, if needed. The nerve stimulation can also be utilized via a single electrical connection at or near a hub of the catheter.

Still another advantage is to provide an apparatus and method that permits a fast, cost efficient, and minor labor intensive process, thereby making continuous nerve conduction pain relief accessible for more patients.

Yet another advantage is to provide a catheter with a lateral port configured to minimize occlusion rate when compared to a catheter with only a distal opening.

Still another advantage is to provide a catheter with a preformed resilient distal portion to allow the distal portion of the catheter to be positioned at least partially around a nerve, thereby permitting delivery of a pharmacological agent more effectively around the entire nerve as compared to infusion from a straight catheter that is positioned at a single point. In a preferred embodiment, at least one lateral port is positioned near or on an apex of a curved portion of the catheter.

Yet another advantage is to provide a catheter with a thickened or roughened proximal segment of catheter, thereby minimizing leakage of infused medication by wedging the catheter into the skin opening at the insertion site. Leakage of medication tends to loosen the dressing and increase the chance of accidental dislodgement.

Still yet another advantage is to stimulate a needle while using the catheter as the insulator. This permits a single attachment point for the nerve stimulator while reducing procedural steps and also simplifies manufacturing by eliminating the redundant insulating coating for the stimulating needle.

Yet still another advantage is to provide a guidewire for catheter positioning. The guidewire may include a pre-shaped distal tip configure to allow a catheter to track this geometry. Typically, a catheter does not readily move into the predetermined position because of a lack of space caused by tissue surrounding the nerve(s) and utilizing a guidewire can eliminate this problem. In addition, a directional guidewire may be utilized. The directional guidewire is known in the art and may be smaller and stiffer which permits easier positioning around the nerve(s) in a curved orientation and would then allow for the catheter to follow the tract of the guidewire. Moreover, an integrated guidewire with a needle may be utilized. This type of configuration allows for single handed deployment of guidewire by advancing the tab on the needle hub, also reducing procedural steps by not having to detach the syringe before advancing guidewire. This can also be a methodology differentiation.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof, as well as the appended drawings.

To achieve these and other advantages and in accordance with the purpose of the present invention, as embodied and broadly described, the apparatus includes a sheath, also referred to as a catheter having a proximal end, a distal end and at least one lumen extending from the proximal end to the distal end. In one embodiment, the sheath can include an embedded conductive element, e.g., wire, for transmitting an electrical signal from a proximal portion of the sheath to a distal portion of the sheath. A cannula, e.g., needle or introducer, is arranged in at least one lumen of the sheath and sized such that a distal end portion extends past a distal end portion of the sheath. The cannula can be electrically coupled to at least a portion of the embedded conductive element and is configured to provide nerve stimulation.

In another aspect of the invention, a method for administering a continuous flow or intermittent bolus of anesthetic agent to facilitate a continuous or prolonged nerve block includes providing a sheath having a lumen extending from a proximal end to a distal end. The sheath includes an embedded conductive element for transmitting an electrical signal from a proximal portion of the sheath to a distal portion of the sheath. In another embodiment, the sheath provides for insulation of the electrical signal along the shaft of the cannula.

The method further includes providing a cannula into at least one lumen of the sheath. The method further includes connecting a syringe configured to administer a pharmacological agent to the proximal end of the cannula and coupling an electrical signal generator to the embedded conductive element or the proximal portion of the needle. Next, the cannula and sheath are inserted simultaneously into the patient as a single unit. The method includes locating at least one nerve of the patient with at least one of an electric signal generated from the electrical signal generator and/or an active imaging device. Next, upon location of the nerve, a pharmacological agent is administered to the nerve after which advancing and positioning the sheath off of the cannula with a single hand of a single user. If necessary, a guidewire can be deployed to direct the catheter into a curved position around the nerve(s). Alternatively, the catheter has a preformed memory shape and upon removal of the cannula, the sheath curves to the preformed memory shape.

Yet another embodiment of the invention is directed towards a kit, e.g., a medical package. The kit includes an apparatus for administering a continuous flow or intermittent bolus of anesthetic agent to facilitate a continuous or prolonged nerve block and directions for use. The kit may also optionally include a pump for administering a pharmacological agent, e.g., a disposable infusion pump.

Yet another embodiment of the invention is directed towards a kit, wherein the kit includes sterilized and recycled apparatuses, such as a recycled pump, e.g., infusion pump.

Yet another embodiment of the invention is directed to a method of introducing fluid to a nerve or nerve bundle of a patient. The method includes the steps of providing an introducer through a lumen of the catheter such that the introducer protrudes out the distal tip of the catheter. The method also includes piercing the skin of the patient with the introducer and catheter and advancing the introducer and catheter through the patient's tissue to a nerve bundle. Upon location of the nerve via imaging and/or electrical stimulation removing the introducer from the catheter. The distal end portion of the catheter is now located in proximity of the nerve bundle and fluid is introduced to the nerve bundle through the catheter, e.g., a nerve block.

Yet another embodiment of the invention is directed to a system for delivery of a fluid to a nerve bundle of a patient. The system includes a fluid pump, a length of tubing securable to said pump, an introducer, and a catheter. The introducer fits within the catheter. The catheter, pump, tubing, and introducer are provided together as a kit. Each component of the kit is sterilized.

Yet another embodiment of the invention is directed to a device for dispensing fluid to a patient. The device includes a catheter and an introducer. The introducer fits within a lumen of the catheter and is utilized as a system for insertion into the patient. The catheter is configured to be connected to a pump. The pump is compact and portable and configured for dispensing a liquid under pressure at a substantially constant flow rate.

In one embodiment, the pump includes an elongated, substantially cylindrical support member, an elongated elastic sleeve device mounted on and sealingly secured at fixed spaced longitudinal positions on said support member for defining a pressure reservoir for holding a liquid in a pressurized state for dispensing therefrom. The pump also includes a substantially spherical rigid housing formed of like half-shells hinged together for removably containing a support member and a pressure reservoir for enabling said pressure reservoir to expand naturally and for confining said reservoir to fill concentrically about said support member. The pump includes an inlet device for introducing a liquid into said elastic pressure reservoir and an outlet device for dispensing liquid from said pressure reservoir to a selected site.

It is to be understood that both the foregoing general description and the following detailed description are exemplary and explanatory, and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings:

FIG. 17A illustrates a single handed catheter advancing device according to another embodiment;

FIG. 17B illustrates a perspective view of the single handed catheter advancing device of FIG. 17A;

FIG. 31A illustrates a cross-sectional view of a cannula according to another embodiment of the invention;

FIG. 31B illustrates a proximal end view of the cannula of FIG. 31A;

FIG. 31C illustrates an exploded view of a hub portion of the cannula of FIG. 31A;

FIG. 37A illustrates a perspective view of a continuous anesthesia nerve conduction apparatus according to another embodiment of the invention;

FIG. 37B illustrates a catheter according to another embodiment of the invention;

FIG. 37C illustrates an anti-restriction member according to another embodiment of the invention;

FIG. 37D illustrates a catheter according to another embodiment of the invention;

FIG. 37E illustrates a catheter according to another embodiment of the invention;

FIG. 37F illustrates a catheter according to another embodiment of the invention;

FIG. 37G illustrates a catheter according to another embodiment of the invention;

DETAILED DESCRIPTION OF THE ILLUSTRATED EMBODIMENTS

Figure 1:
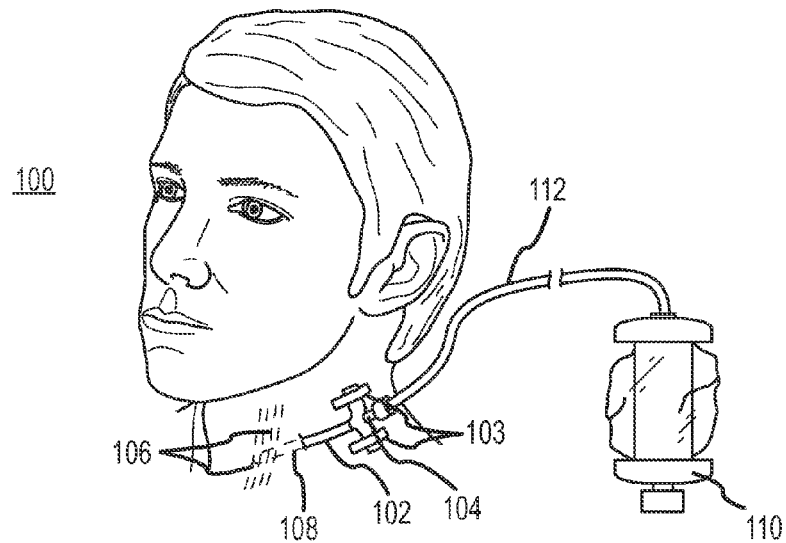
FIG. 1 illustrates an operational systematic view of a continuous anesthesia nerve conduction system according to an embodiment of the invention.

For the purposes of promoting an understanding of the principles of the present disclosure, reference will now be made to the exemplary embodiments illustrated in the drawing(s), and specific language will be used to describe the same.

Appearances of the phrases an "embodiment," an "example," or similar language in this specification may, but do not necessarily, refer to the same embodiment, to different embodiments, or to one or more of the figures. The features, functions, and the like described herein are considered to be able to be combined in whole or in part with one another as the claims and/or art may direct, either directly or indirectly, implicitly or explicitly.

As used herein, "comprising," "including," "containing," "is," "are," "characterized by," and grammatical equivalents thereof are inclusive or open-ended terms that do not exclude additional unrecited elements or method steps unless explicitly stated otherwise.

In order to more fully appreciate the present disclosure and to provide additional related features, the following references are incorporated herein by reference in their entireties:

(1) U.S. Pat. No. 5,100,390 by Lubeck, et al., which discloses a needle hereafter referred to as a metal cannula is of thin-walled construction and designed with a solid noncutting pencil point possessing a tip with an elliptical side port located not more than 1 (one) cannula Outer Diameter (O.D.) length from the tip. Via a hollow internal channel the axial length of the cannula is capable of guiding an inserted catheter through the cannula for projection laterally out of the cannula for subsequent indwelling placement of the introduced catheter upon removal of the cannula. The sideport is placed on the angled surface of the developing point so that it coincides with the angle of the pencil point. The elliptical sideport has a machined and polished rounded internal edge intersecting with the external surface. The construction of the cannula combining a large diameter with a pencil point and the location of an opening at the tip permits safe introduction of a spinal catheter into the subarachnoid space with minimum damage to tissues or membranes by either the cannula or a catheter exiting the sideport. The cannula is fitted with an obturator which coincides with the shape of the internal lumen of the cannula where the obturator tip curves upward to occlude the opening of the cannula sideport. The cannula of the present invention has application to subarachnoid and epidural regional anesthesia and pain management procedures. The present invention is designed preferably as a large gauge needle (17 to 21 gauge) so that it will accept insertion of a large flexible catheter (20 to 22 gauge in diameter) for indwelling placement.

(2) U.S. Pat. No. 5,364,373 by Waskonig, et al., which discloses an epidural cannula for local anesthesia having a cannula point with an adjacent lateral opening parallel to the longitudinal axis of the cannula. The cannula has a cross-sectional enlargement spaced from the point and having an area directed toward the point that forms an angle greater than 30 degrees relative to the longitudinal axis of the cannula.

(3) U.S. Pat. No. 5,817,017 by Young, et al., which discloses catheters and other medical devices include a non-metallic member having paramagnetic ionic particles fixedly incorporated therethrough in order to provide enhanced detectability when viewed by magnetic imaging regardless of the orientation of the non-metallic member in the magnetic field. Catheters are usually formed from polymeric tubing, and the paramagnetic ionic particles are usually formed from paramagnetic ions incorporated with water or other proton-donating fluid into carrier particles, such as zeolites, molecular sieves, clays, synthetic ion exchange resins, and microcapsules. Catheters and other medical devices include a non-metallic member having small iron and/or superparamagnetic particles fixedly incorporated therethrough or thereover in order to provide enhanced detectability when viewed by magnetic imaging. Catheters are usually formed from polymeric tubing, and the iron and/or superparamagnetic particles at or near the surface of the catheter interact with the water protons of the surrounding patient's body to provide image enhancement regardless of the orientation of the polymeric or other non-metallic material in the magnetic field.

(4) U.S. Pat. No. 5,843,048 by Gross which discloses an epidural needle through which an epidural catheter may be threaded for administering liquid anesthesia into the epidural space, the needle having a curved distal end, the tip of the needle distal to the opening in the needle shaft being substantially planar at an angle of 80.degree.-100.degree. relative to the curved longitudinal axis of the needle shaft, the needle tip being characterized as being faceted so as to retard inadvertent passage of the needle tip through the dura mater of a patient while at the same time retaining the sharp cutting edges common to a like epidural needle which has not had its tip so treated.

(5) U.S. Pat. No. 5,871,470 by McWha which discloses a combined spinal epidural needle set including an epidural needle with an overall length, an open distal end and a proximal end with a hub. The epidural needle has a hollow bore therethrough having an inside diameter. The set of the invention includes a spinal needle with an overall length greater than the length of the epidural needle, a pointed distal end, a proximal end with a hub and a hollow passage therethrough. The spinal needle has an outside diameter less than the inside diameter of the bore of the epidural needle. The spinal needle is slidably disposed for movement within the epidural needle between a position wherein the distal point of the spinal needle is substantially coincident with the open distal end of the epidural needle and at least one position wherein the distal point of the spinal needle projects beyond the open distal end of the epidural needle. The hubs of the epidural needle and the spinal needle each include an adjustable engagement for preselecting the position of the distal point of the spinal needle with respect to the open distal end of the epidural needle.

(6) U.S. Pat. No. 8,298,208 by Racz which discloses methods for installing a flexible spinal needle assembly and methods of delivering a fluid may include inserting a distal end of a flexible spinal needle assembly into a subject and, thereafter, disposing an anti-restriction member at least partially within an inner flow path of the flexible spinal needle to substantially prevent fluid occlusion caused by bending or kinking of the flexible spinal needle.

(7) U.S. Patent Application Publication No. 2006/0206055 by Ice which discloses an epidural injection needle with a larger-gauge proximal shaft that tapers in close proximity to a smaller-gauge distal tip. A conventional stylet of suitable material is employed to stiffen the needle and to prevent material from entering the needle during insertion. Wings can be fitted to facilitate manual guidance of the needle. The short-tapered design provides an epidural injection needle having a shaft large and stiff enough so that it can be reliably guided to the epidural space but also having a small tip which minimizes trauma to blood vessels, nerves, and other tissues that may be inadvertently punctured during the procedure. This enables epidural injections to be safer for patients than those utilizing commercially available needles or prior-art designs.

(8) U.S. Patent Application Publication No. 2011/0112511 by Singer which discloses a method and apparatus for administering liquid anesthetics around peripheral nerves, in order to perform surgery or to relieve post-operative pain. The apparatus includes a regional anesthetic needle with an overlying catheter. The needle is hollow and has a blunt end so that it does not penetrate or damage a nerve or blood vessel. A stiff catheter covers the needle up to a side hole in the needle that allows liquid anesthetic to be injected through the needle in a forward direction. The needle can be removed by leaving the catheter in place without disturbing the location of the catheter.

(9) U.S. Patent Application Publication No. 2011/0201930 by Guzman which discloses a procedure and kit are provided for performing an ultrasound-guided transversus abdominis plane (TAP) procedure. The patient's abdomen is scanned with an ultrasound probe to identify and mark the external oblique, internal oblique, and TAP. An introducer sheath is placed over a fluid delivery needle such that the distal end of the needle extends beyond the distal end of the sheath, the needle having echogenic properties for ultrasound imaging.

The needle and sheath are ultrasonically guided into the TAP. A local anesthetic or saline/anesthetic combination is injected through the needle to create a liquid pool in the TAP. The needle is removed from the sheath while maintaining the sheath within the TAP and a catheter is subsequently advanced through the sheath and into the pooled liquid in the TAP. The sheath is withdrawn while maintaining the catheter located within the TAP. A catheter is connected to a source of local anesthetic for providing a defined volume of anesthetic to the catheter site at a controlled delivery rate.

(10) U.S. Patent Application Publication No. 2012/0059308 by Hsu which discloses an anesthetic nerve block catheter and methods of using the anesthetic nerve block catheter to perform a nerve block or continuous nerve block procedure are disclosed.

(11) U.S. Patent Application Publication No. 2012/0232389 by Guzman which discloses an apparatus for administering certain nerve blocks includes a sheath constructed from a flexible ultrasound echogenic material, a more rigid introducer/dilator for introducing the sheath into the patient, and an ultrasound echogenic catheter for inserting through the sheath once the distal end of the sheath is in place adjacent the nerve(s) to be blocked and the introducer/dilator has been withdrawn. The catheter has provisions at its proximal end for connecting to a source of local anesthetic. Methods for use of this apparatus are also described.

Aspects of the invention relate to novel medical apparatuses and methods for placement of a continuous nerve conduction catheter for prolonged neural blockage in the area of providing patients with pain relief. The apparatus can be placed with minimally involved methodology that requires only a single operator, particularly when assisted by ultrasound guidance, allowing for continuous visualization or by other means known in the art.

In one embodiment, the apparatus includes a sheath having a proximal end, a distal end and at least one lumen extending from the proximal end to the distal end. The terms sheath and catheter are used interchangeably throughout the specification. The sheath may also include an embedded conductive element for transmitting an electrical signal from a proximal portion of the sheath to a distal portion of the sheath. The sheath may be reinforced or not reinforced in any of the embodiments of the invention. A cannula or introducer is arranged in at least one lumen of the sheath and has a distal end protruding from a distal portion of the sheath. The terms cannula, needle, and introducer are used interchangeably throughout the specification. The cannula is electrically coupled to at least a portion of the embedded conductive element and may be configured to provide nerve stimulation independently or in conjunction with the sheath.

The cannula may include a sharp tip, a short beveled tip and/or a bullnose tip with a lateral port. The cannula may also be a Touhy needle, Crawford needle, Hustead needle, Sprotte needle, Whitacrea needle, Quincke needle, or other medical needles. In a preferred embodiment, the gauge of the needle is in a range from about 6 to about 26 and more preferably the gauge of the needle is in a range from about 18 to about 20. The cannula may be hollow or solid. The cannula as described with reference to U.S. Patent Application Publication No. 2011/0112511, which is hereby incorporated by reference as if fully set forth herein, may be used.

The cannula may also include one or more solid state sensors, e.g., temperature, pressure, and/or flow rate. Multiple sensors may also be used throughout the lumen of either the cannula and/or catheter. These sensors may be configured to communicate wirelessly via Wi-Fi, Bluetooth, and/or other wireless communication protocols as known in the art to a readout or other device (not shown) such as a controller. Of course, the sensors may be hardwired to communicate directly with a readout or other internal or external device.

The terms sheath, sleeve, and catheter are used interchangeably throughout the specification. The sheath may be constructed as a reinforced catheter with various materials. For example, the sheath may include polyesters; polyurethanes; polyamides; polyolefins including polyethylene and polypropylene; and any copolymers thereof. Some more specific examples of suitable materials include, but are not limited to: nylon; polyester elastomer; polyether/block polyamide, such as Pebax, Hytrel, and/or Arnitel; polyamid such as Grilamid; fluoro-polymer, such as Kynar; polyether ether ketone (PEEK); polyethylene (PE); polyurethane; polyolefin copolymer (POC); tetrafluoroethylenes, such as polytetrafluoroethylene (PTFE). In a preferred embodiment, the sheath is reinforced with materials configured to substantially prevent kinking of the sheath.

The catheter may also be constructed, in whole or in part, utilizing a variety of degradable materials, polymeric materials, synthetic or natural, and combinations thereof. Furthermore, the catheter may be composed such that the portion of the catheter that enters and remains in the patient is degradable, but the portion that remains substantially outside of the patient is not degradable. Furthermore, a break point may exist between the two materials to assist in separating the catheter, e.g., leaving the degradable portion in the body while the non-degradable is removed. In this type of arrangement the patient would not have to return to the physician to remove the catheter.

Degradable materials include bioabsorable materials, e.g. such as, polymers and copolymers composed from varying amounts of one or more of the following monomer examples, glycolide, d,l-lactide, l-lactide, d-lactide, p-dioxanone (1,4-dioxane-2-one), trimethylene carbonate (1,3-dioxane-2-one), $\epsilon$-caprolactone, $\gamma$-butyrolactone, $\delta$-valerolactone, 1,4-dioxepan-2-one, and 1,5-dioxepan-2-one.

The sheath may also include solid state sensors, e.g., temperature, pressure, and/or flow rate. The sheath may also include a communication means such as receiver/transceiver for communication via wireless, bluetooth, radio frequency (RF) and/or other protocols as known in the art.

The sheath and cannula may include antibacterial materials such as coatings and/or micropatterned surfaces to inhibit or prevent unwanted accumulation of organic and/or inorganic matter of biological origin on surfaces. The micropatterned surfaces for controlled bioadhesion are described within PCT Application No. PCT/US10/59246, which is hereby incorporated by reference as if fully set forth herein. The micropatterned surfaces are also sold under the brand name Sharklet™. In addition, the coatings may include broad-spectrum antimicrobial coatings such as silver, nanosilver and other antimicrobial coatings as known in the art. In one embodiment, the antibacterial coatings for the catheter and/or cannula are described with reference to U.S. Patent Application Publication No. 2013/0084319, which is hereby incorporated by reference as if fully set forth herein.

In another embodiment, the invention is directed towards a method for administering a continuous flow or intermittent bolus of anesthetic agent to facilitate a continuous or prolonged nerve block. The method includes providing a sheath having a proximal end, a distal end and at least one lumen extending throughout a portion of the sheath. The sheath may include an embedded conductive element for transmitting an electrical signal from a proximal portion of the sheath to a distal portion of the sheath. The method includes providing a cannula into at least one lumen of the sheath.

The continuous anesthesia nerve conduction apparatus is configured to allow a physician to perform the procedure within approximately ten minutes or less, and preferably within approximately five minutes or less. With a minimal sterile setup, and easy identification of the targeted nerve(s), positioning the cannula adjacent to the nerve(s) permits the sheath positioning with a single hand in one continuous motion.

There are several advantages of having a catheter and/or needle that has a different diameter at a distal region as compared to the body region or even a proximal region. A few of these advantages are as follows.

During a procedure a vital part of positioning a catheter is to ensure that the catheter tip is in close proximity to the targeted nerve(s). Identification of the catheter tip is conventionally done by some form of echogenic marking. If the marking is localized only to the tip, then the marking is very small and is often difficult to visualize with ultrasound imaging. If the marking is along the entire length of the catheter, then the tip is difficult to distinguish from the catheter shaft. Altering the diameter of the distal portion of the catheter or tip portion from the body portion or shaft of the catheter is a novel and functional way to identify the catheter tip on ultrasound imaging so the operator can easily determine when the catheter tip is properly positioned to increase efficacy and reduce the time of the procedure.

By way of example, the space surrounding a neural structure is limited and the pocket created by hydro-dissection is small. A smaller diameter distal portion or catheter tip permits the distal portion to more effectively attain the shape within the limited space around the nerve(s).

Some nerve blocks are performed in locations where the space between the nerves and the surrounding tissue is very tight. The Thoracic Paravertebral block is one such case where the space around the nerve is small and advancing too far results in puncturing the lung. By having a smaller diameter tip on the catheter and needle, the catheter can be maneuvered more precisely within the confines of the paravertebral space.

In a preferred embodiment, a curved needle and/or curved catheter can be utilized with the system. The curved needle helps direct the catheter in a particular direction. Most nerve block procedures are most effective when the catheter is positioned to provide radial spread of local anesthetics. Neural structures are frequently cylindrical in shape and by positioning the catheter to cover an area in a range from about 75 degrees to about 280 degrees surrounding a nerve thereby provides the best radial spread of the local anesthetic. A curved needle allows for the hydro-dissection at an angle different than that of the insertion angle of the needle and directs the catheter away from a perpendicular orientation to the nerve(s). The curvature of the needle is not so great as to inhibit the insertion of the needle/catheter unit.

In one embodiment, the medical apparatus includes a catheter having a proximal end, a distal end, a lateral port, a distal end region, proximal end region, and at least one lumen extending from the proximal end to the distal end. The distal end region includes a first diameter and a proximal end region has a second diameter. The apparatus may also include a disposable pump and cannula configured to be arranged in at least one lumen. The first diameter may be smaller or greater than the second diameter. The first diameter can be configured to taper to the second diameter at a transition region or point between the diameters. The taper can be a non-linear taper shape, linear taper shape and combination of the same.

In one embodiment, the distal end region having a different diameter than another portion of the catheter can have a total length in a range from about 0.1 cm to about 5 cm, and preferably, the distal end region has a total length in a range from about 1 cm to about 1.5 cm. The diameter of the distal end region may be constant or variable, e.g., it may include a taper from a proximal end of the distal end region to the distal end of the catheter. By way of example, the taper can include a third diameter and a fourth diameter. In one embodiment, the fourth diameter is smaller than the third diameter and the third diameter is smaller than the first diameter. The diameter of the first diameter, second diameter, third diameter, and/or fourth diameter may be in a range from about 5 gauge to 25 gauge, preferably in a range from about 17 gauge to about 22 gauge and most preferably in a range from about 18 gauge to about 20 gauge.

Any portion of the catheter may include an echogenic material and/or radiopaque material as described herein. The distal end region may include a first material having a first ultrasound visualization property and the proximal end region and/or rest of the catheter may include a second material having a second ultrasound visualization property. In one embodiment, the first material and second material are the same. In another embodiment, the first material comprises a thermoplastic material only and the second material includes a thermoplastic material only. In one embodiment, the first thermoplastic material is different than the second thermoplastic material. In a preferred embodiment, the distal end region of the catheter and/or cannula is configured to bend or curve at angle in range from about 5 degrees to about 175 degrees relative to the central axis. In one embodiment, the apparatus may include an electrical connection element near a distal portion of the catheter, wherein the electrical connection element is configured to be coupled to a nerve stimulator.

The method further includes connecting a syringe configured to administer a pharmacological agent to the distal end of the cannula and coupling an electrical signal generator to the embedded conductive element or to the cannula directly. Next, the cannula and sheath are inserted simultaneously into the patient. The method includes locating at least one nerve of the patient with at least one of an electric signal generated from the electrical signal generator or an active imaging device and administering a pharmacological agent to the at least one nerve after advancing and positioning the sheath off of the cannula with a single hand. If needed, a guidewire is directed through the lumen of the cannula to position the sheath in a semi-circumferential near the nerve(s).

Yet another embodiment of the invention is directed towards a kit, e.g., a medical package. The kit includes an apparatus for administering a continuous flow or intermittent bolus of anesthetic agent to facilitate a continuous or prolonged nerve block and directions for use. The kit may optionally include a pump for administering a pharmacological agent, e.g., a disposable infusion pump. Disposable infusion pumps are known in the art such as the ON-Q® C-bloc-Continuous Nerve Block System by I-Flow Corporation, PainPump 1, PainPump 2, PainPump 2 BlockAid by Stryker Corporation, and GoPump® or GoBlock® by Symbios. In some embodiments, the kit includes items that have been sterilized and recycled. These items may include for example, portions of the pump and exterior components such as clips and luers. Several configurations of the pump may be used, including pumps described in U.S. Pat. Nos. 5,284,481; 7,322,961; 5,352,201 and 5,080,652, each of which is incorporated herein by reference in their entirety.

Reference will now be made in detail to an embodiment of the present invention, example of which is illustrated in the accompanying drawings.

FIG. 1 illustrates an operational systematic view of continuous anesthesia nerve conduction system according to an embodiment of the invention.

Figure 28A:
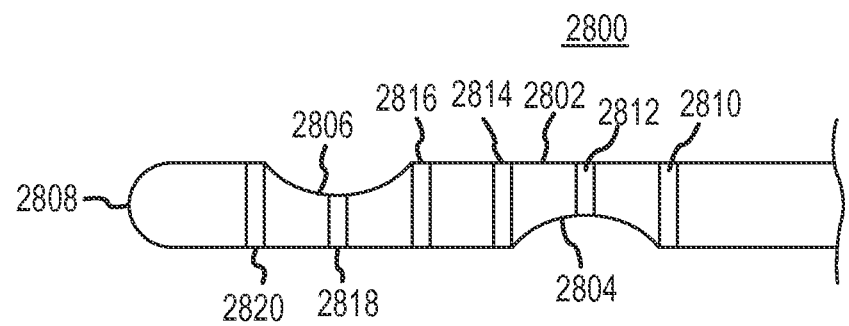
FIG. 28A illustrates a distal portion of a continuous anesthesia nerve conduction apparatus according to another embodiment of the invention.
Figure 28B:
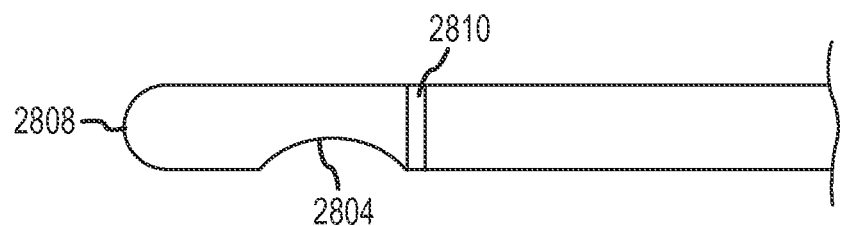
FIG. 28B illustrates a distal portion of a continuous anesthesia nerve conduction apparatus according to another embodiment of the invention.

Referring to FIG. 1, the system is generally depicted as reference number 100. The system overview 100 includes an exterior portion of a sheath 102. The sheath 102 is secured to the skin of the patient with securing tab or tabs 103 and anchored to a hub 104. Nerve(s) 106 lying deep in tissue below the exterior surface of the patient are targeted to receive a pharmacological agent. A subcutaneous distal portion of the sheath 108 is shown positioned in close proximity to the targeted nerve(s) 106, e.g., nerves of the brachial plexus. The sheath 108 may include a side port and markings to aid with external visualization, e.g., active or passive visualization. The markings may be spaced apart to aid in further visualization and orientation of the side port as shown in FIGS. 28A and 28B.

An infusion pump 110 which may be filled with a pharmacological agent, e.g., pain medication such as a nerve block, is connected to the apparatus via connecting tubing 112, by way of example, with Luer locking connectors to the hub 104. The pump 110 can include an ON-Q® C-bloc-Continuous Nerve Block System by I-Flow Corporation, PainPump 1, PainPump 2, PainPump 2 BlockAid by Stryker Corporation, and GoPump® or GoBlock® by Symbios. For example, the pump may include a pump as described in U.S. Pat. Nos. 5,284,481; 7,322,961; 5,352,201 and 5,080,652, each of which is incorporated herein by reference in their entirety. Several different configurations of the tubing may be used. For example, a coupler may be used so that the pharmacological agent in the pump may be directed to multiple locations in the body. In addition, multiple catheter units may be used and different configurations of the catheter may also be used.

Figure 7:
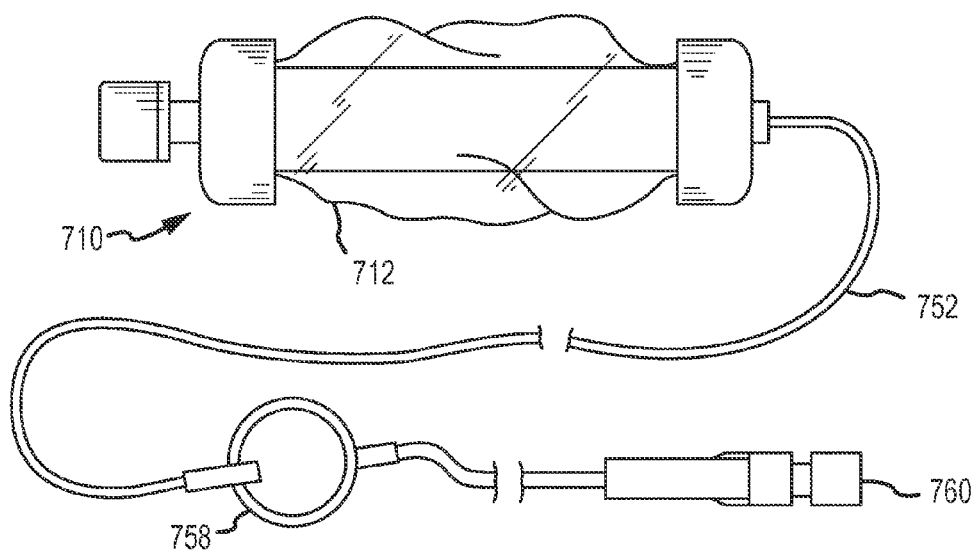
FIG. 7 illustrates an infusion pump.
Figure 8:
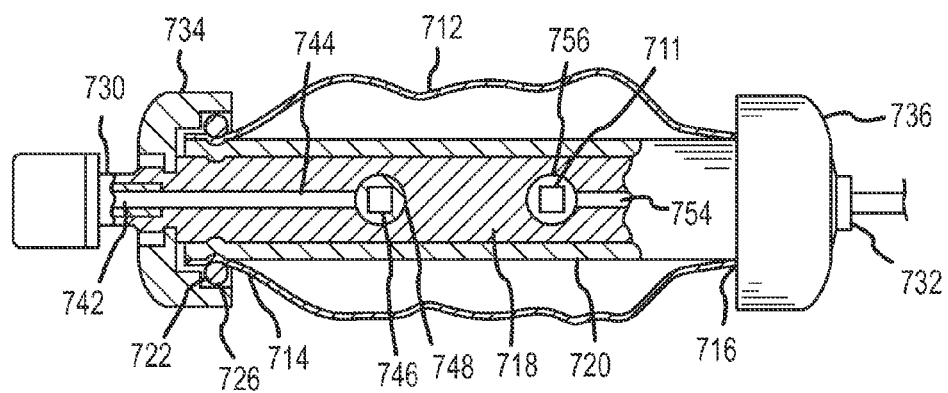
FIG. 8 illustrates a cross-sectional view of the infusion pump of FIG. 7.

Several different configurations of the pump 110 may be used. In a preferred embodiment, a disposable pump, infusion pump and other inexpensive pumps as known in the art is used with a continuous anesthesia nerve conduction apparatus. Such as an infusion pump 110 such as that described in U.S. Pat. No. 5,284,481, which is incorporated herein by reference, may be used. FIGS. 7 and 8 illustrate exemplary embodiments of infuser pumps. The infuser pump, designated generally by the numeral 710, is collapsible and includes an outer collapsible, substantially non-stretchable housing or shell 712, protectively mounted over a combined reservoir and support assembly constructed substantially like that set forth in U.S. Pat. Nos. 5,080,652 and 5,105,983, each of which is incorporated herein by reference as though fully set forth herein.

The collapsible housing 712 has a substantially spherical configuration for confining and guiding the inflatable reservoir or bladder into a concentric position around the central support member, and enabling it to expand naturally in a spherical configuration as will be described. However, other geometric configurations are also possible for the collapsible housing. The collapsible housing 712, as seen in FIG. 8, has coaxial openings defined by tubular sleeve extensions 714 and 716 through which the ends of a central support member 718 extends.

An elastic membrane or bladder assembly 720 forming an inflatable reservoir, such as described in the aforementioned patents, is mounted on the cylindrical support member 718. The bladder assembly 720 may be a single sleeve or multiple sleeves. This is preferably with an inner sleeve being a chemically inert sleeve, and the outer sleeve or sleeves being highly elastic.

The central cylindrical support member or mandrel 718 includes circular grooves only one of which, 722 is shown, at the ends thereof into which portions of the sleeve 720 and housing 712 are biased with a pair of O-rings, only one of which, 726, is shown. The collapsible housing 712 is preferably a non-stretch blow molded housing of five to ten mil-inches in thickness and made of a material such as polyurethane, PVC film, and/or polyethylene and is transparent. This forms a simple inexpensive compact unit with a certain amount of protection for the elastic reservoir.

Certain applications may require a tougher collapsible housing. In such cases, the housing can be transparent, UV stable, flexible and highly resistant to puncturing. In this configuration, the housing would be constructed of a material such as tough composites in a flexible form such as a fabric, reinforced thermoplastic, Kevlar material which includes a para-aramid synthetic fiber, related to other aramids such as Nomex and Technora, and combinations of the same.

The ends of the central support member 718 include reduced diameter extension 730 and 732, with bayonette type couplings for releasably coupling cup-shaped caps 734 and 736 which extend over and protectively cover the O-ring connections or clamping of the elastic bladder and collapsible housing to the support member.

The support member 718 has an inlet or fill port 742 on one end which communicates with a coaxial passage 744, and a transverse passage 746 in which is mounted a check valve 748. The cross bore 746 communicates with passage 744 and inlet port with the interior of the elastic bladder or sleeve 720 and thus the interior of the inflatable reservoir. The check valve is also used and is of a generally cylindrical outer shape, with a square bore extending from one end and closed at the other forming a cup-shaped structure. The check valve may be constructed of materials known in the art, e.g., an elastomer like silicone, and collapses inward to allow filling and erects to its normal configuration to prevent back flow. The square bore configuration of the bore insures that it returns to its normal configuration and does not remain collapsed.

An outlet port through end 732 communicates with a passage 754 that extends coaxially from the other end of the support member 718, and communicates with a cross bore or port 756 with the interior of the elastic bladder or reservoir 720. The port 756 may include a sensor 711 to measure flow rate, pressure, liquid volume, and temperature among other characteristics. Multiple sensors may also be used throughout the interior. These sensors may be configured to communicate wirelessly via Wi-Fi, Bluetooth, and other wireless communication protocols as known in the art to a readout or other device (not shown) such as a controller. Of course, the sensors may be hardwired to communicate directly with a readout or other internal or external device.

A tubing set, as shown in FIG. 7 including a tube 752 having a filter 758 and a connector 760 at the end, provides a device for connecting and dispensing a fluid to a desired location, such as a catheter (FIG. 1) as described herein. The connector 760 may be permanently attached to the tube 752, or may be removable. Furthermore, any suitable connector may be used, including a luer connector or others as known in the art.

The collapsible infuser apparatus of FIGS. 7 and 8 is a compact and inexpensive disposable unit. It has a compact configuration, with a collapsed diameter no greater than the outer diameter of the caps 734 and 736. For this reason, it is convenient to package in a kit as described herein. Optionally, it may be temporarily housed during use in a protective hard shell housing.

Figure 9:
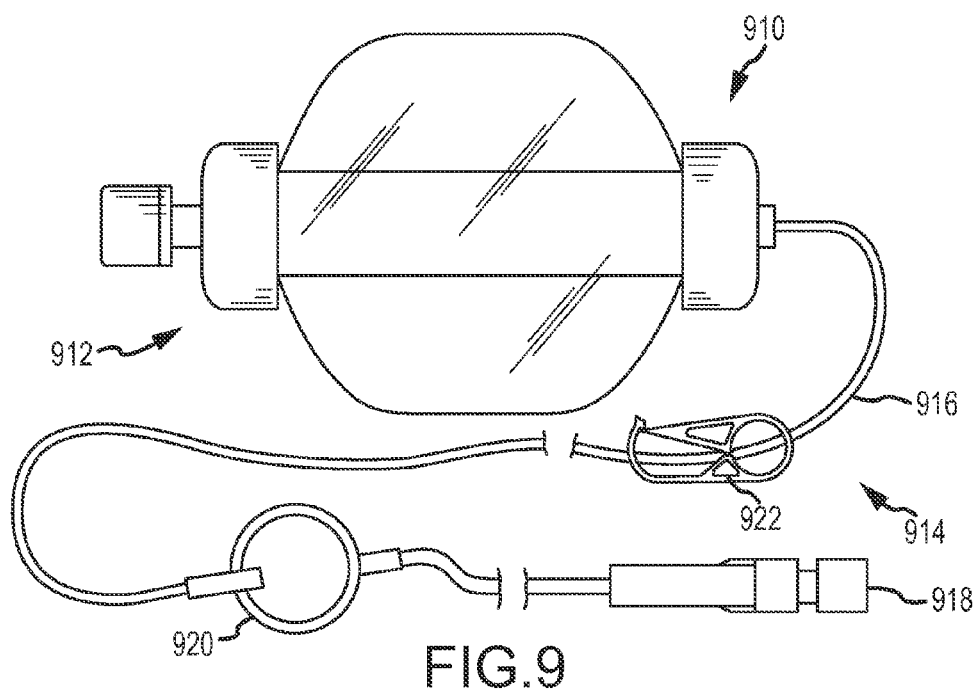
FIG. 9 illustrates an infusion pump.
Figure 10:
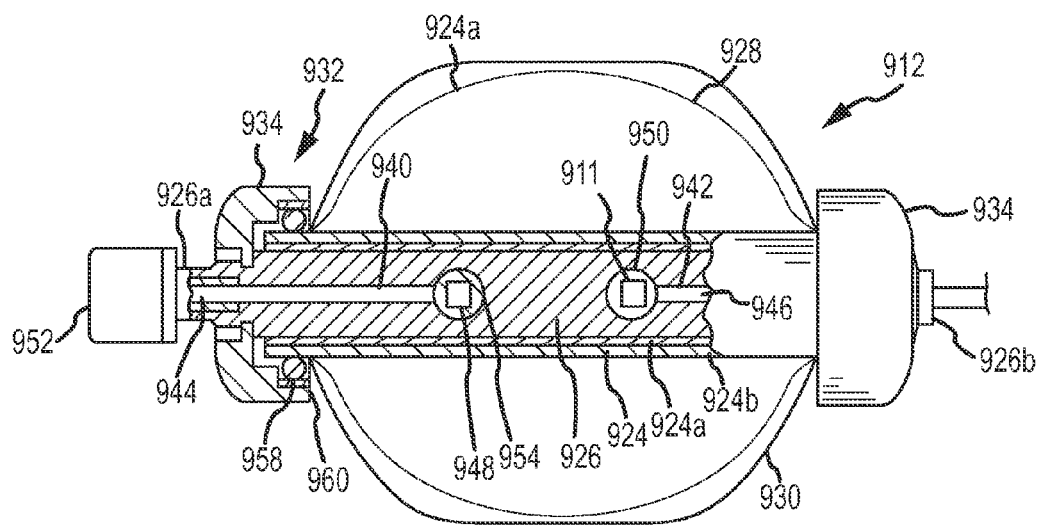
FIG. 10 illustrates a cross-sectional view of the infusion pump of FIG. 9.

In another embodiment, the pump 110 may be the pump described in U.S. Pat. No. 7,322,961, which is hereby incorporated in its entirety by reference. FIGS. 9 and 10 illustrate an infusion pump or apparatus, generally referred to by the reference numeral 910. The infusion apparatus 910 is operable to deliver a pressurized liquid, such as a pharmacological agent, e.g., pain medication, to a desired site such as a catheter (FIG. 1). Preferably, the infusion apparatus 910 is relatively inexpensive, portable and provides reliable operation throughout its useful life. The infusion apparatus 910 may be reusable or may be disposable after a single use.

The infusion apparatus 910 desirably includes an infusion pump 912, which is configured to hold a pressurized supply of a fluid, such as a pharmacological agent. Preferably, a supply arrangement 914 includes in substantial part by a length of medical tubing 916, is in fluid communication with the infusion pump 912 at a first end. The supply arrangement 914 supplies the pressurized fluid to the catheter or other delivery device, through an appropriate connection device 918 at a second end. The medical tubing 916 may be formed of any of a variety of materials suitable for use in medical applications. Preferably, such materials are constructed form a polymeric material and substantially bio and/or chemically inert. Similarly, the connector 918 may be any suitable device to permit relatively quick and secure connection between a pair of medical devices, such as a luer lock, for example. Other types of suitable connectors may also be used.

In a preferred embodiment, the supply arrangement 914 includes a filter 920 in serial connection with the medical tubing 916. The filter 920 desirably is configured to remove impurities, including air bubbles, from the fluid delivered from the infusion pump 912. The filter 920 may be any suitable medical filter as known in the art.

Preferably, the supply arrangement 914 also includes a clamp 922, which is desirably positioned upstream of the filter 920. The clamp 922, in a closed position, is configured to apply a squeezing pressure to the medical tube 916 to close the lumen therein and occlude fluid flow beyond the clamp 922. Any suitable type of medical clamp may be used.

With reference to FIG. 10, the infusion pump 912 generally includes an elastic sleeve 924 surrounding a support member. Preferably, the support member 926 is generally cylindrical in shape; however, other suitable shapes of support members may also be used. The elastic sleeve 924 is expandable in a radial direction about the cylindrical support member to an expanded condition 924a. In the expanded condition 924a, the elastic sleeve 924 and the support member cooperate to define a variable volume fluid reservoir 928 therebetween.

Preferably, the infusion pump 912 is configured such that the reservoir 928 may be filled (also referred to as "loading" the pump 912), from an inlet end 926a of the support member. Preferably the infusion pump 912 may be manually loaded with a loading device, such as a syringe. Once the reservoir 928 has been filled with fluid, the elastic nature of the sleeve 924 exerts a pressure on the fluid within the reservoir 928, permitting the fluid to be delivered to a desired site catheter through the supply arrangement 914 and delivery device, e.g., device of FIG. 1.

The sleeve 924 may include a single layer or multiple layers. The inner sleeve 924a may include a bio and/or a chemically inert material to avoid interaction with the drug within the infusion pump 912 while an outer sleeve 924b may include a material having desirable elastic properties. The combination of the sleeves 924a, 924b desirably provide satisfactory elastic properties and desirable chemical properties to consistently and safely deliver the pressurized fluid, such as a pain medication. In one arrangement, the inner sleeve 924a may include a semi-elastic thermal plastic material. The outer sleeve 924b may include a natural latex rubber material, which provides desirable elastic characteristics. However, other suitable materials may also be used.

If desired, the infusion pump 912 may also include a protective, collapsible housing, or pouch 930 surrounding the elastic sleeve 924. Desirably, the pouch 930 is relatively inelastic to limit expansion of the sleeve 924. In addition, the pouch 930 desirably is made from a tougher material than that of the sleeve 924 in order to protect the sleeve from punctures, or other damage. In one preferred arrangement, the pouch 930 includes a pair of flat, sheet-like portions bonded to one another around their peripheral edges. Preferably, the portions of the pouch 930 comprise a PVC material, which are bonded to one another by Radio Frequency (RF) welding. Such a construction provides a suitable, economical means to protect the elastic sleeve 924 from damage. Other suitable materials and construction techniques may also be employed.

Desirably, the elastic sleeve 924 is sealed to the cylindrical support member 926 at spaced apart locations near each end 926a, 926b of the cylindrical support 926 by a pair of seal assemblies 932 (only one shown). The reservoir 928 of the infusion pump 912 is defined between the pair of seal assemblies 932. If a housing or pouch 930 is provided, end portions thereof may also be held in place by the seal arrangement 932. These and other details of the sealing arrangements 932 are described in greater detail below.

Desirably, a cap 934 is attached to each end of the infusion pump 912. Preferably, each cap 934 includes a side wall portion which at least partially covers the sealing arrangement 932. Such an arrangement serves to inhibit damage to the sealing arrangement 932 during normal use of the infusion apparatus 910 and provides an aesthetically pleasing outward appearance. Other sealing mechanisms may be used.

The cap 934 is removably connectable to the support member 926. In a preferred embodiment, the cap 934 is coupled to the support member 926 by a snap fit arrangement wherein the cap 934 includes a triangular-shaped cutout 936. The cutout 936 is sized such that a portion of each side of the triangular-shaped cutout 936 may be received within an annular recess defined by the cylindrical support member 926. Desirably, the cap 934 is constructed from a material having sufficient flexibility such that the side portions of the cutout 936 may deflect to pass over the end portion of the support member 926, which has a larger diameter and is positioned outwardly, along the support member 926, from the recess. Any of a variety of common thermoplastic materials may be suitable for use in construction of the end cap 934. Other suitable end cap constructions may be used, such as a threaded end cap arrangement, plug, and the like.

The infusion pump 912 also includes an inlet 940 and an outlet 942 in fluid communication with the reservoir 928. In the illustrated embodiment, the inlet 940 and outlet 942 are at least partially defined by the support member 926. Desirably, each of the inlet and outlet 940, 942 include a longitudinally extending channel 944, 946, respectively, which open to opposing end surfaces of the support member 926. In addition, each of the inlet and outlet 940, 942 include a radially extending channel 948, 950, respectively, which communicate with the longitudinal channels 944, 946 and open from a portion of the side wall of the cylindrical member 926 located within the fluid reservoir 928, or the reservoir wall. A sensor 911 to measure flow rate, pressure, liquid volume, and temperature among other characteristics. Multiple sensors may also be used throughout the interior of the infusion pump 912. These sensors may be configured to communicate wirelessly via Wi-Fi, Bluetooth, and other wireless communication protocols as known in the art to a readout or other device (not shown) such as a controller. Of course, the sensors may be hardwired to communicate directly with a readout or other internal or external device.

The inlet-defining end 926a of the support member 926 desirably is configured to receive a reservoir loading device, such as a syringe, which may be interconnected to the support member 926 by a threaded connection, such as a luer lock connection, for example. In operation, the loading device introduces fluid into the fluid reservoir 928, against the biasing force of the sleeve 924. Desirably, once the infusion pump 912 has been loaded with fluid, the inlet end of the support member 926 is closed by a cap 952. The elasticity of the sleeve 924, once expanded 924a, pressurizes the fluid within the reservoir 928.

Preferably, the inlet 940 includes a one-way valve to inhibit fluid within the reservoir 928 from escaping through the inlet 940. The valve includes a valve member 954 positioned within the radially extending channel 948. The valve member 954 is desirably cylindrical in shape and includes a recess extending, from an end surface, along a longitudinal axis of the valve member 954. Preferably, the recess is generally square in cross-section and extends substantially the entire length of the valve member 954, thereby defining a closed end of the valve member 954 having a thickness approximately equal to a thickness of the outer wall portion of the valve member 954.

When installed in the radially extending channel 948, a portion of the wall of the valve member 954 facing the longitudinal channel 944 collapses in response to fluid being loaded in the infusion pump 912 through the inlet 940. However, once the fluid pressure within the inlet 940 is lower than the pressure within the reservoir 928 (i.e., filling of the reservoir 928 has ceased), fluid within the recess urges the valve member 954 back into its original, cylindrical orientation to inhibit fluid from entering the longitudinal channel 944 and, thus, exiting the reservoir 928 through the inlet 940. Other suitable valves may also be used as known in the art.

Desirably, the longitudinal channel 946 of the outlet 942 extends through an outlet end 926b of the support member 926 and communicates with the medical tubing 916 of the supply arrangement 914. Desirably, the outlet 942 permits relatively unobstructed fluid flow. That is, a one-way valve mechanism is not necessary or desirable in connection with the outlet 942. Accordingly, with such an arrangement, fluid flow from the reservoir 928 through the outlet 942 is selectively permitted by the clamp 922 of the supply arrangement 914.

Optionally, the pump 912 may include a flow restrictor (not shown) downstream from the fluid reservoir 928. The flow restrictor is configured to restrict the flow rate of fluid exiting the fluid reservoir 928 to a desired level. The flow restrictor may comprise a reduced-diameter of the outlet passage 946 (in whole or in part), the diameter of the tubing 916 (FIG. 9), or a separate flow restrictor device positioned downstream from the fluid reservoir 928. Other suitable arrangements are also possible, including a combination of the above-mentioned flow restrictor arrangements.

The seal arrangement 932 is described in greater detail. The seal arrangement 932 desirably includes an annular recess, or groove 958, near an end of the support member 926. The recess 958 is defined by an outer surface of the support member 926 and, preferably, is substantially semi-circular in shape. A generally annular spring clip 960 is sized to be positionable onto the support member 926 and, preferably, cooperate with the recess 958 to create a seal between the sleeve 924 and the support member 926.

The spring clip 960 is configured to be movable from a relaxed position, or a free diameter of the spring clip 960, to a deflected position. In the relaxed position, an inner diameter of the spring clip 960 desirably is smaller than a diameter of the support member 926 with which the spring clip 960 is positioned. In the deflected position, the inner diameter of the spring clip 960, desirably, is large enough to pass over the elastic sleeve 924 and cylindrical support member 926 to permit assembly onto the infusion pump 912. Once released, the spring clip 960 returns toward the relaxed position. Preferably, the support member 926 is sized such that the spring clip 960 is prevented from returning to the fully relaxed position. Accordingly, the spring clip 960 exerts a squeezing force on the elastic sleeve 924 to create a seal between the sleeve 924 and the cylindrical support member 926 thereby defining an end of the fluid reservoir 928. As will be appreciated by one of skill in the art, the squeezing force developed by the spring clip 960 may be adjusted to a desired level by altering the relative sizes of the inner diameter of the spring clip 960 and the outer diameter of the corresponding portion of the support member 926, as well as by altering the properties of the spring clip 960 itself, such as the coil diameter of the spring clip 960, for example.

Desirably, the elastic sleeve 924 (and pouch 930, if provided) is biased into the recess 958 by the spring clip 960. Such an arrangement assists in defining and maintaining a proper position of the spring clip 960 relative to the support member 926. In addition, the deflection of the sleeve 924 into the recess 958 increases the effectiveness of the seal arrangement. Although only the inlet side 926a seal arrangement 932 is shown, preferably the outlet side 926b is constructed substantially similarly to that of the inlet side 926a. Preferably, the spring clip 960 is constructed of metal; however, other suitable materials such as plastics may also be used.

Figure 11:
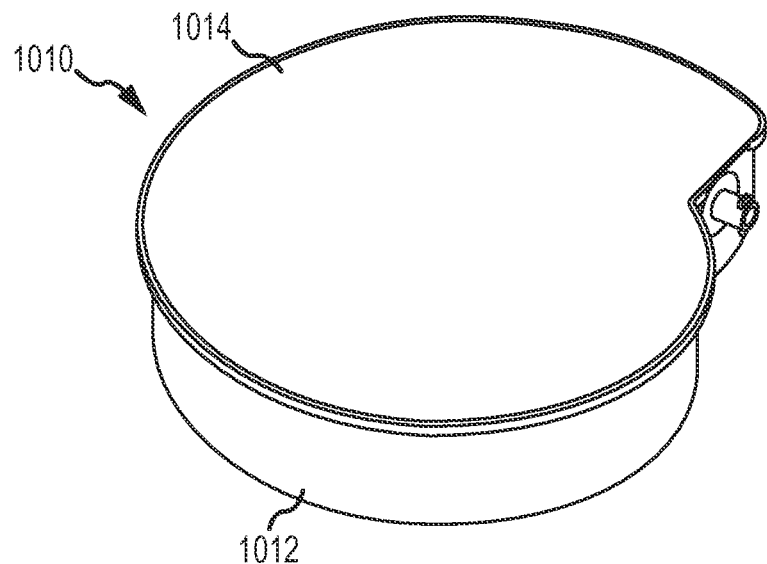
FIG. 11 illustrates an infusion pump.
Figure 12:
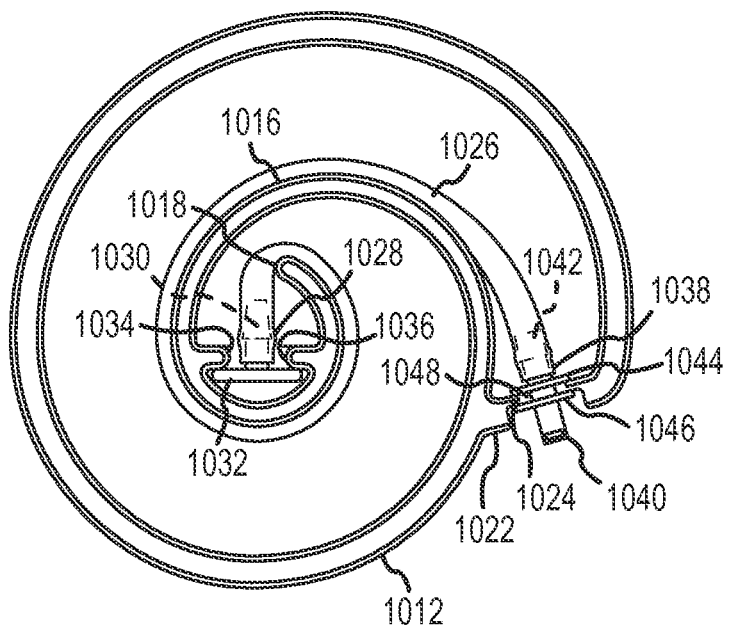
FIG. 12 illustrates a top view of the infusion pump of FIG. 11, without the cover.

In another embodiment, the system may include a pump 110 as described in U.S. Pat. No. 5,352,201, which is incorporated in its entirety by reference. FIGS. 11 and 12 illustrate the infusion pump or apparatus, generally referred to by the reference numeral 1010. The infusion apparatus is embodied in a housing having a generally flat spiral configuration. However, it may have other outer configurations such as circular, semicircular or square. The apparatus includes a main housing having thermally formed walls extending upward from a bottom and extending in a radially outward spiral to a terminal end such that all the connections are provided. The main housing has an open top formed for receiving a generally flat planer cover 1014. The cover 1014 may be formed with recesses or other structural configurations to enable stacking of a plurality of the units.

The housing is preferably formed of any one of a number of thermoformable plastic polymer materials and vacuum formed into its shape or configuration. Either the housing 1012 or the cover 1014 or both may be of a transparent material. Preferably at least one is transparent in order to enable viewing the components in the interior of the housing. They may also be formed together of the same material with an integral hinge connection as will be explained. Referring to FIG. 12, the main housing is shaped to form a spiral bladder support and chamber from a central point of the housing spiraling outward to the terminal outlet face of the housing. The housing is formed of an inner wall 1016 beginning at an inner end 1018 proximate the center of the housing and spiraling outward in a radially outwardly spiral to become an outer wall and continue to a terminal end 1022, joining the outer surface or portion thereof and forming a terminal wall 1024. The angle subtended by the spiral is preferably in a range from about ¾ turn and about two turns or greater.

The inner wall 1016 forms a spiral support structure for supporting an elongated elastic tubular member 1026 forming an elastic bladder or reservoir. The coils of the elastic tube are supported in a common plane and spiral radially outward. The elastic tube or member 1026 is preferably pre-stretched up to about 30% with an inner end 1028 secured on a barbed plug 1030 having a shoulder 1032. The shoulder 1032 is positioned behind shoulders formed by inner extending wall portions 1034 and 1036 forming a receptacle for receipt of the plug 1030. The elastic tube or member is stretched and bends across the inner end 1018 or wall of mounting member 1016 and lies compressed substantially flat, as it extends along the wall to an outlet end 1038 connected to an outlet connector and valve assembly including a suitable coupling or connector such as a luer connector 1040.

The housing of the valve and connector assembly is of a tubular configuration with an inner barbed connector 1042 over which an outer end 1038 of elastic tube 1026 is mounted. The housing of the connector includes spaced apart disc or shoulder plates 1044 and 1046 which embrace and engage opposing sides of the wall 1024 as the connector is inserted in a slot 1048 therein. This secures the connector in place against movement either inward or outward of the housing. The elastic bladder 1026 is stretched and mounted between barbed connectors 1030 and 1042.

The connector assembly 1040 preferably includes a luer check valve of a type for such fittings normally available from the Halkey-Roberts Company of St. Petersburg, Fla. The valve (not shown) is a one-way check valve to prevent outflow until a luer connector is mounted on the outlet end of the connector which acts to release or unseat the valve.

The housing may be constructed of any number of suitable engineering thermo forming materials such as, acrylonitrile butadiene-styrene (ABS), polyvinylchloride (PVC), polyethylene terephthalate (PET), polyethylene terephthalate glycol (PETG) and the like. These are well-known lightweight plastics and are materials approved for medical devices.

The tubular member 1026 is preferably constructed of an inner tube or sleeve of an inert elastomer and an outer highly elastic tube or sleeve. A preferred rubber material for the inner sleeve is a thermoplastic material, e.g., rubber sold under the mark KRATON by Shell Chemical Company of Houston, Tex. These materials are available as KRATON D and G 2000 series rubber. These materials are biocompatable and have less than optimum elastic characteristics, and are referred to herein as semi-elastic. When stretched, they initially return to a position of about 75 to about 90 percent of original configuration over a reasonable period of time.

The outer sleeve is preferably made of a natural or synthetic highly elastic rubber such as latex, silicone or other rubber with excellent elastic characteristics, and is referred to herein as elastic. A material with good elastic characteristics returns quickly from a stretched condition to its original un-stressed or un-stretched condition. A good elastic material also has a uniform elastic force over the range stretched and returns energy put into it. A good elastic rubber can stretch in the range from about five hundred to about eight hundred percent and return most of the energy as it returns to its original position. Natural latex rubbers are a preferred material for the outer sleeve of tubular member 1026. However, certain other rubbers such as silicone rubber would also be suitable.

The pump 1010 may include a sensor to measure flow rate, pressure, liquid volume, and temperature among other characteristics. Multiple sensors may also be used throughout the interior. These sensors may be configured to communicate wirelessly via Wi-Fi, Bluetooth, and other wireless communication protocols as known in the art to a readout or other device (not shown) such as a controller. Of course, the sensors may be hardwired to communicate directly with a readout or other internal or external device.

Figure 13:
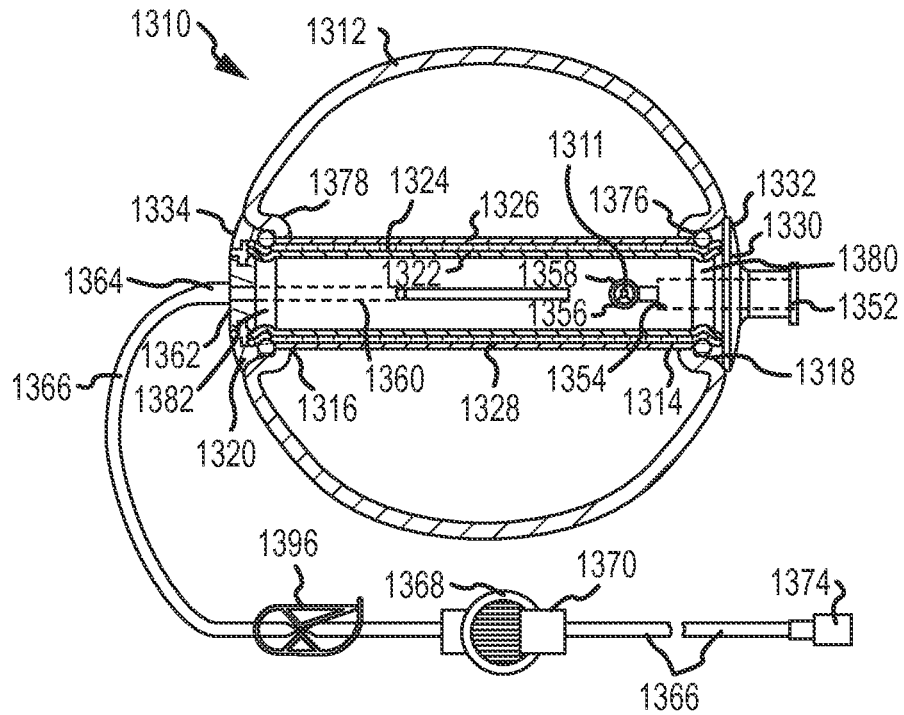
FIG. 13 illustrates a cross-sectional view of an infusion pump in a collapsed configuration.
Figure 14:
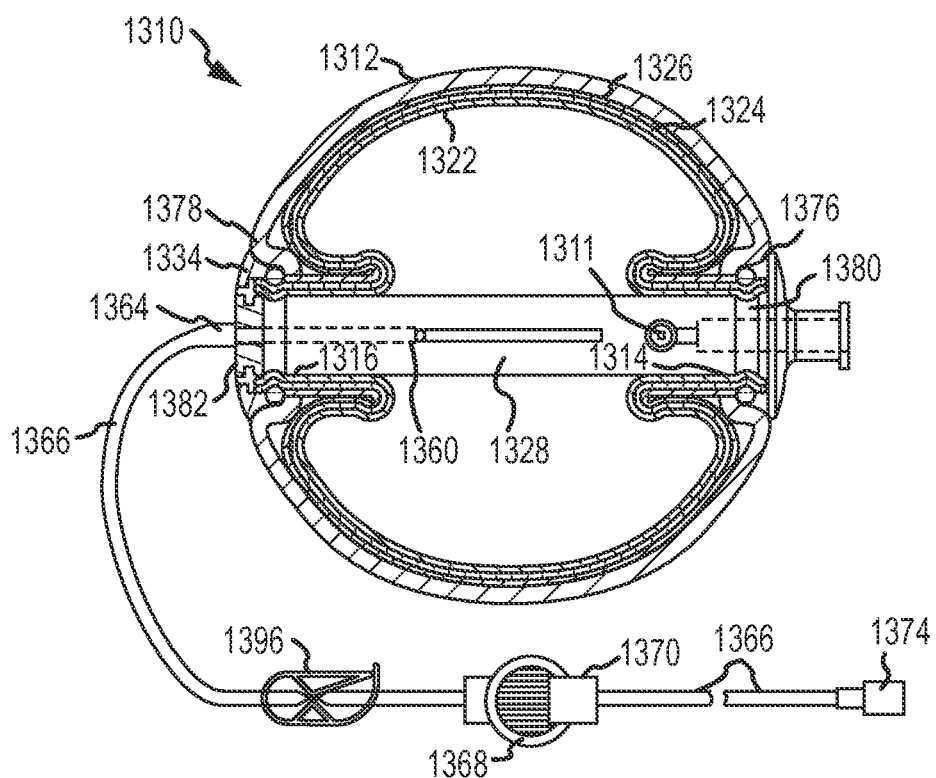
FIG. 14 illustrates a cross-sectional view of the infusion pump of FIG. 13 in the inflated configuration.

Still another embodiment of system includes a pump 110 as described in U.S. Pat. No. 5,080,652, which is incorporated by reference in its entirety. FIGS. 13 and 14 are directed toward a pump generally depicted as reference number 1310. The pump 1310 is separate from the charging or filler pump. Moreover, it may be filled by any suitable means, such as a syringe or any other pressurizing devices or methods. The housing 1312 has a substantially spherical configuration and is provided with coaxial, or more particularly aligned bores or ports 1314 and 1316, in which is mounted an inflatable bladder assembly. The housing 1312 may be made of unitary construction, such as by blow molding, or may be of two identical half shells assembled. The ports are formed in axial recesses 1318 and 1320. The inflatable bladder assembly includes a first or inner elongated semi-elastic sleeve 1322, and a pair of outer elongated latex rubber elastic sleeves 1324 and 1326 mounted on an elongated central cylindrical support member 1328. The inner sleeve 1322 is preferably made of a drug compatibility rubber with low leach characteristics that meets USP class 6 testing standards.

A rubber material for the inner sleeve 1322 is a class of thermoplastic rubber, e.g., sold under the mark KRATON by Shell Chemical Company of Houston, Tex. These materials are available as KRATON D and G 2000 series rubber, and have FDA status for use in certain applications or ingredients of articles for food contact. These materials have less than optimum elastic characteristics, and are referred to herein as semi-elastic. When stretched, they return to a position of about 75 to about 90 percent of original configuration.

The outer sleeves 1324 and 1326 are preferably made of a natural latex rubber with excellent elastic characteristics. A material with good elastic characteristics returns from a stretched condition to its original un-stressed or stretched condition. A good elastic material also has a uniform elastic force over the range stretched. Natural latex rubbers are the preferred material for the outer sleeves membranes 1324 and 1326.

The central support member 1328 is preferably of a generally elongated cylindrical configuration, with an annular radially extending retaining flange 1330 on one end for engaging a shoulder 1332 on the housing 1312. The opposite end of the support member 1328 includes a bayonet type coupling with a retaining nut 1334. The central support member may be constructed of any suitable pharmaceutically compatible material, such as metals, plastics, glass, etc.

The support member 1328 includes an inlet port 1352 communicating by way of a passage 1354, including a one-way valve 1356, 1358 with the interior of the membrane or sleeve 1322. Any suitable check valve may be used to permit uncoupling of the filling unit without leakage of fluid from the pressurized bladder. The check valve includes a cross through bore 1356 communicating with the end of passage 1354, and in which is slip fitted an elastic tube 1358, which may be of a suitable rubber such as silicone. The tube 1358 covers the end of passage 1354 to prevent back flow from inside the bladder formed by sleeve 1322. The tube 1358 collapses in response to higher pressure in passage 1354 enabling flow of liquid into sleeve 1322.

A sensor 1311 before the valve is configured to measure flow rate, pressure, liquid volume, and temperature among other characteristics. Multiple sensors may also be used throughout the interior. These sensors may be configured to communicate wirelessly via Wi-Fi, Bluetooth, and other wireless communication protocols as known in the art to a readout or other device (not shown) such as a controller. Of course, the sensors may be hardwired to communicate directly with a readout or other internal or external device. The sensors may be configured to communicate with the flow control device 1370, e.g., a feed-back loop as known in the art.

An outlet passage 1360 in support member 1328 communicates via an outlet port 1362 and suitable coupling assembly 1364, with an outlet or intravenous feeding line including, e.g., a two-part tube 1366, which includes a filter 1368, and may include flow control device 1370 and a male luer lock adaptor. The outlet line may be controlled by a suitable valve assembly (not shown) or preferably by the well known type clamp known as a clamp 1396. The luer lock 1374 has a valve that closes the outlet port when the feeding line is uncoupled therefrom. The coupling is effective to open the outlet valve when coupled to the outlet fitting. The delivery tubes 1366 may be selected in size and length to aid in maintaining a predetermined pressure and flow rate. The luer lock is configured to attach to a catheter, e.g., as shown in FIG. 1.

The elastic sleeves 1324 and 1326 are mounted over the sleeve 1322. Sleeves 1324 and/or 1326 may be stretched radially when in position over sleeve 1322, e.g. 1324 is stretched radially over 1322, with 1326 slip fit over the assemblies of 1322 and 1324. The outer bladder 1326 slips radially over the assembly of 1322 and 1324. The composite assembly of 1322, 1324, 1326 is slideably engaged with a slip fit over the mandrel or support member 1328. Radial stretching of the bladder 1324 compensates for material 1322's less than perfect elasticity. More specifically, the wall thickness and amount of stretch of bladder 1324 are selected to just compensate for bladder 1322's material less than perfect elasticity. The initial strain conditions and bladder wall thicknesses are also chosen to minimize the non-linearity exhibited in a bladder's stress versus strain.

It is well known that a single bladder infusion device constrained at both ends exhibits a highly non-linear stress versus strain relationship. This causes a time varying flow characteristic. The inner bladder is chemically inert and the outer bladder is elastic. The structure and method for maintaining constant flow versus time while the device is infusing by radially stretching an intermediate bladder over the inner bladder.

The inner semi-elastic drug compatible tube or membrane 1322 is mounted on the cylindrical support member 1328, preferably in a slightly snug but un-stretched radial fit, and essentially relaxed elongated or non-stretched longitudinal fit. The inner sleeve 1322 preferably has what shall be called a slip fit on the support member. This slip fit is preferably with a clearance on the order of about one-thousandths of an inch of the sleeve on the support. This provides a non-stretched fit, with essentially zero volume of the pressure chamber when in the non-stretched or totally relaxed state or mode.

The elastic sleeves 1324 and 1326 are respectively stretch fit and snug fit radially over the inner semi-elastic sleeve 1322. The intermediate sleeve 1324 is radially stretched up to about five percent over the inner sleeve 1322 for compressing it. The outer sleeve 1326 is slip fitted over the intermediate sleeve 1324. All of these sleeves 1322, 1324, and 1326 are fitted over the support member 1328 and clamped at the ends with a pair of O-rings 1376 and 1378. These O-rings 1376 and 1378 bias the ends of the multiple sleeves into annular grooves 1380 and 1382 in the outer surface of the member 1328. The O-rings 1376 and 1378 are held in place by the walls of the housing forming the recesses 1318 and 1320. The multiple sleeves when being filled tend to elongate and roll over the ends thereof as shown in FIG. 14. The support member 1328 is of a fixed length and holds the ends of the sleeves at a fixed position. The multiple thin sleeves easily roll over the ends, thereof as the bladder is made up of the multiple sleeves it fills and expands.

The pressure applied by the pressure chamber, formed by the multiple sleeves, will be substantially a function of the thickness of the wall of the elastic sleeve or sleeves. For example, a typical two to three (2-3) psi may be obtained by a wall thickness of about eighteen to twenty-thousandths (0.018-0.020) of an inch. In order to obtain higher pressure with superior uniformity, a multi-layered sleeve configuration as described hereinabove has been found to be preferred.

As illustrated in FIG. 13, a plurality of sleeves (three illustrated) 1322, 1326 and 1324 are slip fitted (non-stretched) on the support member. The inner sleeve 1322 is slip fitted on the support member 1328, and a second sleeve 1324 is slightly stretch fitted over the first sleeve 1322. Thereafter, a third sleeve 1326 is slip fitted over the intermediate sleeve 1324. These are shown in the fully deflated position in FIG. 13 and in the fully inflated condition in FIG. 14, showing the fold or roll over the ends. These multiple layers have been found to be superior to the use of thicker membranes or sleeves to obtain higher and uniform pressures. The use of multiple layers also enables the use of a semi-elastic substantially chemically (medically) inert inner membrane or sleeve for contact with the infusible liquid. The multiple sleeves will roll or fold over at the ends, as illustrated in FIG. 14. Thus, to increase the pressure, additional sleeves of substantially the same thickness are used.

When being filled, the elastic multi sleeve membrane has a tendency to elongate, but expands into a spherical configuration. The elongation is accommodated in this pump configuration by an accordion effect at the ends of the bladder, as shown in FIG. 14, wherein the bladder rolls over the ends thereof and outward along the support member 1328 as it expands outward to fill the housing 1312. The accommodation of the elastic membrane in the spherical configuration enables it to expand and contract in its natural fashion, and to maintain a substantially constant pressure and thereby flow rate over the intravenous injection period.

The layered or multiple sleeve configurations have been found to better accommodate the accordion fold and maintain a more uniform pressure than a thicker sleeve. The tubular elastic sleeve membranes are selected and mounted on the support member in a manner that enables them to roll or fold over at the ends when being filled.

In operation, an assembled infuser pump unit is selected, and the inlet port 1352 is secured to a source of fluid under pressure. As fluid is being introduced into the inlet, the valve 1358 collapses as fluid flows into the inner sleeve or membrane 1322. As the reservoir or bladder formed by the sleeves begins to fill, it expands and attempts to elongate. The ends of the sleeves begin to fold and roll over the ends thereof as in FIG. 14. The bladder forms a substantially spherical shape as its natural form of expansion. The roll at the ends accommodates this expansion and aids in maintaining a substantially constant pressure over the range of infusion.

As the bladder deflates, the outer elastic membranes force the inner semi-elastic membrane back to substantially its original position. This helps to evacuate the entire volume of fluid. It also will be appreciated that any form of pressurized filling apparatus may be used.

Figure 2A:
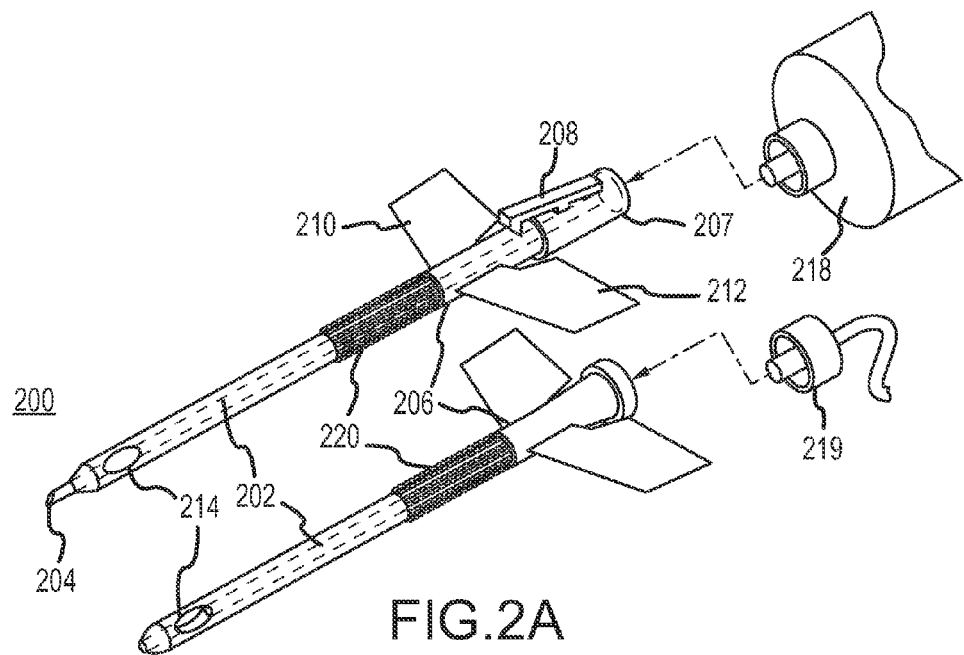
FIG. 2A illustrates a perspective view of a continuous anesthesia nerve conduction apparatus according to another embodiment of the invention.
Figure 2B:
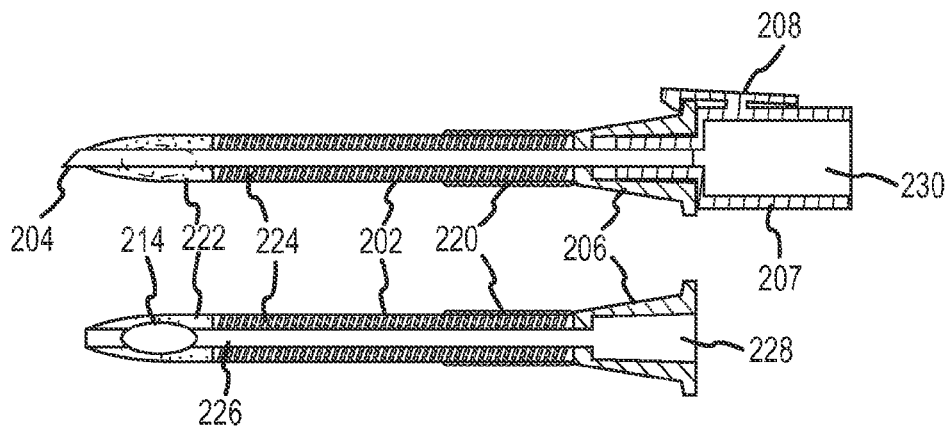
FIG. 2B illustrates a cross-sectional view of the continuous anesthesia nerve conduction apparatus shown in FIG. 2A.

FIG. 2A illustrates a perspective view of a continuous anesthesia nerve conduction apparatus according to another embodiment of the invention. FIG. 2B illustrates a cross-sectional view of the continuous anesthesia nerve conduction apparatus shown in FIG. 2A.

Referring to FIGS. 2A-2B, a continuous anesthesia nerve conduction apparatus is generally depicted with reference to number 200. The apparatus 200 includes a reinforced catheter 202 with and without the cannula 204. The beveled distal tip of the cannula 204 is shown to be protruding slightly from the distal tip of the catheter 202. The tip may also be curved. The proximal portion of the catheter 202 includes winged hub 206. The cannula 204 includes a hub 207 configured to abut and engage with the winged hub 206 via a locking mechanism 208. The wings 210, 212 optionally include an adhesive configured to attach to a patient. Optionally, the wings may also include a warning label configured to indicate and distinguish the type of catheter, e.g., anesthesia catheter versus an intravenous (IV) catheter. The catheter 202 optionally includes at least one port 214. The port 214 is configured to supply a pharmacological agent in at least a radial direction from a longitudinal axis of the catheter 202. That is, the port 214 permits the distribution of the infused pharmacological agent to the targeted nerve(s) 116 in a circumferential and linear pattern at the distal end. The port 214 may be configured to have small or large diameters, e.g., a diameter in the range from about 0.1 mm to about 2 mm or greater. There also may be a plurality of ports arranged circumferentially around the perimeter of the catheter, linearly done in axis of the catheter, and/or in another predetermined geometric pattern.

The proximal hub 207 of the cannula 204 is configured to accept a tip of a standard syringe 218. The hub 207 may include alignment marks as described herein, e.g., with reference to FIGS. 31A-33. The syringe 218 may be used to inject a pharmacologic agent, e.g., solution for hydro-dissection of tissue surrounding to the targeted nerve(s) 106 during catheter placement. Once in place adjacent to the targeted nerve(s) 106, the lock 208 is disengaged, the cannula 204 is withdrawn, and the catheter 202 is positioned to provide continuous nerve block.

The catheter hub 206 is further configured to accept a connector 219 on the end of the connecting tube 112. The connecting tube 112 is coupled to an infusion pump on the opposite end. A frictional region 220, e.g., pebbled region, is optionally added to a proximal portion of the catheter 202. The frictional region 220 is configured to aid in sealing an insertion site in the tissue, minimize leakage of contrast and/or pharmacological agent, and minimize movement of the catheter 202. The frictional region 220 may include an adhesive material including a bioresorable material and non-bioresorable material. Alternatively, instead of or in combination with the friction material 220 the proximal portion may have an enlarged diameter to further aid in sealing the insertion site. The enlarged diameter may be greater than the diameter of the rest such that the diameter is about 2% to about 15% greater than the diameter of the rest of the catheter. The orientation and the location of the catheter 202 and its lateral port can be monitored through the use of markers, e.g., radiopaque, echogenic, combinations of the same, and the like, via visualization techniques.

Referring now to FIG. 2B, the distal portion of the catheter 202 includes an echogenic region 222 including echogenic material to aid with ultrasound visualization of a distal tip of the catheter 202. The catheter 202 includes a lumen 226 extending from a proximal end to a distal end. The hub 206 also includes a lumen 228 in communication with the lumen 226. Finally, the cannula 204 and hub 207 of the cannula includes a lumen 230 extending from a proximal end to a distal end. The lumens 226, 228, and 230 are arranged to form one continuous lumen for administering a pharmacological agent or other medical device. The other medical device may include a balloon, active visualization device (imaging probe), surgical instrument, and the like. A reinforcement material 224, e.g., axial stays, metal and the other reinforcement material may be used for reinforcement of the catheter to minimize kinking or bending when desired. That is, the material 224 is embedded in a body of the catheter 202 to provide enhanced rigidity, thereby preventing bunching and kinking of the catheter 202. The catheter 202 may also be configured with various rigidities along a longitudinal axis of the catheter, e.g., the proximal portion may be stiffer than the distal portion and vice versa. Optionally, an anti-restrictive member or supplemental catheter may be used to further prevent kinking as described herein, e.g., with reference to FIGS. 37A-37G.

Figure 3A:
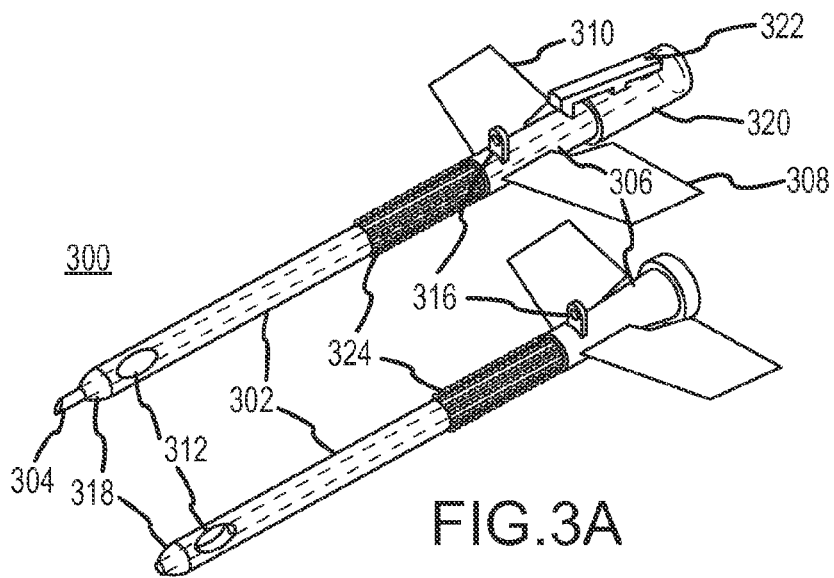
FIG. 3A illustrates a perspective view of a continuous anesthesia nerve conduction apparatus according to another embodiment of the invention.
Figure 3B:
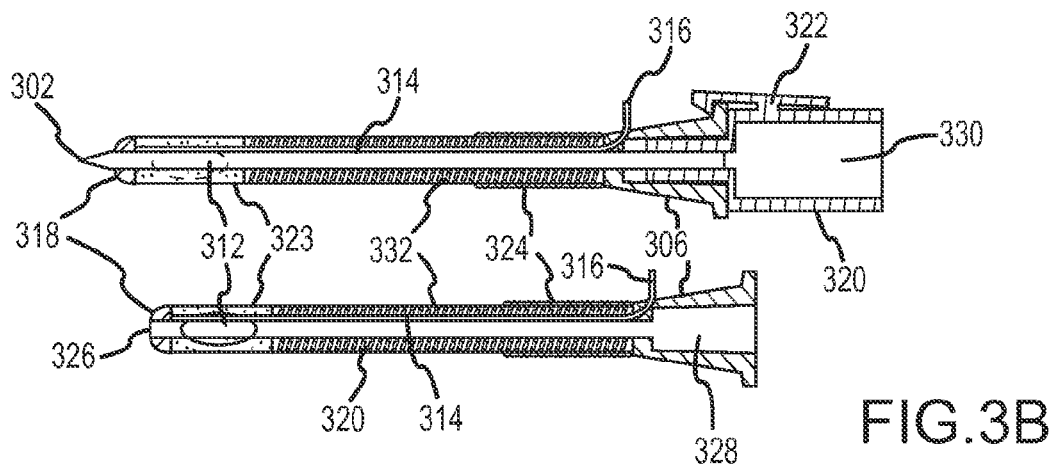
FIG. 3B illustrates a cross-sectional view of the continuous anesthesia nerve conduction apparatus shown in FIG. 3A.
Figure 3C:
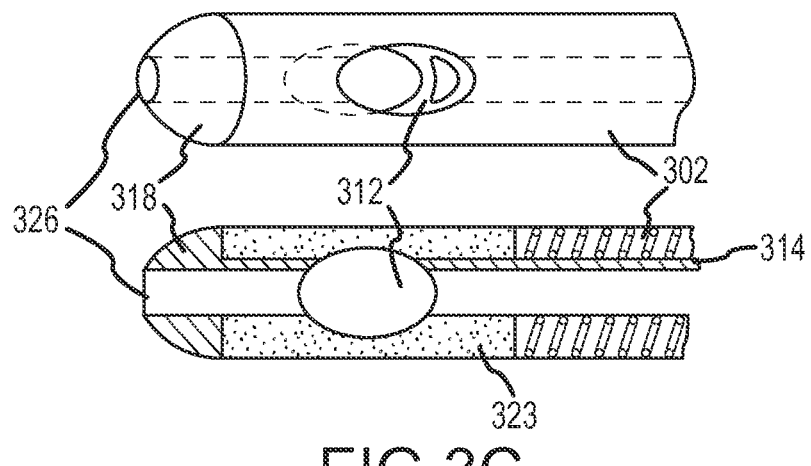
FIG. 3C illustrates an enlarged view of the distal section of the conduction apparatus according to FIG. 3A.

FIG. 3A illustrates a perspective view of the continuous anesthesia nerve conduction apparatus according to another embodiment of the invention. FIG. 3B illustrates a cross-section view of the continuous anesthesia nerve conduction apparatus shown in FIG. 3A. FIG. 3C illustrates an enlarged view of the distal section of the apparatus shown in FIG. 3A.

Referring to FIGS. 3A-3C, a continuous anesthesia nerve conduction apparatus is generally depicted with reference to number 300. The apparatus 300 includes a reinforced catheter 302 with and without a cannula 304. The beveled distal tip of the cannula 304 is shown to be protruding slightly from the distal tip of the catheter 302. The proximal portion of the catheter 302 includes a winged hub 306. Wings 308, 310 optionally include an adhesive configured to attach to a patient. The catheter 302 optionally includes at least one port 312. The port 312 is configured to supply a pharmacological agent, e.g., contrast, medicine, or the like, in at least a radial direction from a longitudinal axis of the catheter 302. That is, the ports 312 permit the distribution of the infused pharmacological agent to the targeted nerve(s) 116 in a circumferential and/or linear pattern.

The apparatus 300 further includes an embedded conductive element 314 and a conductive 316 tab. The conductive element 314 is configured to transmit electrical activity used to activate a nerve, e.g., dc current, voltage, ac current, square wave, or combination, to a distal portion of the catheter 302 and cannula 304. In a preferred embodiment, the electrical activity is generated by a nerve stimulator generator (not shown), e.g., Stimuplex® HNS11 Peripheral Nerve Stimulator by B. Braun, Stimuplex Dig RC by B. Braun, MultiStim VARIO by Pajunk, and EzStim® stimulator by Life-Tech International. In a preferred embodiment, the embedded conductive element 314 is an embedded wire.

An electrode cap 318 is affixed to a distal end of the catheter 302. The electrode cap 318 is coupled to the embedded wire 314 and is configured to allow for peripheral nerve (s) simultaneous stimulation via the cannula 304 and the catheter 302. The embedded wire 314 is within the body of the catheter and connects the electrode cap to the proximal electrode connector 316 on the catheter hub 306.

In this embodiment, an electrical signal is to be introduced via a peripheral nerve stimulator connected to the proximal electrode connector 316 and propagated to the electrode cap 318 on the distal tip of the catheter 302 with an internal conductive wire 314. The electrode cap 318 provides transmission to a distal tip of a cannula 304. The catheter body 302 acts as an insulator for the rest of the cannula 304. Therefore, transmission of a signal with a single connection may be supplied via a distal tip of the cannula 304, the electrode cap 318 or singly via the electrode cap 318 by retracting the cannula 304 proximal of the electrode cap 318. Optionally, the outer surface of the electrode cap 318 may be insulated with an insulated material. In this embodiment, when an electrical signal is applied to the outer surface of the electrode cap 318 does not transmit an electrical signal as it is insulated.

A proximal hub 320 of the cannula 304 is further configured to accept a tip of a standard syringe (not shown). The proximal hub 320 includes a connector 322 for releasably coupling cannula hub 320 to the catheter hub 306. The catheter hub 306 is further configured to accept a connector (not shown) on an end of the connecting tube 112. The connecting tube 112 is coupled to an infusion pump on the opposite end (FIG. 1, 110). A frictional region 324, e.g., at least a partially coarse region, is optionally added to a proximal portion of the catheter 302. The frictional region 324 is configured to aid in sealing an insertion site in the tissue, minimize leakage of contrast and/or pharmacological agent, and minimize movement of the catheter 302. Moreover, the diameter at the frictional region may also be enlarged as described herein.

A distal portion of the catheter 302 includes an echogenic region 323 including echogenic material to aid with ultrasound visualization of a distal tip of the catheter 302. The echogenic material may include metallic flakes, reflective flakes derived from titanium, stainless steel, copper or other similarly inert metals or alloys that reflect the sound waves generated by the ultrasound probe. The catheter 302 includes a lumen 326 extending from a proximal end to a distal end. The hub 306 also includes a lumen 328 in communication with the lumen 326. Finally, the cannula hub 320 includes a lumen 330 extending from a proximal end to a distal end. The lumens 326, 328, and 330 are arranged to form one continuous lumen for administering a pharmacological agent or other medical device. The other medical device may include a balloon, active visualization device (imaging probe), surgical instrument, and the like.

A reinforcement material 332, e.g., axial stays, metal and the like as known in the art, is added to a body of the catheter 302 to provide enhanced rigidity, thereby preventing bunching and kinking of the catheter 302. A plurality of reinforcement material 332 may be used. The catheter 302 may be configured with various rigidities along a longitudinal axis of the catheter, e.g., the proximal portion may be stiffer than the distal portion.

Figure 4:
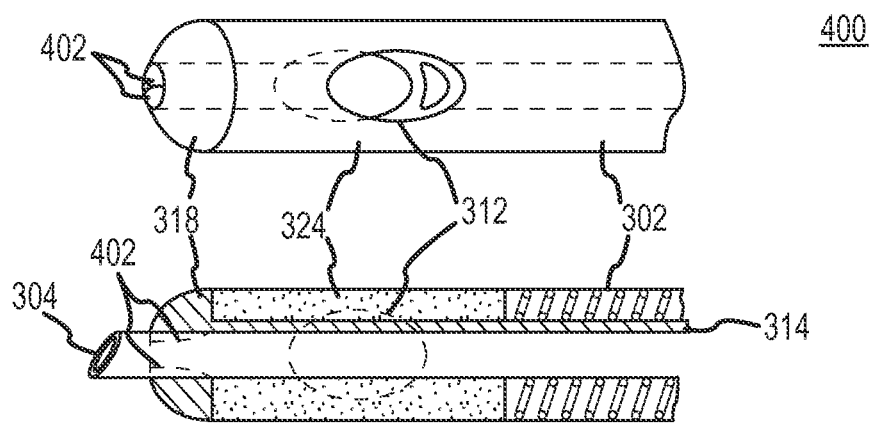
FIG. 4 illustrates an enlarged view of a distal section of a conduction apparatus according to another embodiment of the invention.

FIG. 4 illustrates an enlarged view of a distal section of the conduction apparatus according to yet another embodiment of the invention.

Referring to FIG. 4, a distal tip of the apparatus is generally referred to as reference number 400. The rest of the apparatus (not shown) is similar to the catheter described in FIGS. 3A-3C and will not be described further. In this embodiment, the distal tip of the catheter 302 includes a retractable flap 402. The distal port of the catheter is patent while the introducing cannula 304 is inserted through the lumen of the catheter 302, but the retractable flap 402 is configured to deploy once the cannula 302 is withdrawn; that is, retractable flap 402 is configured to move from a closed position to an open position as shown. In a closed position and when the catheter is in use, only the side port 312 is utilized to deliver pharmacological agent.

Figure 5:
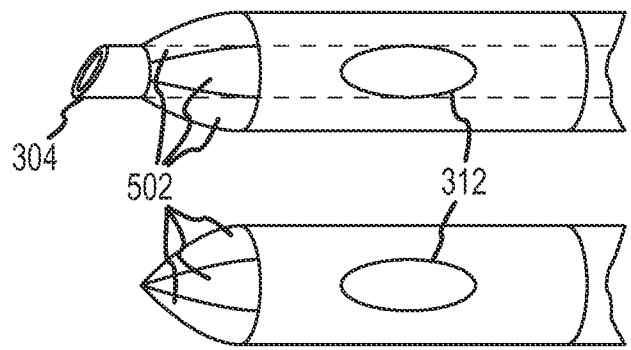
FIG. 5 illustrates an enlarged view of a distal section of a conduction apparatus according to another embodiment of the invention.

FIG. 5 illustrates an enlarged view of a distal section of the conduction apparatus according to yet another embodiment of the invention.

Referring to FIG. 5, a distal tip of the apparatus is generally referred to as reference number 500. The rest of the apparatus (not shown) is similar to the catheter described in FIGS. 3A-3C and will not be described further. In this embodiment, the distal tip of the catheter 302 includes a plurality of retractable flaps 502 that are configured in an open position and closed position by movement of a cannula 304. More specifically, the distal port of the catheter is patent while the introducing cannula 304 is inserted through the lumen of the catheter 302, but the retractable flap 502 is configured to deploy once the cannula 304 is withdrawn; that is, retractable flap 502 is configured to move from an open position to a closed position. In a closed position and when the catheter is in use, only the side port 312 is utilized to deliver pharmacological agent.

Figure 6A:
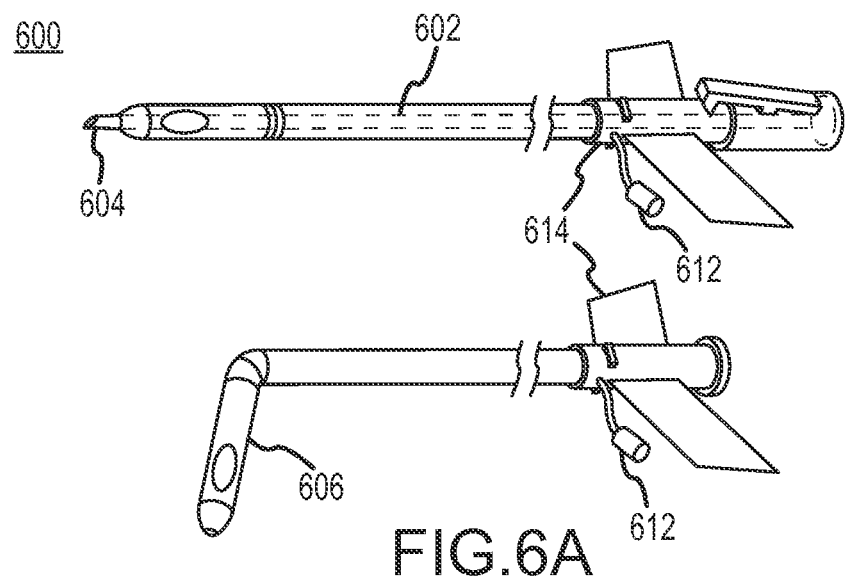
FIG. 6A illustrates a perspective view of a continuous anesthesia nerve conduction apparatus according to another embodiment of the invention.
Figure 6B:
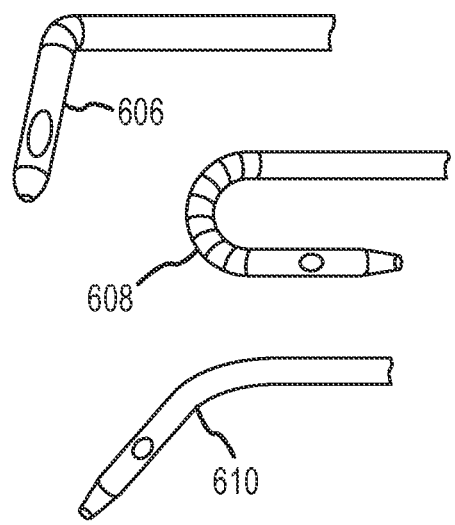
FIG. 6B illustrates an enlarged view of a distal portion of the continuous anesthesia nerve conduction apparatus of FIG. 6A in various configurations.

FIG. 6A illustrates a perspective view of the continuous anesthesia nerve conduction apparatus according to another embodiment of the invention. FIG. 6B illustrates an enlarged view of a distal section of the continuous anesthesia nerve conduction apparatus according of FIG. 6A in various configurations.

Referring to FIGS. 6A-6B, a continuous anesthesia nerve conduction apparatus is generally depicted with reference to number 600. The apparatus 600 is similar to the apparatus described with reference to FIG. 3A-3C except for the distal portion of the reinforced catheter 602. The distal portion of the reinforced catheter 602 with a preformed shape, controllable shape or resilient shape. In one embodiment, when a cannula 604 is inserted through the lumen of the reinforced catheter 602, the distal tip of the catheter is straightened by the cannula 604, but when the cannula 604 is withdrawn, the distal tip takes its preformed shape. The shape may be an "L" shape as noted with reference to element 606, "U" shape as noted with reference to element 608, or curved as in 610. The proximal electrode connector 612 is positioned on the side of the proximal catheter hub 614 so that the direction of the preformed distal tip of the catheter is corresponding with the electrode connector 612. Alternatively, the distal end portion of the catheter 602 may be controllable with a wire system (not shown) to various geometries, e.g., "L" shape, "U" shape, or curved shape. The various geometries allow the distal portion of the catheter to be closer to a desired nerve or nerve bundle thus permitting a better distribution on anesthetic solution while keeping more of the catheter in close proximity to the nerve(s).

Catheters as described herein may be constructed, in whole or in part, utilizing a variety of degradable materials, polymeric materials, synthetic or natural, and combinations thereof. Furthermore, the catheters may be composed such that the portion of the catheter that enters and remains in the patient is degradable, but the portion that remains substantially outside of the patient is not degradable. Furthermore, a break point may exist between the two materials. The break point may be configured to facilitate breaking.

In some embodiments, the catheters may be composed of multiple components that are mixed as a blend, such as a plasticized system, and/or as a microphase immiscible system. If suitable reactive groups are introduced into the formed catheters, what is commonly known as a thermoset, or chemically cross-linked system can be generated under appropriate curing conditions. The formed catheters can also be composed in the form of a laminate or a fibrous reinforced composite. Of course, the properties of the selected composition, e.g., molecular weight, glass transition temperature(s), crystallinity, and/or the extent of cross-linking will dictate the desired properties of the catheters. The catheters may also be coated with a variety of therapeutic agents such as pain, antibacterial, antimicrobial or anti-inflammatory coatings, drug coatings, and the like. The catheters may also be composed of and/or coated with anti-microbial materials and micro surfaces such as silver nanoparticles, for example the catheter may be impregnated with silver nanoparticles, to provide antibacterial properties.

Figure 15A:
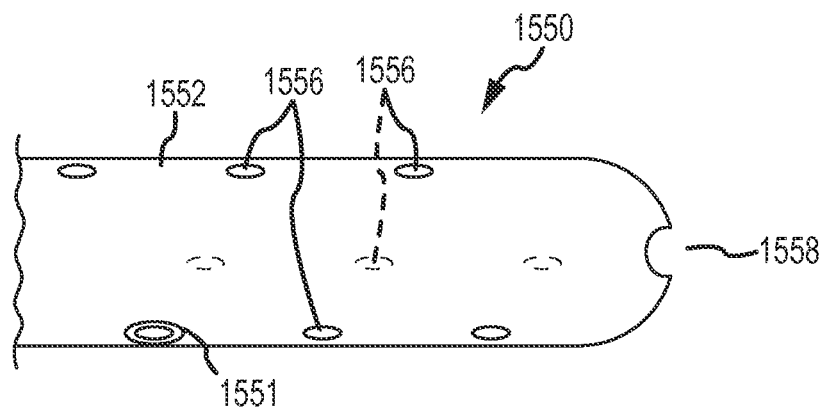
FIG. 15A illustrates a distal portion of a catheter according to another embodiment of the invention.
Figure 15B:
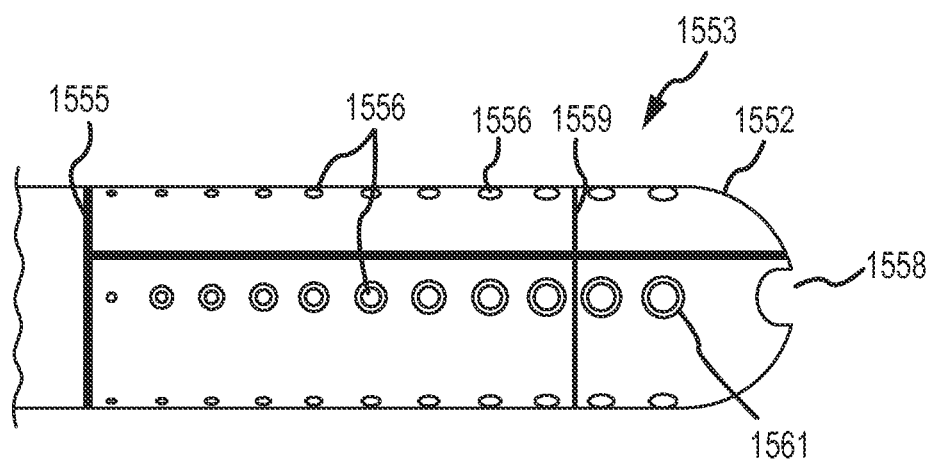
FIG. 15B illustrates a distal portion of a catheter according to another embodiment of the invention.

FIG. 15A illustrates an embodiment of a catheter tip. FIG. 15B illustrates another embodiment of a catheter tip;

Referring to FIGS. 15A-15B, it is shown that embodiments of catheters may be used with ports as described in U.S. Pat. No. 7,004,923, which is incorporated in its entirety by reference, may be used. The catheter is generally described herein and in this embodiment includes a distal portion as shown via reference number 1550. The distal portion 1550 includes an outer tube 1552. A plurality of fluid ports 1556 are provided within the tube 1552, preferably throughout the entire circumference thereof. The portion of tube 1552 that includes the ports 1556 defines the infusion section of catheter 1550. An access for the cannula is provided within the distal tip 1558 of the tube 1552. Moreover, the distal end portion may a preformed shape as described herein.

The tube 1552 may be formed from any of a variety of suitable materials, giving due consideration to the goals of non-reactivity to anatomical systems, such as nylon, polyimide, Teflon, biodegradable materials previously discussed and other materials known to those skilled in the art, giving due consideration to the goals of non-reactivity to anatomical systems, flexibility, light-weight, strength, smoothness, and safety. In a preferred configuration, the tube 1552 is preferably a 20 gauge catheter tube, having inside and outside diameters of 0.019 inches and 0.031 inches, respectively. The ports 1556 of tube 1552 are preferably about 0.015 inches in diameter and provided at equally spaced axial positions along the tube 1552. The holes 1556 are preferably arranged so that every hole is angularly displaced about 120° relative to the longitudinal axis of the tube 1552, from the angular location of the previous hole. Other angular displacements are possible, e.g., in a range from about 5° to about 180° relative to the longitudinal axis of the tube.

The axial separation between adjacent ports 1556 is preferably within the range from about 0.1 inches to 0.3 inches, and more preferably about 3/16 inch. Also, the infusion section can have any desirable length but is preferably about 0.5 to 20 inches long, and more preferably about 10 inches long. This configuration results in a thorough, uniform delivery of fluid throughout a generally linear segment of the wound area. Of course, the ports 1556 may be provided in any of a variety of alternative arrangements. In addition, each port 1556 or only a portion of the ports may be surrounded with a marker 1551 to permit visualization, e.g., radiopaque, echogenic, and combinations of the same.

FIG. 15B illustrates a catheter which is generally described herein and in this embodiment includes a distal portion as shown via reference number 1553. This embodiment is better suited for relatively high flow rate delivery of fluid to a region within an anatomical system. Catheter 1550 includes a tube 1552 having a plurality of ports 1556 of increasing size. In particular, the more distal ports are larger in diameter than the more proximal ports. The position of the ports 1556 on the tube 1552 defines the length of the infusion section of the catheter 1550. The infusion section can have any desired length. The proximal end of catheter 1550 is connected to a fluid supply, and a guidewire and/or guidewire lumen may also be provided for aiding in the insertion of catheter 1550 into the anatomy. One or more marking lines 1555, 1559 and markers 1561 may surround a port 1556 to permit visualization, e.g., radiopaque, echogenic, and combinations of the same.

As discussed above, for high or low pressure fluid delivery, ports nearer to the distal end of a catheter tube generally have increased flow resistance compared to ports nearer to the proximal end of the tube. Also, the fluid flowing through the more distal holes experiences a greater pressure drop. Consequently, there is generally a greater flow rate of fluid through the more proximal holes, resulting in non-uniform fluid delivery. In contrast, catheter 1550 advantageously provides substantially uniform fluid delivery through substantially all of the ports 1556, under relatively high flow rate conditions. This is because the larger size of the more distal holes compensates for their increased flow resistance and pressure drop. In other words, since the more distal holes are larger than the more proximal holes, there is a greater flow rate through the more distal holes than there would be if they were the same size as the more proximal holes. Advantageously, the holes 1556 are provided in a gradually increasing size which results in substantially uniform fluid delivery. In addition, the ports 1556 may be sized so that they combine to form a flow-restricting orifice. Moreover, the distal end portion may a preformed shape as described herein.

Figure 16:
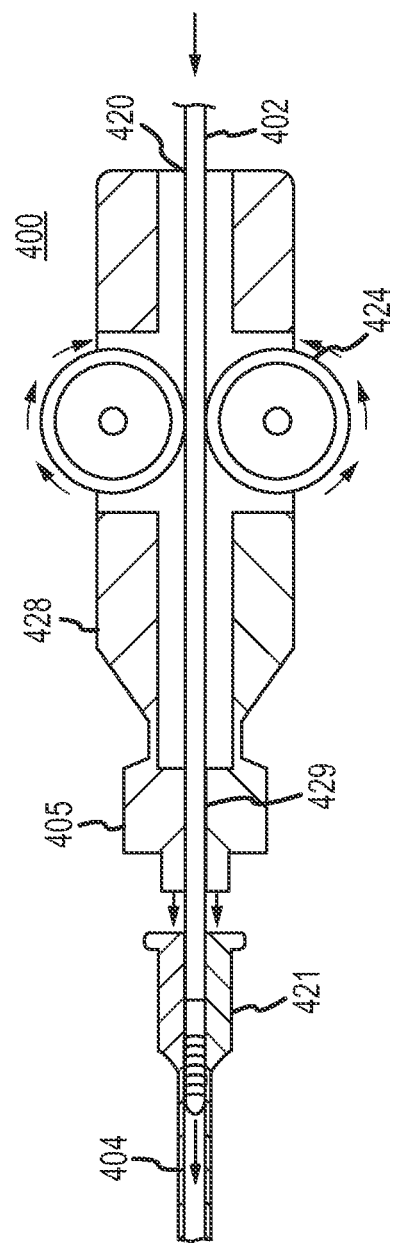
FIG. 16 illustrates a single handed catheter advancing device according to another embodiment of the invention.

FIG. 16 illustrates an embodiment of a single handed catheter advancing device.

Referring to FIG. 16, the invention is a single handed catheter advancing device and is generally depicted as reference number 400. The single handed device 400 allows a catheter to be advanced into a patient single handed. This device is not limited to only catheters described herein, but may be used with conventional needle over the catheter configurations. The device 400 includes a body 428 having free revolving rollers 424. The free revolving rollers 424 can be operated single handedly by the operator by placing the thumb of the operator on the free revolving rollers 424 and turning the rollers 424 which can insert or remove the catheter 402 depending upon the direction the rollers 424 are being turned. The catheter 402 is inserted through the catheter insertion opening 420 which is located at the end of the body 428. The free revolving rollers 424 advance the catheter 402 into the needle 404. The free revolving rollers 424 may include rubber grippers on the roller 424. The rubber grippers can be made of any suitable material, including but not limited to nylon, rubber, teflon, polyamide, polyfiline, other polymers and the like, or combinations thereof. The body 428 is also connected to a luer 405, such as a swivel male luer. The luer 405 can be connected to a needle hub 421, which is also connected to the needle 404 either permanently or temporarily. For example, the luer 405 may contain threads that may engage with threads on the needle hub 421. The needle hub 421 can disconnect from the luer 405. In addition, the luer 405 may be an integral portion of the body 428.

The device operates to advance the catheter 402 into the needle 404 with one hand, while leaving the other hand of the operator free to perform other tasks, such as attach and operate a nerve stimulator or use an ultrasound to locate a nerve bundle. The device may also be used with an ant-restriction member and/or supplemental catheter as described herein. The operator introduces the needle 404 to the patient. The single handed device 400 may be connected as the operator introduces the needle 404 to the patient, or it may be attached at a later time. Once the needle 404 is in place, a catheter 402 may be introduced into the hollow needle 404. The device 400 contains channel 429, which directs the catheter 402 introduced to the device through the opening 420 through the luer 405, into the needle hub 421 and eventually into the needle 404. The operator can control the advancement of the catheter 402 using the rollers 424 on the body 428. Once the catheter 402 is in place, the operator may remove the needle 404 and device 400 in a single motion by sliding the needle 402 attached to the device 400 over the catheter 402. Alternatively, the operator may remove the needle 402 and device 400 in two steps by first disconnecting the device 400 from the needle 404 at the needle hub 421, then removing the needle 404 from the patient, while leaving the catheter 402 in place. The catheter 402 may then be joined to an apparatus, such as an infusion pump.

Figure 17C:
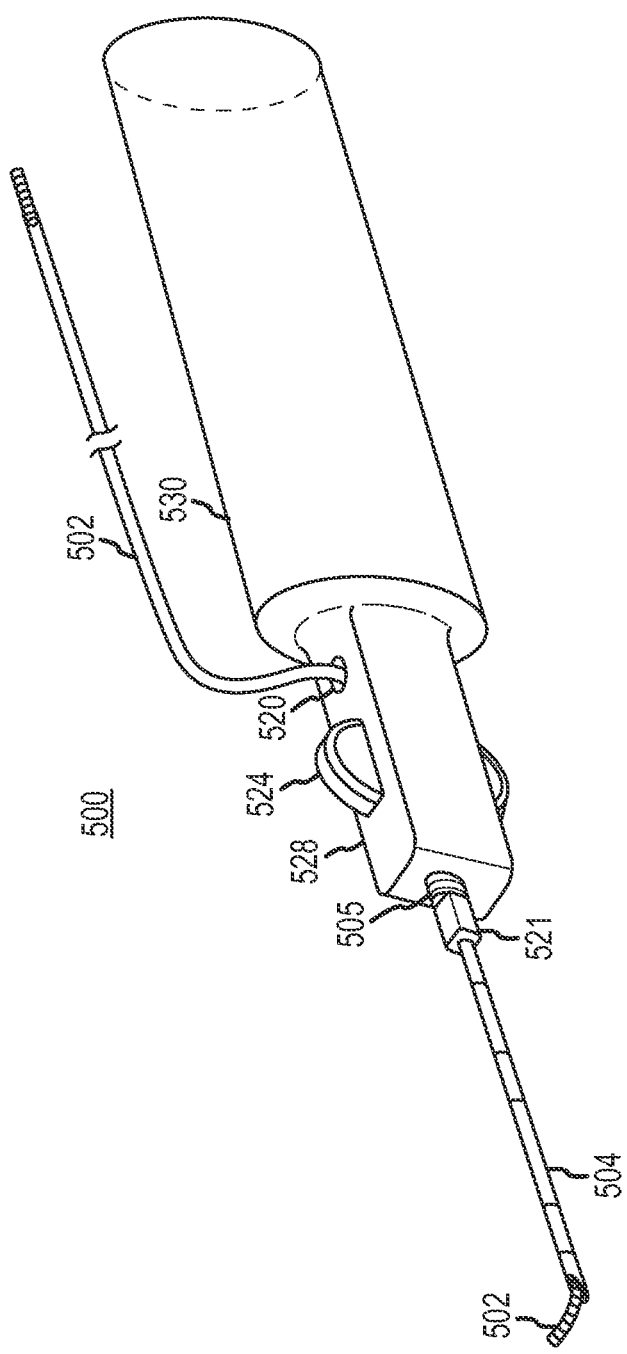
FIG. 17C illustrates a perspective view of a single handed catheter advancing device illustrated in FIG. 17A with a catheter.

FIG. 17A illustrates a single handed catheter advancing device according to another embodiment. FIG. 17B illustrates a perspective view of a single handed catheter advancing device illustrated in FIG. 17A. FIG. 17C illustrates a perspective view of a single handed catheter advancing device illustrated in FIG. 17A with a catheter;

As illustrated in FIGS. 17A-17C, the device is generally depicted as reference number 500. The device 500 includes a catheter insertion opening 520 located adjacent to one of the free revolving rollers 524 of the body 528 and used to advance the catheter 502 through a luer 505 and into a needle or cannula. A handle 530 may be permanently or temporarily attached to the body 528 using any suitable means. The handle 530 may be ergonomical and made of any suitable material. Furthermore, the handle 530 may include indents for fingers—in particular it may include a groove to receive a portion of the thumb of the user. The handle 530 may be tapered, may vary in length, and may vary in diameter or size. In an alternative embodiment, a catheter insertion opening 520 may be located anywhere on the body of the single handed catheter. By way of example, the catheter insertion opening 520 may be located near the end of the handle 530, which is similar to the configuration of FIG. 16. In this configuration, the opening 520 is aligned with a central-axis of the handle 530.

The body 528 is shown with the free revolving rollers 524 and is adjacent to the catheter insertion opening 520, which is located on the body 528 adjacent to the free revolving rollers 524. Luer 505 may be used to attach the device 500 to a needle, through the needle hub 521.

In one embodiment, the catheter 502 is advanced through the catheter insertion opening 520 of the body 528, which is adjacent to one of the free revolving rollers 524. The cannula or needle 504 is attached to the device 500 through the luer 505, which is connected to the needle hub 521. The catheter advances through the luer 505, through the needle hub 521, and into the needle 504.

Figure 18:
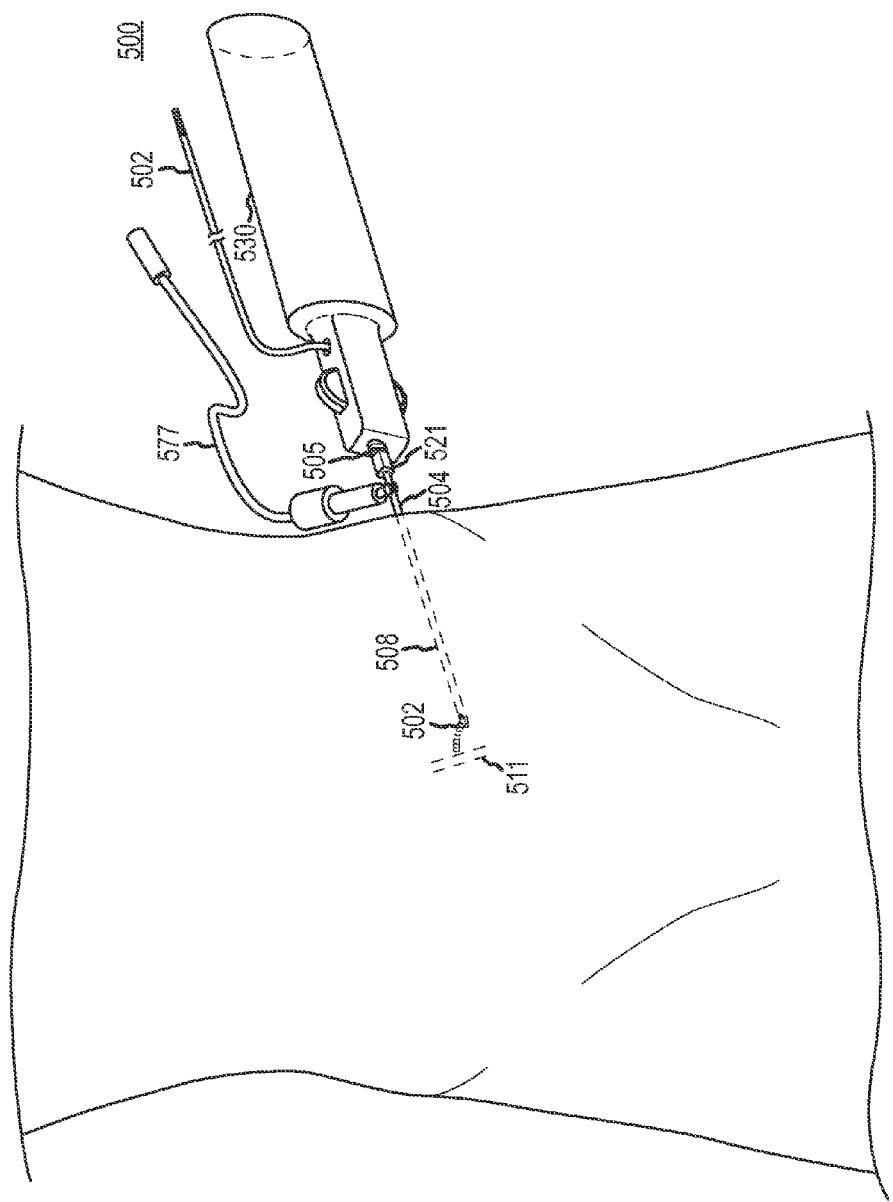
FIG. 18 illustrates the single handed catheter advancing device of FIG. 17C in use.

FIG. 18 illustrates an operational systematic view of the single handed catheter advancing device 500 as illustrated in FIG. 17C. The device 500 includes a needle 504 which remains external to the patient. The sheath 504 is inserted through the needle hub 521 and the needle 504. The needle hub 521 is connected to the device 500 through a luer 505.

Nerve(s) 511 lying in deep in tissue below the exterior surface of the patient are targeted to receive a pharmacological agent. A subcutaneous distal portion of the needle 508 is shown positioned in close proximity to the targeted nerve(s) 511, e.g., nerves of the brachial plexus. A nerve stimulator (not shown) may be used to stimulate the nerve(s) 511. A nerve stimulator conducting wire 577 is electrically coupled between a nerve stimulator (not shown) and needle 504 to provide the requisite single to the needle 504. Once the needle is in place, the catheter 502 may be advanced through the needle. The needle may be removed and the hub 521 disconnected from the luer 505.

Next, an infusion pump may be filled with a pharmacological agent, e.g., medication such as a nerve block, and the pump is connected to the apparatus. The pump can include ON-Q® C-bloc-Continuous Nerve Block System by I-Flow Corporation, PainPump 1, PainPump 2, PainPump 2 BlockAid by Stryker Corporation, and GoPump® or GoBlock® by Symbios and may be any of the embodiments previously explained and described with reference to FIGS. 7-14. Of course any described catheter herein may also be used with devices of FIGS. 15-18.

The devices of FIGS. 15-18 aid a user in single handedly advancing and retracting a catheter to a desired location, e.g., nerve location. Thereby, the user may use the other free hand to aid with visualization. These devices may be used with conventional catheter-through-needle systems. It is also noted that these devices are not required for single handed operation advancement, retraction of a catheter and/or cannula, but rather further aid a user in that regard.

Figure 19A:
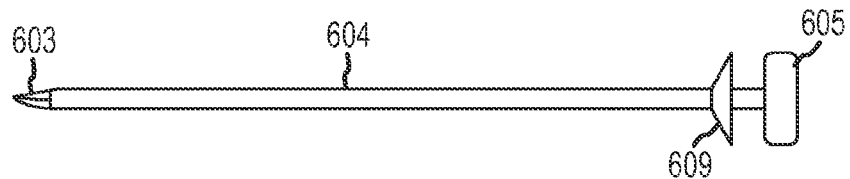
FIG. 19A illustrates an embodiment of a solid introducer according to another embodiment of the invention.
Figure 19B:
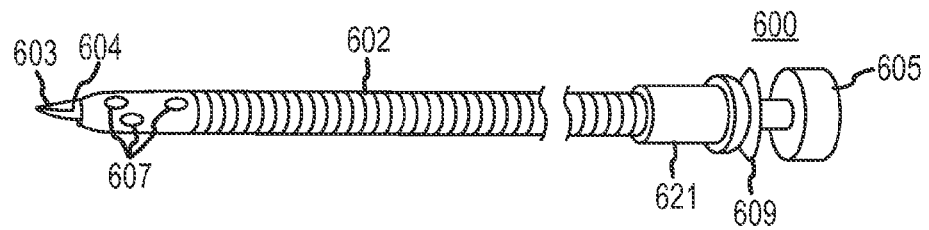
FIG. 19B illustrates a continuous anesthesia nerve conduction apparatus including solid introducer of FIG. 19A in a catheter according to another embodiment of the invention.

FIG. 19A illustrates an embodiment of a solid introducer. FIG. 19B illustrates the solid introducer of FIG. 19A in a catheter.

Referring to FIGS. 19A-19B, the solid introducer catheter system is generally depicted as reference number 600. The system includes a solid introducer 604. The solid introducer 604 may be used with the catheter 602 or other catheters described herein. The solid introducer 604 fits within the catheter 602. The catheter 602 may be a reinforced catheter and may include at least one or a plurality of ports 607 near the distal tip of the catheter 602. Ports as described anywhere herein, e.g., in FIGS. 15A-15B, may also be used.

On the proximal end of the catheter 602 is a catheter hub 621. The solid introducer 604 may also include an optional curved tip 603 which may be used as a cutting surface to insert the solid introducer catheter system 600 into the patient. The solid introducer 604 may include an optional stimulator connection site 609 wherein a stimulator (not shown) may be connected through the solid introducer 604. The optional stimulator connection site 609, when inserted into the catheter 602 may rest on the catheter hub 621 which controls the depth of insertion of the solid introducer 604 through the catheter 602 such that the distal tip 603 of the solid introducer 604 protrudes from the tip of the catheter 602. Furthermore, the stimulator connection site 609 is adjustable along the length of the solid introducer 604. Additionally, a needle hub 605 may be used by the operator to pull the solid introducer 604 from the patient once the catheter 602 is in place. Once the solid introducer 604 has been removed from the catheter 602, the catheter hub 621 may be used to connect the catheter 602 to the remaining system or other device.

Figure 20:
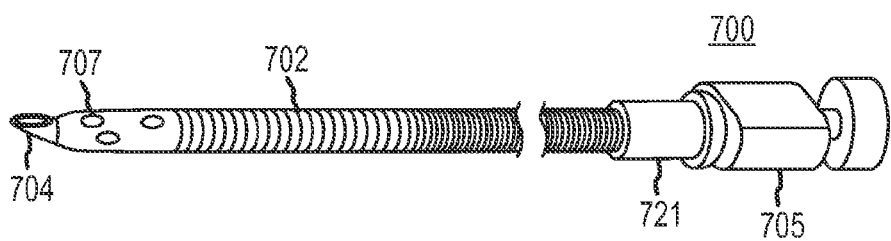
FIG. 20 illustrates a continuous anesthesia nerve conduction apparatus including a hollow introducer in a catheter according to another embodiment of the invention.

FIG. 20 illustrates another embodiment of the present invention, which is a hollow introducer catheter system 700. In this system, the introducer 704 is hollow. The hollow introducer 704 is advantageous because it allows a guidewire 734 to sit within the introducer 704 which sits inside of the catheter 702. The catheter 702 may be a tightly wound wire coil through the majority of the body of the catheter 702, but near the distal tip of the catheter 702 becomes a loosely wound wire which will allow for flexibility. The distal end of the catheter 702 may also include at least one or a plurality of ports 736. The introducer hub 705 rests upon the catheter hub 721, which controls the depth of the introducer 704 within the catheter 702. Once the introducer 704 has been removed, the catheter hub 721 may be used to connect the catheter 702 to the remaining system or other device.

Figure 21:
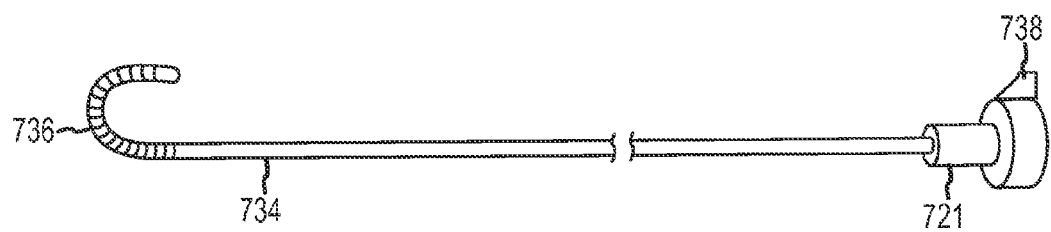
FIG. 21 illustrates an embodiment of a guidewire according to another embodiment of the invention.

FIG. 21 illustrates an embodiment of a guidewire.

Referring to FIG. 21, the guidewire 734 may be used with catheters as described herein. In one embodiment, the guidewire 734 is helpful for positioning the catheter 702 and/or stimulating the nerve bundle in the patient. Optionally, the guidewire 734 may be equipped with a flexible preformed tip 736 which allows for directional advancement of the catheter. The flexible preformed tip may be straightened out to pass through a needle or catheter, but will return to its preformed shape once it has exited the needle or catheter. In some embodiments, the position of the catheter follows the preformed shape of the guidewire once the guidewire is withdrawn. Near the guidewire hub 721, there is a directional tab 738 which corresponds to the direction and location of a flexible tip 736 on the guidewire 734. A stimulator (not shown) may also be attached to the directional tab 738. The guidewire 734 may be used either in the hollow introducer 704 or in the catheter 702.

Figure 22A:
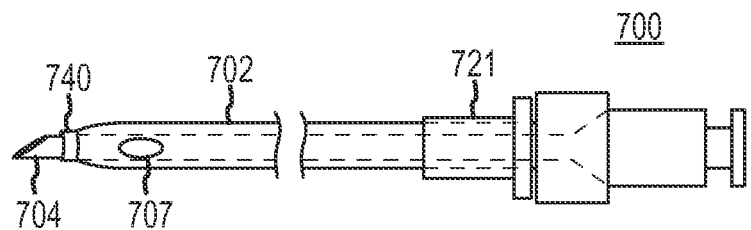
FIG. 22A illustrates a continuous anesthesia nerve conduction apparatus including a hollow introducer in a catheter with a sleeve according to another embodiment of the invention.
Figure 22B:
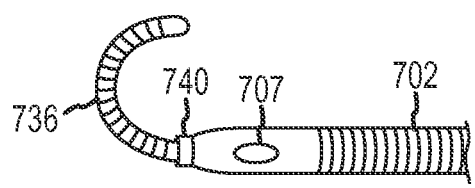
FIG. 22B illustrates a continuous anesthesia nerve conduction apparatus including a guidewire in a catheter with a sleeve according to another embodiment of the invention.

FIG. 22A illustrates another embodiment of a hollow introducer in a catheter with a sleeve. FIG. 22B illustrates another embodiment of a guidewire in a catheter with a sleeve.

Referring to FIGS. 22A and 22B, a sleeve 740 used in the catheter system 700 which allows for the reinsertion of an introducer 704 into the catheter 702 for repositioning of the catheter 702. That is, the sleeve will prevent tears in an external or internal surface of a catheter 702 upon reinsertion or repositioning of the catheter 702 when a cannula is required to reposition the catheter by advancing through tissue. The sleeve may also be utilized to prevent kinking of the catheter.

Figure 23:
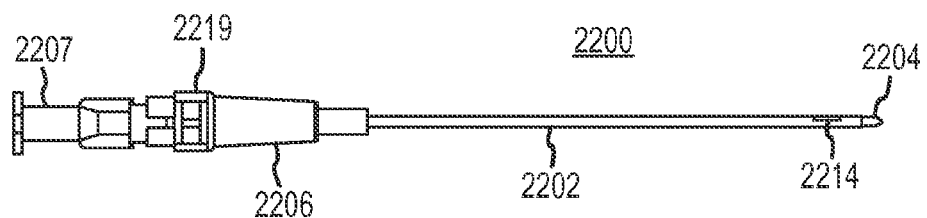
FIG. 23 illustrates a continuous anesthesia nerve conduction apparatus according to another embodiment of the invention.

FIG. 23 illustrates an embodiment of the continuous anesthesia nerve conduction apparatus. The apparatus is generally depicted as reference number 2200. The apparatus 2200 includes an introducer 2204, which may be a solid introducer or a hollow introducer, configured to fit within a catheter 2202 with at least one port 2214. An insert 2219 abuts and engages between the introducer end 2207 and the catheter hub 2206. The introducer 2204 slides into the catheter 2202, through the catheter hub 2206 and through the center of the insert 2219. The insert 2219 is configured, such that the user may access and connect a nerve stimulation device to the exposed segment of the introducer 2204 allowing for the introducer 2204 to become a stimulatable needle. The insert 2219 may contain threads or other type of fitting on either or both sides that engage with the introducer end 2207 and/or the catheter hub 2206.

The catheter 2202 may include markings as described herein, e.g., markings as described with reference to FIGS. 28A-28B. Moreover, the catheter 2202 may include a preformed resilient distal portion configured to position the distal portion at least partially around a nerve. The preformed resilient distal portion may be configured to minimize dislodgment of the catheter 2202 from a treatment situs. Optionally, the catheter 2202 may be configured to fixedly bend from a first position to a second position with application of curved guidewire and curvature relative to a longitudinal axis of the catheter 2202 the curvature may be in a range from about 1 degree to about 180 degrees, more preferably the curvature is a range from about 80 degrees to about 110 degrees. The catheter 2202 may configured as described in FIGS. 6A-6B or any embodiment described herein like with any other catheter described herein.

Figure 24:
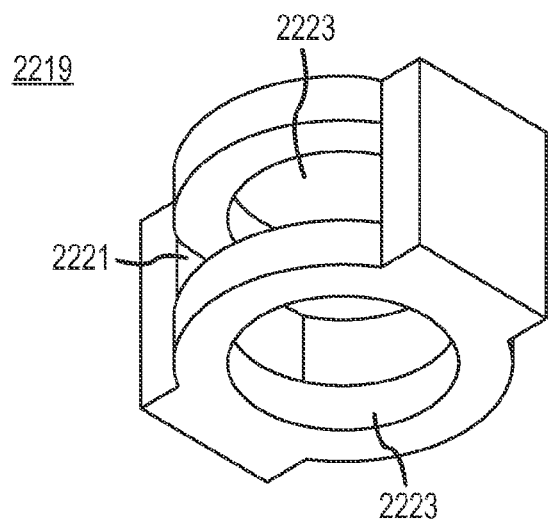
FIG. 24 illustrates an insert for connection of an electrical nerve stimulator to a cannula according to another embodiment of the invention.

FIG. 24 is a view of the insert 2219. The insert 2219 contains openings 2223 which allows the introducer to fit through the insert 2219. A portion of the insert 2223 may contain threads to engage with an exterior thread on the introducer 2207 which may hold the introducer 2207 in place during use. Alternatively, the insert 2219 may be a slip fit, such that once the introducer 2207 is in place, it fits snugly within the insert 2219. In another embodiment, the insert 2219 contains threads on the end that abuts the introducer end, and engages with threads on a portion of the introducer. In another embodiment, the insert 2219 contains threads or other fittings on the end that abuts the catheter hub, which engages with threads on the catheter hub. In another embodiment, the insert 2219 contains threads on both ends. Once the catheter is in place, the user may connect a nerve stimulation device to the exposed segment of the introducer shaft to convert the introducer into a stimulating needle for nerve localization.

In some embodiments, the insert 2219 contains at least one optional opening 2221. The opening 2221 may be any shape or size and may provide access to the introducer through the insert 2219. In other embodiments, the insert 2219 is a solid piece, without any openings 2221. In still other embodiments, the insert is tapered on one end such that the tapered end comes into contact with the introducer. The insert 2219 may be connected to a stimulator in order to stimulate the introducer. In still other embodiments, the insert 2219 may be ergonomical and may include indents for fingers—in particular it may include a groove to receive a portion of the thumb of the user. The insert 2219 may assist the user to disconnect the introducer from the catheter with the use of only one hand.

The insert 2219 may vary in length and may be made of any suitable materials. In some embodiments, the insert 2219 is made from a polymeric material. In other embodiments, the insert 2219 is made of an electrically conductive material. In other embodiments, the insert 2219 may be made of a polymeric material, which has been impregnated with an electrically conductive material.

Figure 25A:
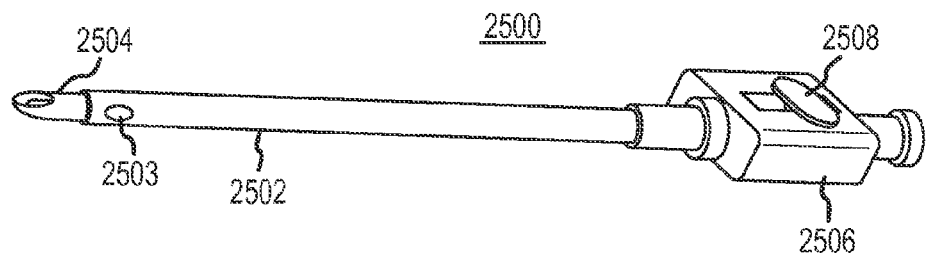
FIG. 25A illustrates a perspective view of a continuous anesthesia nerve conduction apparatus according to another embodiment of the invention in first orientation.
Figure 25B:
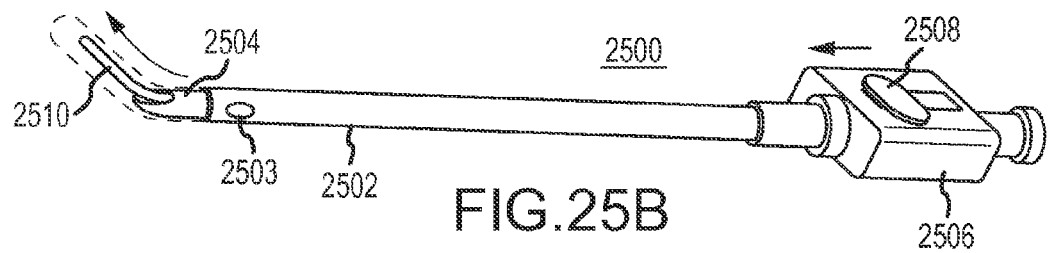
FIG. 25B illustrates the continuous anesthesia nerve conduction apparatus of FIG. 25A in a second orientation.
Figure 25C:
FIG. 25C illustrates a guidewire according to another embodiment of the invention.
Figure 25D:
FIG. 25D illustrates a guidewire according to another embodiment of the invention.

FIG. 25A illustrates a perspective view of a continuous anesthesia nerve conduction apparatus according to another embodiment of the invention in first orientation. FIG. 25B illustrates the continuous anesthesia nerve conduction apparatus of FIG. 25A in a second orientation. FIG. 25C illustrates a guidewire according to another embodiment of the invention. FIG. 25D illustrates a guidewire according to another embodiment of the invention.

Referring to FIGS. 25A-25D, a continuous anesthesia nerve conduction apparatus is generally depicted as reference number 2500. The apparatus 2500 includes an integrated guidewire with a needle to allow for single handed deployment of guidewire by advancing the tab on the needle hub. Also this apparatus reduces procedural steps by not having to detach the syringe before advancing guidewire. The apparatus 2500 includes a reinforced catheter 2502 over a cannula 2504 with an integrated hub 2506. The catheter 2502 includes a port 2503. The hub includes a guidewire advancer 2508 configured to move a guidewire 2510 from a first position to a second position with activation from a user, e.g., a thumb of a user, as shown by the arrow. The catheter 2502 can slide off the cannula 2504. The guidewire 2510 may be configured with an angled geometry 2512 at a distal tip to aid bending a distal portion of the catheter 2502 around or partially around a nerve. The cannula 2504 includes a lumen extend from proximal portion to a distal portion to allow fluid transfer. The catheter and/or cannula may include markings as described here to aid with location of each to a desired treatment situs. The guidewire may also be a steerable guidewire as known in the art.

Figure 26A:
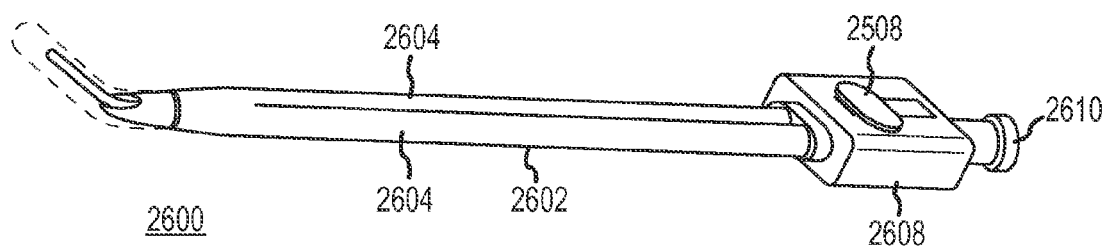
FIG. 26A illustrates a continuous anesthesia nerve conduction apparatus according to another embodiment of the invention.
Figure 26B:
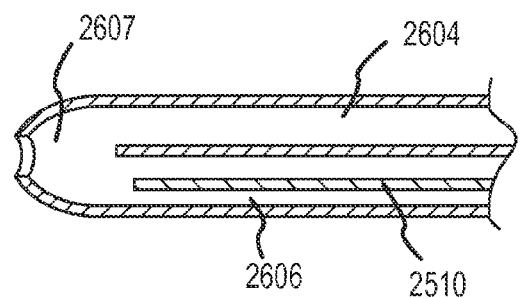
FIG. 26B illustrates a cross-sectional view of a distal portion of the continuous anesthesia nerve conduction apparatus according to FIG. 26A.

FIG. 26A illustrates a perspective view of a continuous anesthesia nerve conduction apparatus according to another embodiment of the invention. FIG. 26B illustrates a cross-sectional view of the continuous anesthesia nerve conduction apparatus according to FIG. 26A.

Referring to FIGS. 26A-26B, a continuous anesthesia nerve conduction apparatus is generally depicted with reference to number 2600. In this embodiment, an integrated catheter with a dual lumen is illustrated. The apparatus 2600 includes a catheter 2602 having a first lumen 2604 and a second lumen 2606. The first lumen 2604 and second lumen 2606 merge to one lumen 2607 at a distal portion of the catheter. The first lumen 2604 extends from a proximal portion to a distal portion of a hub 2608. A port 2610 is in fluid communication with the first lumen 2604. The hub 2608 includes a guidewire advancer 2508 configured to a move a guidewire 2510 from a first position to a second position with activation from a user, e.g., a thumb of a user.

The guidewire 2510 may be configured with an angled geometry 2512 at a distal tip to aid bending a distal portion of the catheter 2502 around or partially around a nerve. The catheter 2602 in this embodiment is configured to puncture a skin directly and has functional characteristics as a cannula. The catheter may include a side port or plurality of ports. The catheter may include markings as described here to aid with location of each to a desired treatment situs. Optionally, an additional removable sleeve may be utilized over the catheter 2602.

Figure 27A:
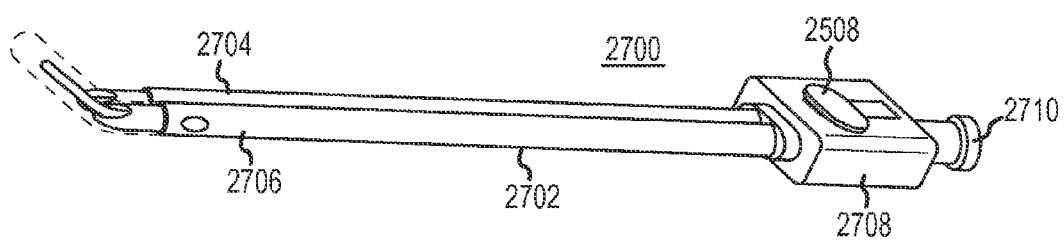
FIG. 27A illustrates a continuous anesthesia nerve conduction apparatus according to another embodiment of the invention.
Figure 27B:
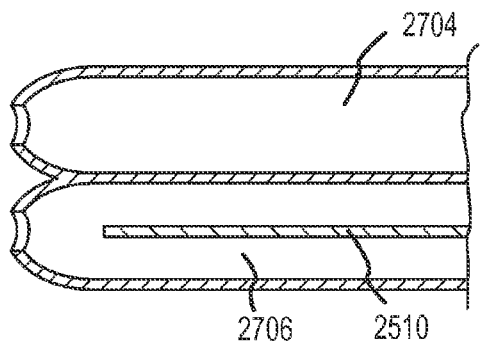
FIG. 27B illustrates a cross-sectional view of a distal portion of the continuous anesthesia nerve conduction apparatus according to FIG. 27A.

FIG. 27A illustrates a perspective view of a continuous anesthesia nerve conduction apparatus according to another embodiment of the invention. FIG. 27B illustrates a cross-sectional view of the continuous anesthesia nerve conduction apparatus according to FIG. 27A.

Referring to FIGS. 27A-27B, a continuous anesthesia nerve conduction apparatus is generally depicted with reference to number 2700. In this embodiment, an integrated catheter with a dual lumen is illustrated. The apparatus 2700 includes a catheter 2702 having a first lumen 2704 and a second lumen 2706. The first lumen 2704 and second lumen 2706 extend from a proximal portion to a distal portion of a hub 2708. A port 2710 is in fluid communication with the first lumen 2704. The hub 2708 includes a guidewire advancer 2508 configured to move a guidewire 2510 from a first position to a second position with activation from a user, e.g., a thumb of a user.

The guidewire 2510 may be configured with an angled geometry 2512 at a distal tip to aid bending a distal portion of the catheter 2502 around or partially around a nerve. The catheter 2702 in this embodiment is configured to puncture a skin directly and has functional characteristics as a cannula. The catheter may include a side port or plurality of ports. The catheter may include markings as described here to aid with location of each to a desired treatment situs. Optionally, an additional removable sleeve may be utilized over the catheter 2702.

FIG. 28A illustrates a distal end of a continuous anesthesia nerve conduction apparatus according to another embodiment of the invention. FIG. 28B illustrates a distal end of a continuous anesthesia nerve conduction apparatus according to another embodiment of the invention.

Referring to FIG. 28A, a distal portion 2800 of a catheter 2802 includes a first port 2804, second port 2806 and third port 2808. The first port 2804 and second port 2806 are oriented on opposite side of the catheter 2802. A plurality of markings 2810, 2812, 2814, 2816, 2818, and 2820 are configured to aid in the angular orientation and longitudinal orientation of the catheter and ports 2804, 2806, and 2808. Any combination of markings may be used, e.g., more or less may be utilized. The markings may have different geometric configurations to also aid with orientations. The markings may include an echogenic material, radiopaque material, combination of the same and the like. In addition, the catheter may include markings as described with reference to U.S. Patent Application Publication 2012/0059308, which is hereby incorporated by reference as if fully set forth herein.

Referring to FIG. 28B, the distal portion 2800 includes two ports, 2804 and 2808 and at least one marking 2810 positioned immediately proximally adjacent to the port 2804. The marking 2804 is utilized to aid in port location and utilized to position the port 2804 to a desired treatment situs, e.g., a nerve.

Figure 29A:
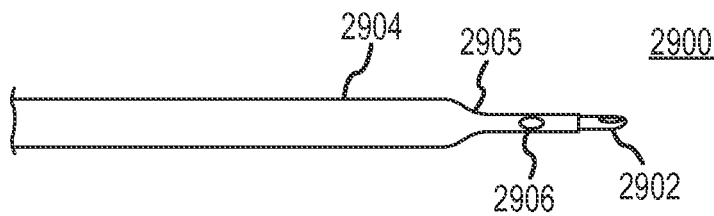
FIG. 29A illustrates an exemplary view of an apparatus according to an embodiment of the invention.
Figure 29B:
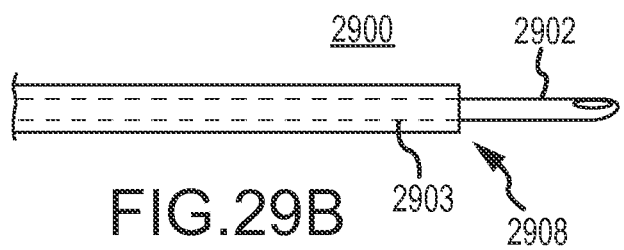
FIG. 29B illustrates an exemplary view of a cannula according to the apparatus of FIG. 29A.

FIG. 29A illustrates an exemplary view of an apparatus according to an embodiment of the invention. FIG. 29B illustrates an exemplary view of a cannula according to the apparatus of FIG. 29A.

Referring to FIGS. 29A-29B, a continuous nerve conduction apparatus is generally depicted as reference number 2900. The apparatus 2900 includes a catheter 2904 and a cannula 2902. The catheter 2904 is over the cannula 2902 and the cannula 2902 is slidably adapted to move though a lumen (not shown) of the catheter 2904. The cannula 2902 includes a lumen 2903 extending from a proximal region to a distal region. In a preferred embodiment, the lumen 2903 is configured to have a constant diameter from the proximal region to the distal region. The cannula 2902 and catheter 2904 may be constructed to include any features as described herein. Moreover, in one embodiment the cannula is described with reference to U.S. Patent Application Publication No. 2011/0112511, which is herein incorporated by reference as if fully set forth herein. The cannula 2902 may be a Touhy needle, Crawford needle, Hustead Needle, Sprotte needle, Whitacrea needle, Quincke needle, or other medical needles. In a preferred embodiment, the gauge of the needle is in a range from about 6 to about 26 and more preferably the gauge of the needle is in a range from about 18 to about 20.

The cannula 2902 and/or catheter 2904 include a change of diameter at a distal end portion 2908. The distal end portion of the cannula 2902 and/or catheter 2904 has a smaller diameter than a more proximal region of the cannula 2902 and/or catheter 2904. In one embodiment, the diameter changes from a larger diameter to a smaller diameter gradually at a taper at region 2905. In an alternative embodiment, the distal region of the cannula 2902 and/or catheter 2904 has a larger diameter as compared to a region more proximal of the cannula 2902 and/or catheter 2904.

The catheter 2904 includes at least one side port 2906, which is arranged in the distal region of the catheter 2904. At least one side port 2906 is configured to allow a pharmacologic agent to exit when the end port 2907 is occluded or partially occluded. Moreover, the side port 2906 may include any geometry or number as described herein. In a preferred embodiment, the side port 2906 includes four side ports arranged along the same axis of the catheter and uniformly spaced from each other. The distal end of the cannula 2902 includes a distal end port 2907 configured to allow a pharmacologic agent to exit.

The change from a larger diameter to a smaller diameter or vice versa may be a gradual taper having any type of shape, e.g., a linear taper shape, non-linear taper shape or a sharp taper shape. The sharp taper includes angle change from about 85 degrees to about 95 degrees from a central axis of the catheter. Moreover, the change from a larger diameter to a smaller diameter may be at any angle from the central axis of the catheter in a range from about 1 degree to about 90 degrees; preferably the taper is at an angle ranging from about 25 degrees to about 75 degrees, and more preferably the taper is at an angle ranging from about 35 to about 55 degrees.

The change in diameter size is configured to promote visualization under external imaging, e.g., ultrasound imaging or other imaging technology. The smaller or larger diameter change allows one to pin-point the change of diameter under ultrasound imaging without the need of an echogenic material or other type of visualization material. The diameter change may be in a range from about 0.1 gauge to about 5 gauge or greater, in a preferred embodiment the diameter change is in a range from about 2 gauge to about 4 gauge, and in a more preferred embodiment the diameter change is about a 2 gauge change. In a preferred embodiment, the region of catheter 2905 extending past the diameter change is in a range from 0.1 cm to about 4 cm, more preferably in a range from 0.5 cm to 2 cm, and most preferably in a range from about 1 cm to 1.8 cm. Moreover, the location of the lateral port 2906 can be determined as it is placed adjacent the diameter change or taper.

Figure 29C:
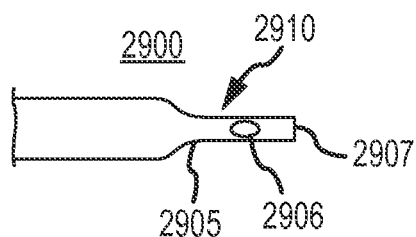
FIG. 29C illustrates an exemplary view of a catheter according to the apparatus of FIG. 29A.
Figure 29D:
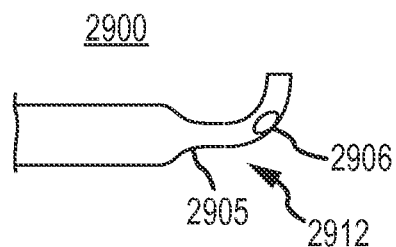
FIG. 29D illustrates an exemplary view of a catheter according to another embodiment of the invention.
Figure 29E:
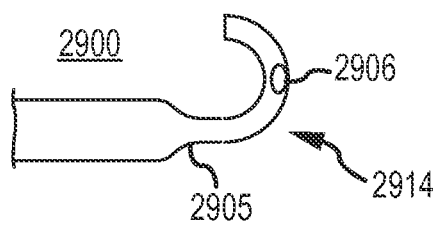
FIG. 29E illustrates an exemplary view of a catheter according to another embodiment of the invention.

FIG. 29C illustrates an exemplary view of a distal end region of a catheter according to the apparatus of FIG. 29A according to another embodiment of the invention. FIG. 29D illustrates an exemplary view of a distal end region of a catheter according to the apparatus of FIG. 29A according to another embodiment of the invention. FIG. 29E illustrates an exemplary view of a distal end region of a catheter according to the apparatus of FIG. 29A according to another embodiment of the invention.

Referring to FIG. 29C, the distal end region 2910 of the catheter 2904 includes a straight portion. The cannula 2902 in this embodiment also includes a distal end region being straight, i.e., with no curvature.

Referring to FIG. 29D, the distal end region of the catheter 2904 includes a curved region 2912 in a range from about 85 degrees to about 95 degrees. The cannula 2902 may also have a curved region at distal end region, e.g., in a range from about 1 degree to about 10 degrees or greater. In this embodiment, the catheter includes a portion having a curvature configured as a preformed memory shape as described herein.

Referring to FIG. 29E, the distal end region of the catheter 2904 includes a curved region 2914 in a range from about 185 degrees to about 175 degrees. The curved region may be configured in a range from about 5 degrees to about 185 degrees. In operation, this curved region is configured to provide a radial spread of local anesthetics out of one or more side ports 2906 and/or distal end port 2907. Neural structures are frequently cylindrical in shape and by positioning the catheter to cover a large area of the neural structure the pharmacological agent as dispensed surrounds a nerve providing for more efficacy of the agent. The cannula 2902 may also have a curved region at distal end region, e.g., in a range from about 1 degree to about 10 degrees or greater.

Figure 30A:
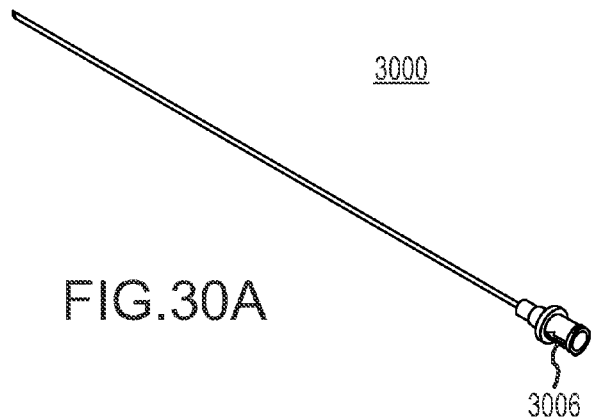
FIG. 30A illustrates a perspective view of a cannula according to another embodiment of the invention.
Figure 30B:
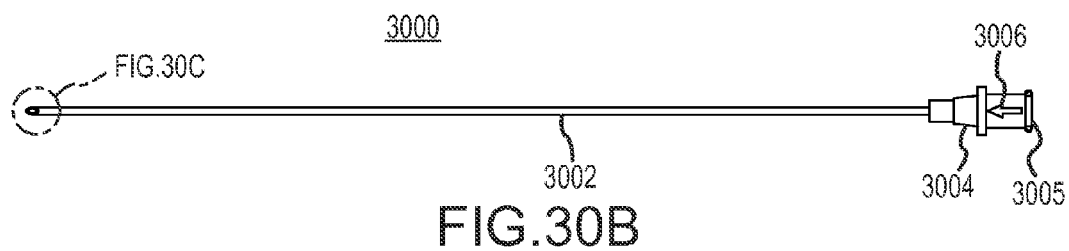
FIG. 30B illustrates a top-down view of the cannula according to FIG. 30A.
Figure 30C:
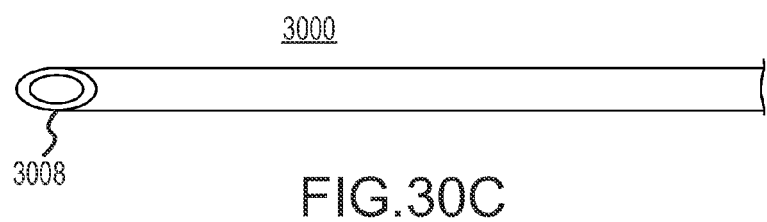
FIG. 30C illustrates an enlarged view of a distal end portion of the cannula according to FIG. 30A.

FIG. 30A illustrates a perspective view of a cannula according to another embodiment of the invention. FIG. 30B illustrates a top view of a cannula according to FIG. 30A. FIG. 30C illustrates an enlarged view of a cannula according to FIG. 30A.

Referring to FIGS. 30A-30C, a cannula is generally depicted as reference number 3000. The cannula 3000 is configured to be inserted through a lumen of a catheter. The cannula 3000 includes a shaft 3000 having a lumen extending form a proximal end to a distal end. The proximal end is coupled to a hub 3004 and the distal end has a Touhy tip needle or other medical needle.

The gauge of the cannula is in a range from about 10 gauge to about 26 gauge. In a preferred embodiment, the gauge is in range from about 18 gauge to about 20 gauge. The length of the cannula can be in a range from about 5 cm to 30 cm or greater. In a preferred embodiment, the length of the cannula is one of 7 cm, 15 cm, and 20 cm. The hub 3004 includes at least one alignment mark 3006. The alignment mark 3006 may be any type of notation or markings configured to determine an origination of a distal end portion of the cannula 3000. The hub 3004 includes a fitting 3005 configured to receive a syringe or other device.

The cannula 3000 includes a Touhy tip 3008. The Touhy tip 3008 has a slight curve portion at the end of the shaft 3002. The curved orientation is indicated by the alignment mark 3006. In this embodiment, the alignment mark 3006 is an arrow which indicates the curved portion of the Touhy tip is coming out of the page.

FIG. 31A illustrates a cross-sectional view of a cannula according to another embodiment of the invention. FIG. 31B illustrates a distal end view of the cannula of FIG. 31A. FIG. 31C illustrates an exploded view of a hub of FIG. 31A.

Referring to FIG. 31A, the cannula is generally depicted as reference number 3100. The cannula 3100 includes a shaft 3102 and is configured to be inserted through a lumen of a catheter. The cannula 3100 includes a shaft 3102 having a lumen extending form a proximal end to a distal end. The proximal end is coupled to a hub 3104 and the distal end has a Touhy tip 3106 or is configured as another needle as described herein. The hub 3104 includes at least one alignment mark (not shown). The cannula is configured to stimulate a nerve as known in the art. A conductive element 3108 is configured to transmit electrical activity used to activate a nerve via the cannula shaft 3102 to a distal portion of the catheter 302 and cannula 304. In a preferred embodiment, the electrical activity is generated by a nerve stimulator generator (not shown), e.g., Stimuplex® HNS11 Peripheral Nerve Stimulator by B. Braun, Stimuplex Dig RC by B. Braun, MultiStim VARIO by Pajunk, and EzStim® stimulator by Life-Tech International. In a preferred embodiment, the embedded conductive element 314 is an embedded wire.

Referring to FIGS. 31B and 31C, the hub 3104 is constructed from a proximal hub portion 3101, a conductive element 3108, and a distal hub portion 3103. The conductive element 3108 is an integral unit or solid unit formed from a conductive material. The conductive material is constructed from a conductive material. The conductive element 3108 includes a first tab 3105 and a second tab 3107 coupled to a cylindrical unit 3109. The proximal hub portion 3101 abuts the first tab 3105 and second tab 3107 and the distal hub portion 3103 abuts the first tab 3101, second tab 3105 and covers a proximal hub portion 3101.

In one embodiment, the conductive element 3108 and is formed from a single mold unit. The cylindrical unit 3109 includes a lumen configured to receive the cannula shaft 3102. Optionally, the first tab 3105 and second tab 3207 includes one or more holes (not shown) for acceptance of a clip of the nerve stimulator attachment mechanism. The shaft 3102 also includes an electrically insulated portion 3111 formed with an insulating coating such as thermoplastic coating.

The alignment mark includes any type of notation or markings configured to determine an origination of a distal end portion of the cannula 3100. In this embodiment, the Touhy tip 3106 has a slight curve portion at the end of the shaft 3102. The curved orientation of the Touhy tip is indicated by the alignment mark such as an arrow. The arrow which indicates the curved portion of the Touhy tip is coming out of the page. The gauge of the cannula is in a range from about 10 gauge to about 26 gauge. In a preferred embodiment, the gauge is in range from about 18 gauge to about 20 gauge. The length of the cannula can be in a range from about 5 cm to 30 cm or greater. In a preferred embodiment, the length of the cannula is one of 7 cm, 15 cm, and 20 cm.

Figure 32A:
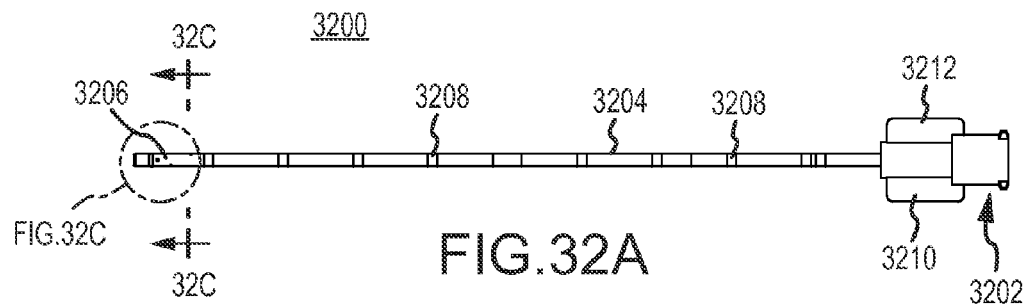
FIG. 32A illustrates an exemplary view of a catheter according to another embodiment of the invention.
Figure 32B:
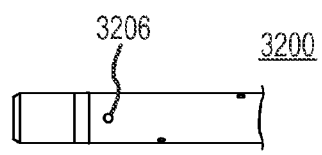
FIG. 32B illustrates an enlarged view of section B-B of the catheter of FIG. 32A.
Figure 32C:
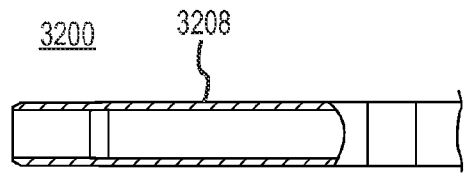
FIG. 32C illustrates an enlarged cross-sectional view of a distal end portion of the catheter of FIG. 32A.
Figure 32D:
FIG. 32D illustrates a proximal end view of the catheter of FIG. 32A.
Figure 32E:
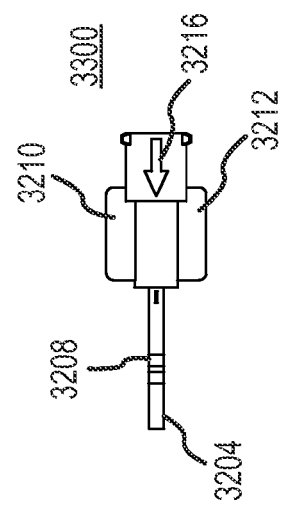
FIG. 32E illustrates an enlarged proximal view of the catheter of FIG. 32A.

FIG. 32A illustrates an exemplary view of a catheter according to another embodiment of the invention. FIG. 32B illustrates an enlarged view of section B-B of the catheter of FIG. 32A. FIG. 32C illustrates an enlarged cross-sectional view of a distal portion of the catheter of FIG. 32A. FIG. 32D illustrates an end view of the catheter of FIG. 32A. FIG. 32E illustrates an enlarged view of a hub according to the catheter of FIG. 2A.

Referring to FIGS. 32A-32E, a catheter is generally depicted as reference number 3200. The catheter 3200 includes a hub 3202 on a proximal portion, a shaft 3204 and one or more lateral ports 3206 on a distal portion. The shaft 3204 further includes markings 3208 configured to indicate the length the catheter. The markings 3208 are configured at predetermined increments in a range from about 1 cm to about 1 cm to about 10 cm or greater.

The hub 3202 includes a first tab 3210 and a second tab 3212 configured to be adhered to a portion of a patient. The first tab 3210 and the second tab 3212 include an adhesive on side configured to adhere to a patient. The adhesive may include a removable portion protecting the adhesive prior to first use. A distal end of the catheter includes a taper at an angle of about thirty degrees relative to a central axis. The catheter may optionally be reinforced with a secondary material in order to increase stiffness of the catheter and substantially prevent kinking. The reinforcement may be constructed from a metal, polymer, thermoplastic and combinations of the same.

The shaft 3204 includes a plurality of lateral ports 3206 arranged at a distal end portion of the catheter. The spacing between adjacent lateral ports are uniformly spaced and offset from each other at an angle around a circumference of the shaft 3204. In this embodiment, the angle between lateral ports is about 120 degrees as shown in FIG. 32D. The diameter of each lateral port may be identical to an adjacent lateral port. The diameter is in a range from about 0.005 inches to about 0.05 inches or greater. Optionally, the hub 3202 includes an alignment mark 3216 configured to show an orientation of the lateral port. In one embodiment, there may be a plurality of alignment marks on the hub where each alignment mark is configured to depict the orientation of each lateral port, respectively.

Figure 33:
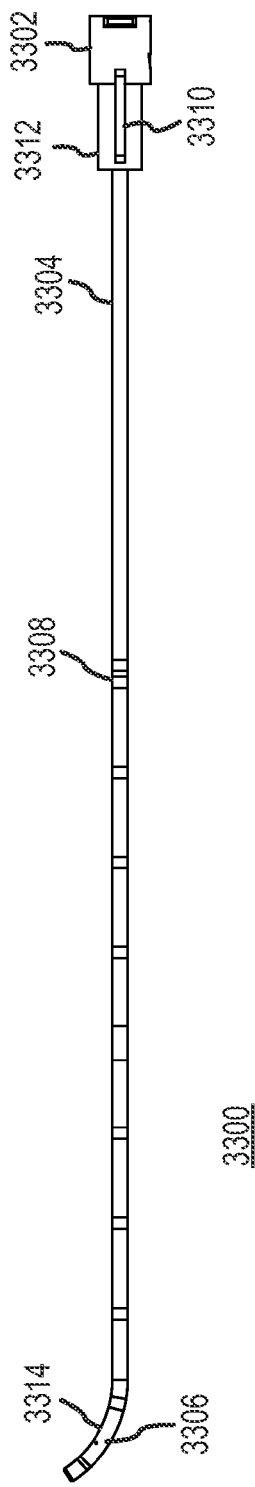
FIG. 33 illustrates an exemplary view of a catheter according to another embodiment of the invention.

FIG. 33 illustrates an exemplary view of a catheter according to another embodiment of the invention.

Referring to FIG. 33, a catheter is generally depicted as reference number 3300. The catheter 3300 includes a hub 3302 on a proximal portion of a shaft 3304 and one or more lateral ports 3306 on a distal portion of the shaft 3304. The shaft 3304 further includes markings 3308 configured to indicate the length the catheter as described herein. The hub 3302 includes a first tab 3310 and a second tab 3312 configured to be adhered to a portion of a patient. The first tab 3310 and the second tab 3312 are described herein.

The catheter includes a curved portion 3314 on the distal portion of the shaft 3304. The curved portion is preformed into the catheter as a memory shape. When a cannula is in the catheter the catheter distal end is straight and upon removal of the cannula the catheter is curved to the preformed shape. The shape of the curve may be at any angle as described herein. In a preferred embodiment, the curvature has a radius of about 0.5 inches.

Figure 34A:
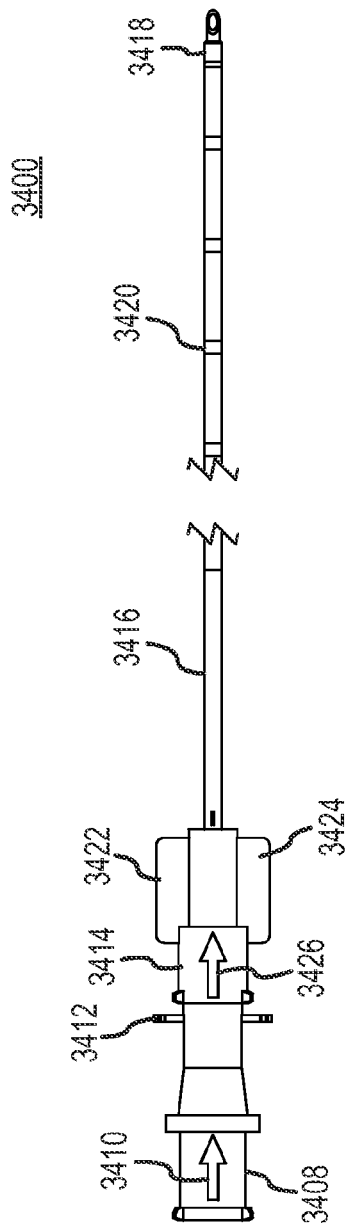
FIG. 34A illustrates a top view of a continuous anesthesia nerve conduction apparatus according to another embodiment of the invention.
Figure 34B:
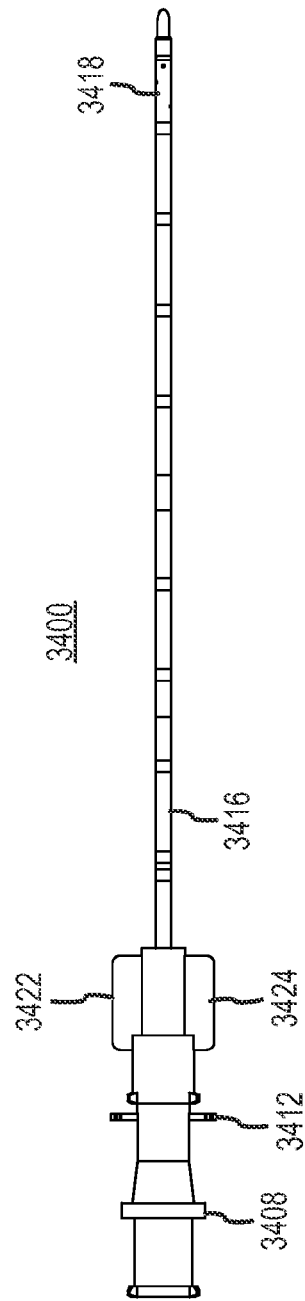
FIG. 34B illustrates a bottom view of a continuous anesthesia nerve conduction apparatus according to FIG. 34A.
Figure 34C:
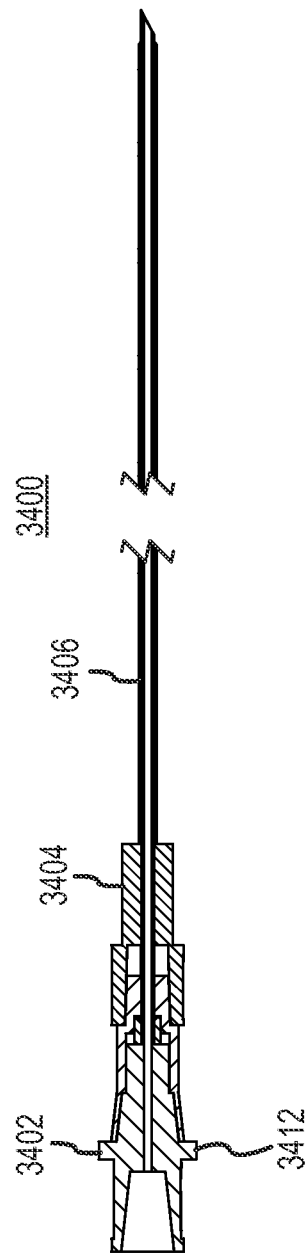
FIG. 34C illustrates a cross-sectional view of the continuous anesthesia nerve conduction apparatus according to FIG. 34A.

FIG. 34A illustrates a top view of a continuous anesthesia nerve conduction apparatus according to another embodiment of the invention. FIG. 34B illustrates a bottom view of a continuous anesthesia nerve conduction apparatus according to FIG. 34A. FIG. 34C illustrates a cross-sectional view of the continuous anesthesia nerve conduction apparatus according to FIG. 34A.

Referring to FIGS. 34A-34C, the apparatus is generally depicted as reference number 3400. The apparatus 3400 includes a cannula 3402 and a catheter 3404. The cannula 3402 and hub 3408 are described with detail with respect to FIGS. 31A-31C. The cannula 3402 is arranged through a lumen of a catheter 3404. The cannula 3402 includes a shaft 3406 having a lumen coupled to a hub 3408 and at least one alignment mark 3410 configured to indicate the orientation of a curvature of a distal end of the cannula as described herein. The hub 3408 includes a conductive element 3412 configured to be attached to a nerve stimulator as described herein.

The catheter 3404 is described in further detail with regard to FIGS. 32A-32C. The catheter 3404 includes a hub 3414 on a proximal portion of a shaft 3416 and one or more lateral ports 3418 on a distal portion of the catheter 3404. The shaft 3416 of the catheter 3404 includes markings 3420 configured to indicate the length of the catheter. The hub 3414 includes at least one alignment mark 3426 configured to indicate the orientation of a lateral port 3418 as described herein.

The hub 3408 of the cannula 3402 and hub 3414 of the catheter 3404 are configured to fit together in substantially locked configuration such that there is continuous lumen extending between and through both hubs. The locked configuration substantially prevents individual rotation of either the catheter 3404 or cannula 3402, thereby allowing the catheter and cannula to be utilized as one unit. In an alternative embodiment, the portion where the hubs are in contact with each include male and female notches arranged at predetermined orientations on respective contact surfaces of the hubs. These notches may be arranged in a circular pattern along an axis of the hub at various degrees, e.g., 30 degrees, 60 degrees, 90 degrees, 120 degrees, 150 degrees, and 180 degrees. The notches are configured to permit offset rotation of the catheter relative to the cannula at each predetermined orientation. When the male and female notches are engaged the catheter and cannula are in substantially locked configuration.

The hub 3414 includes a first tab 3422 and a second tab 3424 configured to be adhered to a portion of a patient. The first tab 3422 and the second tab 3424 include an adhesive on side configured to adhere to a patient. The adhesive may include a removable portion protecting the adhesive prior to first use. The end of the catheter includes a taper at about 30 degrees. The catheter may optionally be reinforced with a secondary material, e.g., metal, polymer, thermoplastic and the like in order to increase stiffness.

Figure 35A:
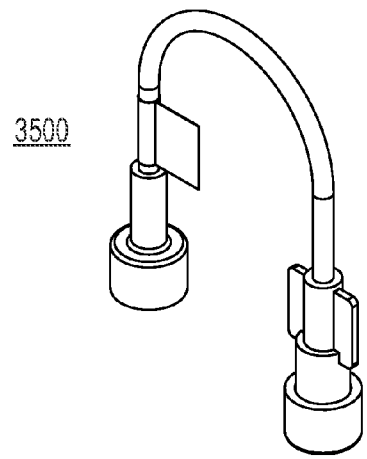
FIG. 35A illustrates a perspective view of an extension tubing set according to another embodiment of the invention.
Figure 35B:
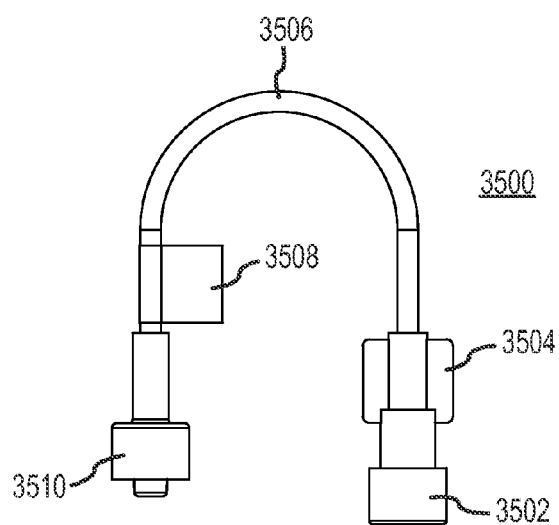
FIG. 35B illustrates a side view of the extension tubing set of FIG. 35A.

FIG. 35A illustrates a perspective view of an extension set according to another embodiment of the invention. FIG. 35B illustrates a side view of the extension set of FIG. 36A.

Referring to FIGS. 35A-35B, the extension unit is generally depicted as reference number 3500. The extension unit 3500 includes a fitting 3502 coupled to a tubing 3506 coupled to another fitting 3510. The fittings of this embodiment may include a luer connector, e.g., a male luer connector, female luer connector, and/or luer-lock connector. In a preferred embodiment, the fitting 3502 is luer lock male cap connector configured to be releasably coupled to a hub of a catheter and/or cannula, e.g., catheter hub 3414 or cannula hub 3408. A flexible tubing 3506 is connected to the fitting 3502 and a male luer connector 3510.

The fitting 3502 and/or tubing 3506 includes a first tab 3502 and a second tab 3504 configured to be adhered to a portion of a patient. The first tab 3502 and the second tab 3504 include an adhesive on one side configured to adhere to a patient. The adhesive may include a removable portion protecting the adhesive prior to first use. The fitting 3510 and/or tubing 3506 also include a label 3508. In a preferred embodiment, the label 3508 is a warning label to indicate the type of catheter such as a nerve catheter versus an intravenous (iv) catheter. The label 3508 and tabs 3504 are integral or built into the extension set 3500. The length of the tubing is no more than about five inches and in preferred embodiment about three inches in length. This short tubing length provides for an enhanced ease of use and minimizes contamination, thereby allowing a user to operate the system with one handed operation.

Figure 36A:
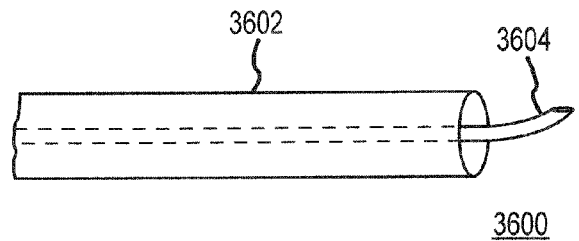
FIG. 36A illustrates an enlarged view of a portion of a continuous anesthesia nerve conduction apparatus according to another embodiment of the invention.
Figure 36B:
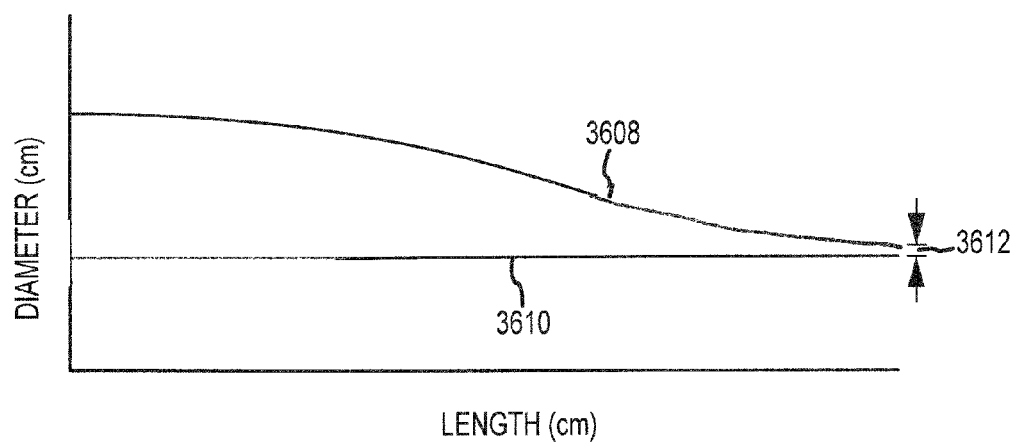
FIG. 36B illustrates a graph of an interference fit according to FIG. 36A.

FIG. 36A illustrates a perspective view of a continuous anesthesia nerve conduction apparatus according to another embodiment of the invention. FIG. 36B illustrates a graph of an interference fit according to the apparatus of FIG. 36A.

Referring to FIGS. 36A-36B, the apparatus is generally depicted as reference number 3600. The apparatus 3600 includes a catheter 3602 and cannula 3604. A distal portion of the catheter may have a curvature or no curvature as described herein. The cannula 3604 may include a Touhy tip or other needle as described herein. In this embodiment, the catheter 3602 has a lumen extending from proximal portion to a distal end. The distal portion of the catheter may also include side ports (not shown) as described herein. An inside diameter of the lumen of the catheter 3602 decreases along a distal portion to the catheter as shown in FIG. 36B. This decrease allows for a resistant fit or interference fit of the cannula 3604, thereby requiring the user to apply an increased force to extend the cannula 3604 out a distal end of the catheter 3602. The decrease of the inside diameter may be linear, non-linear or any combination of the same.

Referring to FIG. 36B, the graph includes the diameter of an inside diameter 3608 of a lumen of the catheter and outside diameter 3610 of the cannula on an x-y graph. The x-axis of the graph depicts a length [cm] of the catheter 3602 and/or cannula 3604 and the y-axis of the graph depicts a diameter [cm]. As shown, the inside diameter 3608 of the lumen of the catheter 3602 decreases as it approaches a distal end portion of the catheter 3602. The outside diameter 3610 of the cannula is static or constant as shown in the graph. In one embodiment, the distance delta 3612 between the inside diameter of the catheter lumen and outside diameter of the cannula is in a range from about 0.1 mm to about 0.0001 mm. In a preferred embodiment, the distance delta is less than about 0.5 mm and may be about 0 mm.

This embodiment produces an interference fit between the cannula and the catheter, thereby permitting the cannula and the catheter to act as one solid unit when used. In one embodiment, the materials of the catheter include a thermoplastic material that allows for some expansion to add in the interference fit. This interference fit is configured to minimize or eliminate any gap to between the distal end or distal end portions of the cannula and the inside diameter of the catheter, thereby minimizing the probability that the catheter compresses, bunches, and/or snags upon tissue of a patient. In a preferred embodiment, the distal most portion of the catheter is angled or beveled as described with reference to FIG. 32B.

FIG. 37A illustrates a perspective view of a continuous anesthesia nerve conduction apparatus according to another embodiment of the invention. FIG. 37B illustrates a catheter according to another embodiment of the invention. FIG. 37C illustrates an anti-restriction member according to another embodiment of the invention.

Referring to FIGS. 37A-37C, the apparatus includes a cannula 3702, a catheter 3704, and an anti-restriction member 3706. The anti-restriction member 3706 is configured to be inserted into a lumen of the catheter 3704. The anti-restriction member 3706 is conductive such that it can be used as a nerve stimulator. Optionally, a portion of the member 3706 is insulated with a coating (not shown).

In this embodiment, the catheter 3704 includes a hub 3708 and a flexible tubing 3710 having a lumen that extends from a proximal end to a distal end. The lumen is configured to deliver a pharmacological agent to a desired treatment situs. The flexible tubing 3710 can kink or bend, thereby preventing fluid flow through the lumen. The flexible tubing 3710 includes one or more lateral ports 3712 at distal end portion of the catheter 3704. In one embodiment, the hub 3708 includes an alignment mark configured to show the orientation of the lateral port 3712 as described herein.

The cannula 3702 includes a shaft 3714, a hub 3716, a conductive connector 3718 and an alignment mark (not shown) as described with reference to FIGS. 31A-31C and related text. The cannula 3702 is configured to be inserted into the catheter 3704. Both the cannula 3702 and the catheter 3704 are configured to be inserted into a patient as a single unit. The catheter 3702 and the cannula 3704 may be configured with an interference fit as described with reference to FIGS. 36A-36B and related text.

After insertion the cannula 3702 is removed from the catheter 3704. Optionally, an anti-restriction member 3706 may be inserted into the catheter 3704. The anti-restriction member 3706 includes a hub 3722, a stimulation attachment 3724, and a fitting 3725. The anti-restriction member 3706 includes an element 3726 that enables fluid flow to continue through the lumen of the catheter 3704 when inserted. In addition, the element 3726 is configured to prevent kinking of the catheter and provide patency of the lumen catheter 3704. In this embodiment, the element 3726 is constructed from a conductive material and into a geometric configuration to preserve patency of the lumen of the catheter 3704.

The geometric configuration can include a helix braided wire, a spiral laser cut hypo-tube, a stent like structure and combinations of the same. Should kinking or bending occur when the anti-restrictive member 3706 is positioned in the catheter 3704 the element 3728 can act as a flow element to allow fluid to flow even upon kinking or bending of the catheter and element 3728.

In this embodiment, when the element 3726 is configured to be used as a nerve stimulator, the element 3726 is sized such that a distal most portion of the element 3726 extends past a distal end of the catheter 3704. Moreover, tabs 3722, 3724 on the hub 3725 are configured to be attached to a nerve stimulator. The hub 3725 is also configured with a fitting 3725. The fitting 3725 can include a luer connector, e.g., a male luer connector, female luer connector, and/or luer-lock connector. In a preferred embodiment, the fitting 3725 is configured to be releasably attached to a syringe and/or a tubing of a pump.

FIG. 37D illustrates a catheter according to another embodiment of the invention.

Referring to FIG. 37D, a catheter is generally depicted as reference number 3728. The catheter 3728 includes a rigid shaft 3730 having a lumen extending from proximal end to a distal end and the shaft 3730 and is coupled to a hub 3732. The catheter 3728 does not include any lateral ports and is configured to be inserted into a lumen of the catheter 3704, thereby strengthening the shaft 3710 of the catheter 3704 and also configured to prevent kinking and/or bending of the catheter.

The catheter 3728 includes a hub 3732 with a connector 3735. The lumen of the catheter 3728 is configured to deliver a pharmacological agent to a desired treatment situs. The length of the catheter shaft 3730 is sized to be shorter than the distal end of the catheter shaft 3710 and shorter than lateral port 3712. Optionally, one or more predetermined portions of the catheter 3730 can include a visualization enhancement. The visualization enhancement may include an echogenic material arranged at a predetermined location of the shaft and in a predetermined pattern as described herein.

FIG. 37E illustrates a catheter according to another embodiment of the invention.

Referring to FIG. 37E, a catheter is generally depicted as reference number 3734. The catheter 3734 includes a rigid shaft 3736 having a lumen extending from proximal end to a distal end and the shaft 3736. The shaft 3736 is coupled to a hub 3738. The catheter 3734 includes lateral ports 3740. The catheter 3734 is also sized to be inserted into a lumen of the catheter 3704, thereby strengthening the shaft 3710 of the catheter 3704 and substantially preventing kinking and/or bending of the catheter 3704.

The catheter shaft 3736 includes a hub 3738 with a fitting 3737. The lumen of the catheter 3734 is configured to deliver a pharmacological agent to a desired treatment situs when in use. The length of the catheter shaft 3736 is sized to be longer than the distal end of the catheter 3704. In a preferred embodiment, the length of the catheter 3734 is sized such that the lateral ports 3740 extend immediately out the distal end of the catheter 3704. A distal end of the catheter 3734 can include a visualization enhancement at a desired location. The visualization enhancement may include an echogenic material arranged at a predetermined location of the shaft and predetermined pattern as described herein.

FIG. 37F illustrates a catheter according to another embodiment of the invention.

Referring to FIG. 37F, a catheter is generally depicted as reference number 3742. The catheter 3742 includes a rigid shaft 3746 having a lumen extending from proximal end to a distal end of the shaft 3746. The shaft 3746 is coupled to a hub 3743. The catheter 3742 includes lateral ports 3748 and is sized to be inserted into a lumen of the catheter 3704, thereby strengthening the shaft 3710 of the catheter 3705 and substantially preventing kinking and/or bending of the shaft 3710.

The catheter 3742 includes a hub 3743 with a fitting 3739. The lumen of the catheter 3742 is configured to deliver a pharmacological agent to a desired treatment situs. The length of the catheter shaft 3746 is sized to be longer than the distal end of the catheter 3704. In a preferred embodiment, the length of the catheter 3742 is sized such that lateral ports 3748 extend immediately out a distal end of the catheter 3704. A distal end of the catheter 3742 can include a visualization enhancement material at a desired location. The visualization enhancement material may include an echogenic material arranged at a predetermined location of the shaft and arranged in predetermined patterns. The distal end of the catheter 3742 includes preformed curvature as described herein.

FIG. 37G illustrates a catheter according to another embodiment of the invention.

Referring to FIG. 37G, a catheter is generally depicted as reference number 3750. The catheter 3750 includes a rigid shaft 3752 having a lumen extending from proximal end to a distal end of the shaft 3752. The shaft 3752 is coupled to a hub 3753. The catheter 3750 includes lateral ports 3754 and is sized to be inserted into a lumen of the catheter 3704, thereby strengthening the shaft 3710 of the catheter 3704 to substantially prevent kinking and/or bending of the shaft 3710.

The catheter 3750 includes a hub 3753 including a fitting 3741. The hub 3753 also includes a conductive element 3745. The conductive element 3745 is formed from a single mold unit as described herein. A conductive wire or element not shown extends down a catheter shaft 3752 as described herein with reference to FIG. 3B. The catheter 3750 includes a conductive end portion, e.g. cap. The catheter is used as a stimulating catheter configured to stimulate a nerve and extend out a distal end of the catheter 3704.

The length of the catheter shaft 3752 is sized to be longer than the distal end of the catheter 3704. In a preferred embodiment, the length of the catheter 3750 is sized such that the lateral ports 3756 extend immediately out the distal end of the catheter 3742. Optionally, a distal end portion of the catheter 3742 can include a visualization enhancement material at a desired location. The visualization enhancement material may include an echogenic material arranged at a predetermined location of the shaft and predetermined pattern as described herein. The distal end of the catheter may also include preformed curvature as described herein.

Figure 38:
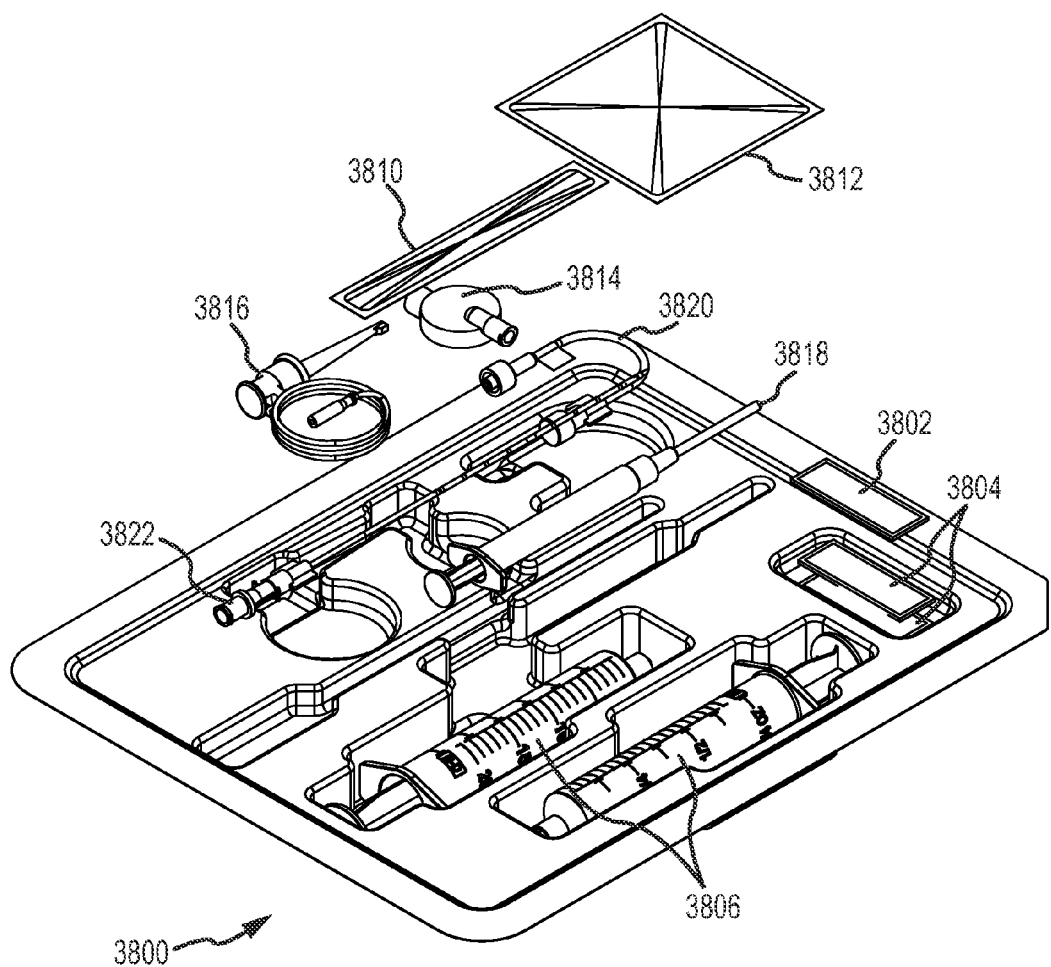
FIG. 38 illustrates a kit according to an another embodiment of the invention.

FIG. 38 illustrates a medical device kit according to another embodiment of the invention.

Referring to FIG. 38, a kit is generally depicted as reference number 3800. The kit 3800 is configured to hold an apparatus and associated medical surgical items described herein. In this embodiment, the kit 3800 includes a thermo formed mold constructed from a thermoplastic material. The mold has a plurality of recessed slots to receive various components of the kit. The kit and the components are sterilized to comply with governmental medical standards, e.g., U.S. Food and Drug Administration (FDA) standards. A protective sterile plastic film covers and seals the kit.

The kit 3800 includes a first needle 3802 having first size, a second needle 3804 having a second size smaller than the size of the first needle, a first syringe 3806, a label (not shown), a steri-strip 3810, a tegaderm patch 3812, a filter 3814, an electrical connector 3816, a second syringe 3818 smaller than the size of the first syringe 3806, an extension set 3820 as described with reference to FIGS. 35A-35B, and an apparatus and cannula described according to any of the embodiments herein.

Described next is a method of administrating a pharmacological agent in accordance with another embodiment of the invention. This embodiment will be described with reference to the continuous anesthesia nerve conduction apparatus described herein FIGS. 3A-3C. However, any apparatus described herein may be used with this procedure.

Advantageously, the method of administering the pharmacological agent in accordance with the invention does not need to occur in a fully sterile environment and is much faster than the traditional methods of administrating a pharmacological agent. In addition, the operator can perform the method by herself without requiring assistance from another person.

Initially, preparatory steps are performed prior to performing a procedure. These steps include applying non-sterile gloves on both hands and opening sterile packaging kit 3800 of the apparatus 302. Next, a cannula 304 is positioned through the lumen 326 of the catheter 302, and the cannula 304 is secured to the hub of the catheter 302 via locking mechanism 322. In an embodiment, each of the items used during the procedure are provided in a sterile kit. In another embodiment, each item used during the procedure is preassembled in the kit.

A syringe (not shown) is connected to the cannula hub 320. A distal portion of the catheter 302 is maintained in a sterile manner within its covering. The proximal portion of the catheter 302 and cannula 304 are exposed so that a standard syringe filled with a liquid solution is coupled to the hub 320.

Next, a patient is positioned according to the type and location of nerve(s) to be targeted as known in the art. The operative portion of the patient (insertion site) is prepped with an antiseptic solution. If a peripheral nerve stimulator is being used, the peripheral nerve stimulator is connected to the exposed proximal end of the apparatus via an electrode connector 316 on the proximal hub of the catheter 302. The necessary connection for the peripheral nerve stimulator to the patient is also performed and the nerve stimulator is activated for the appropriate setting as known in the art.

An ultrasound probe is held in the non-operative hand and positioned on the patient to obtain an image of the targeted nerve(s). Once the ultrasound probe is in position, the insertion site for the apparatus including a cannula 304 and catheter 302 (combined apparatus) can be ascertained and a skin wheal is raised to anesthetize the insertion site.

With the other hand (operative hand), the combined apparatus is slipped out of the sterile covering and inserted through the insertion site. The distal tip of the combined apparatus is then advanced towards the targeted nerve(s) under direct visualization via the ultrasound image.

If nerve stimulation is used, the distal tip of the combined apparatus is advanced towards the targeted nerve(s) until the appropriate muscle stimulation is obtained for confirmation that the distal tip of the apparatus is positioned in proximity to the targeted nerve(s). Once adjacent to the targeted nerve(s), the solution in the standard syringe that was previously attached to the proximal hub of the introducing cannula 304 is injected to hydro-dissect the tissue surrounding the targeted nerve(s). Real time ultrasound visualization is possible because the non-operative hand is simultaneously positioning the ultrasound probe to obtain a view of the targeted nerve(s) and while positioning the distal portion of the inserted apparatus with the operative hand.

Once the tissue surrounding the nerve(s) is expanded with the solution in the syringe, the proximal hub 306 of the catheter is released from the hub lock 322 on the proximal hub 320 of the introducing cannula 304 with the operative hand. The catheter 302 is then advanced with a finger of the operative hand while the introducing cannula 304 is withdrawn from the lumen of the catheter 302 with the operative hand, much like advancing an intravenous catheter off the needle and into a blood vessel. This is done simultaneously while maintaining an ultrasound image of the distal portion of the catheter 302 and the targeted nerve(s) with the non-operative hand manipulating/managing the ultrasound probe. If the catheter's distal tip is not able to extend into its preformed shape due to tissue obstruction, a guidewire can be positioned through the lumen of the cannula to aid the directional positioning of the catheter tip.

With the catheter 302 positioned adjacent to the targeted nerve(s), and the introducing cannula 304 withdrawn, another syringe with local anesthetic solution is connected to the proximal hub of the catheter that is exteriorized on the patient, and local anesthetic can be injected via the catheter alone, while again being visualized in real-time with the ultrasound imaging maintained by the non-operative hand. Once placement of the distal tip of the catheter 302 and local anesthetic spread is confirmed by ultrasound imaging, the ultrasound probe and/or the peripheral nerve stimulator can be set aside.

The syringe can then be disconnected from the catheter 302, and the proximal hub 306 of the catheter 302 is secured to the patient's skin with adhesive tape applied to the hub and wings 308, 310. The hub can then be capped or connected to an infusion pump via a connecting tube. The externalized portion of the catheter 302 and hub 306 can be covered with a clear dressing to further minimize dislodgement, and maintain sterility.

These steps can be accomplished by one proficient in the arts in approximately the same time or less than it takes to perform a single-injection nerve block with a needle alone. The approximate time from positioning the patient (according to the type and location of nerve(s) to be targeted as known in the art) to securing and dressing the hub can take less than 10 minutes. In a preferred embodiment, the procedure takes less than 10 minutes to perform.

Another embodiment of the invention includes a kit for the delivery of a fluid to a nerve bundle of a patient. The kit includes a pump, a length of tubing securable to said pump, an introducer, and a catheter. The introducer is configured to fit within the catheter. The pump, tubing, catheter and introducer are provided together as a kit. Other items may also be provided in the kit, e.g., guidewire and stimulator.

Without intending to limit the scope of the invention, the following examples illustrate how various embodiments of the invention may be made and/or used.

EXAMPLES

The following examples illustrate the time to insert a catheter, secure the catheter and dress the patient using the method described herein (Example 1) as compared to the traditional method (Example 2).

Table 1 illustrates a timed comparison between the steps and method duration of Example 1, the method described herein, and steps and method duration of Example 2, the traditional method. Each step is described in detail below. All time listed in Table 1 are approximate.

Example 1

Examples 1 and 2 are directed towards a medical procedure for inserting a catheter for delivering a pharmacological agent to a nerve bundle in the neck of a patient. The method in each example generally included three broad steps: Step 1—Setup; Step 2—Procedure; and Step 3—Securing Catheter. Example 1 was conducted with an apparatus according to embodiments of the invention. Example 2 was conducted with a needle over catheter apparatus and the procedure to insert the needle over catheter apparatus.

Figure 39:
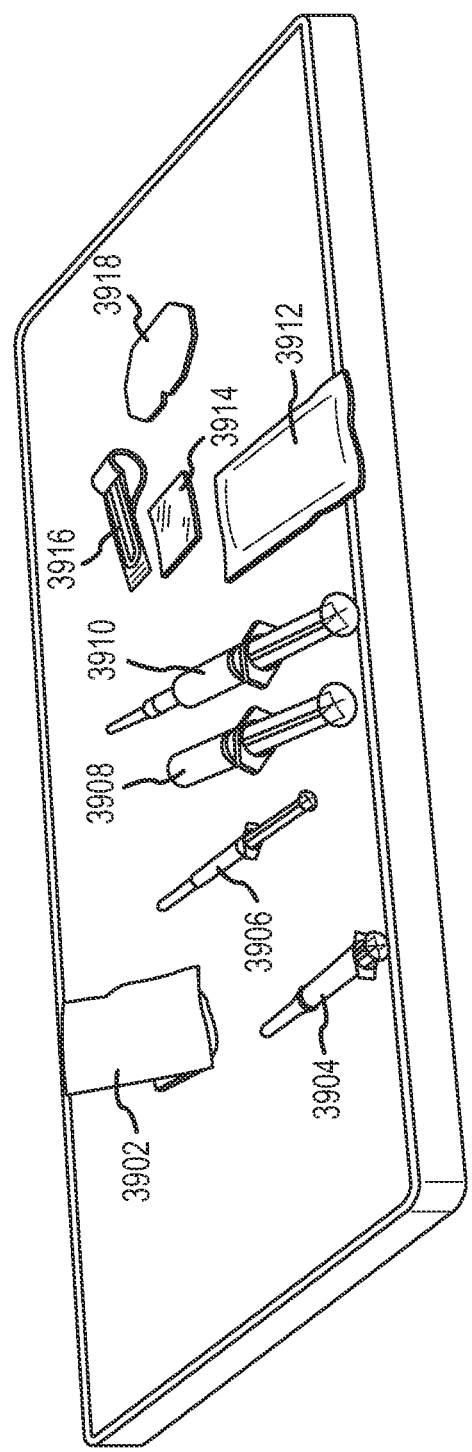
FIG. 39 illustrates exemplary supplies of a single sterile device package according to an example of the invention.
Figure 40:
FIG. 40 illustrates the localized sterilization of a patient's skin according to an example of the invention.

Step 1:

(Setup): The operator opened a single sterile device package, which included supplies such as a Terumo® 2.5 inch 18 gauge Surflo® I.V. Catheter. FIG. 39 illustrates items used in the procedure of Example 1. With reference to FIG. 39, these items include (starting from the top left of FIG. 39 and proceeding counter-clockwise) tubing (white package partially open) 3902, 5 cc syringe 3904 containing medication to sedate the patient, 3 cc syringe 3906 with a 25 gauge 1.5 inch needle attached to the syringe which contained Lidocaine, a 20 cc syringe 3908 with Ropivicaine, another 20 cc syringe 3910 which contained Ropivicaine with an angiocath attached to the syringe within a cover (the angiocath is an 18 gauge 2.5 inch needle within an 18 gauge 2.5 inch catheter, where the needle extends just past the tip of the catheter), a package of Betadine swabs 3912, securing strips 3914, a tacky substance 3916 to attach the securing strips and a clear dressing 3918. The operator put on non-sterile gloves and filled the syringes. The local area on the patient where the angiocath was inserted was prepared by swabbing the area with Betadine as illustrated in FIG. 40. The operator put the ultrasound probe in the vicinity of the nerve bundle. The ultrasound probe contained a small amount of gel applied to the tip of the probe. The probe was used to monitor the area surrounding the nerve bundle throughout the procedure.

Figure 41:
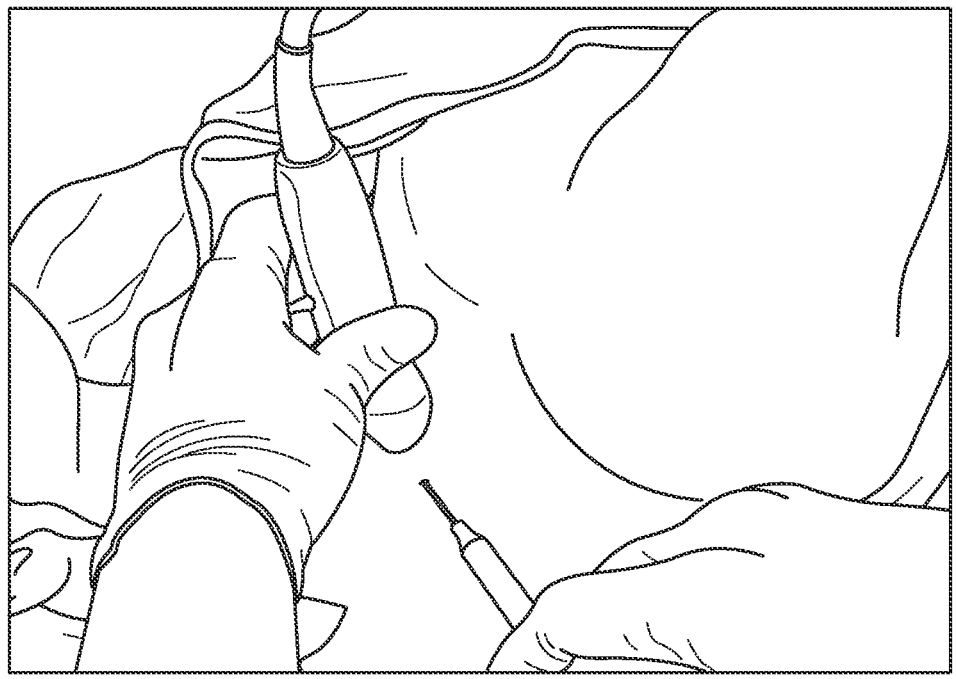
FIG. 41 illustrates the anesthetizing of a patient, while simultaneously imaging the patient according to an example of the invention.
Figure 42:
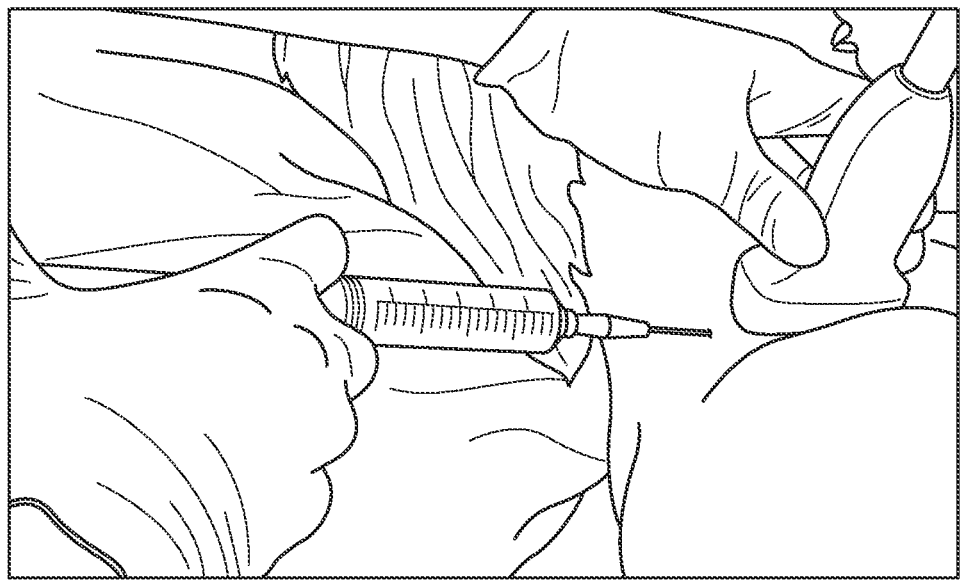
FIG. 42 illustrates an operator inserting the needle and catheter into the patient according to an example of the invention.
Figure 43:
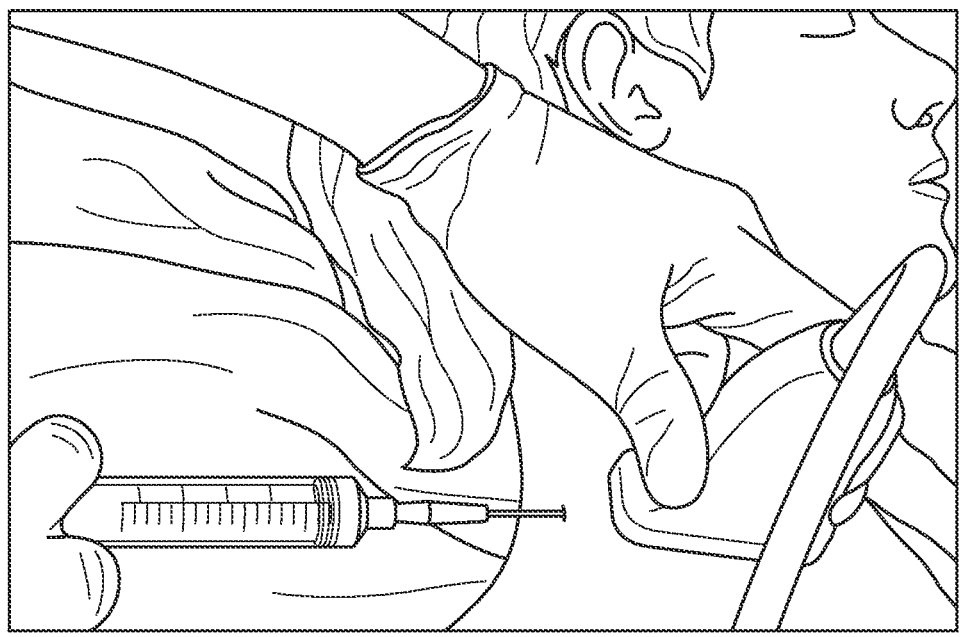
FIG. 43 illustrates an operator hydrodissecting the tissue of a patient according to an example of the invention.
Figure 44:
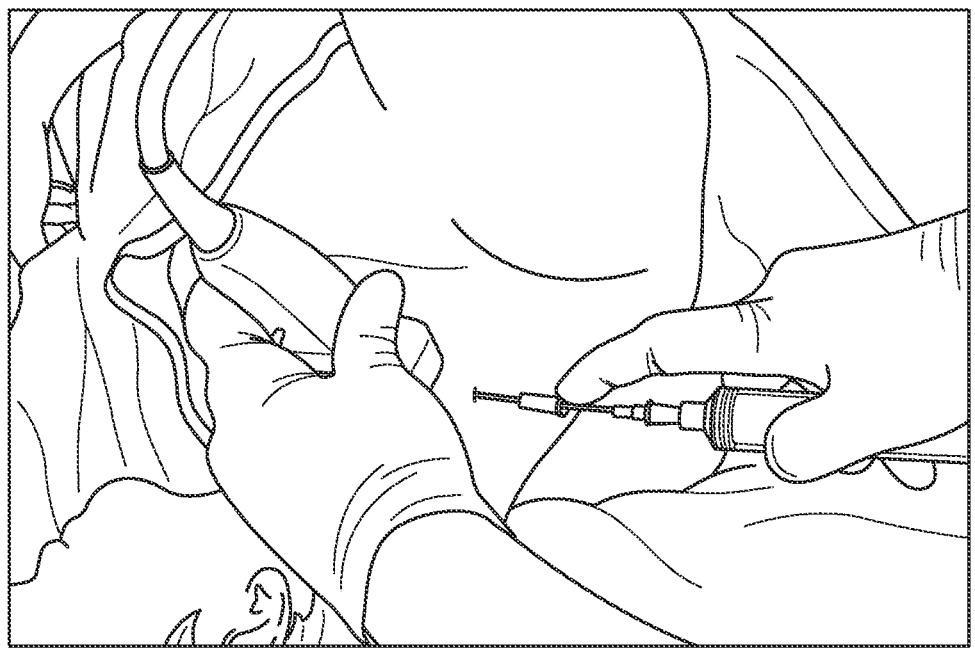
FIG. 44 illustrates the positioning of the catheter, while simultaneously imaging the patient according to an example of the invention.
Figure 45:
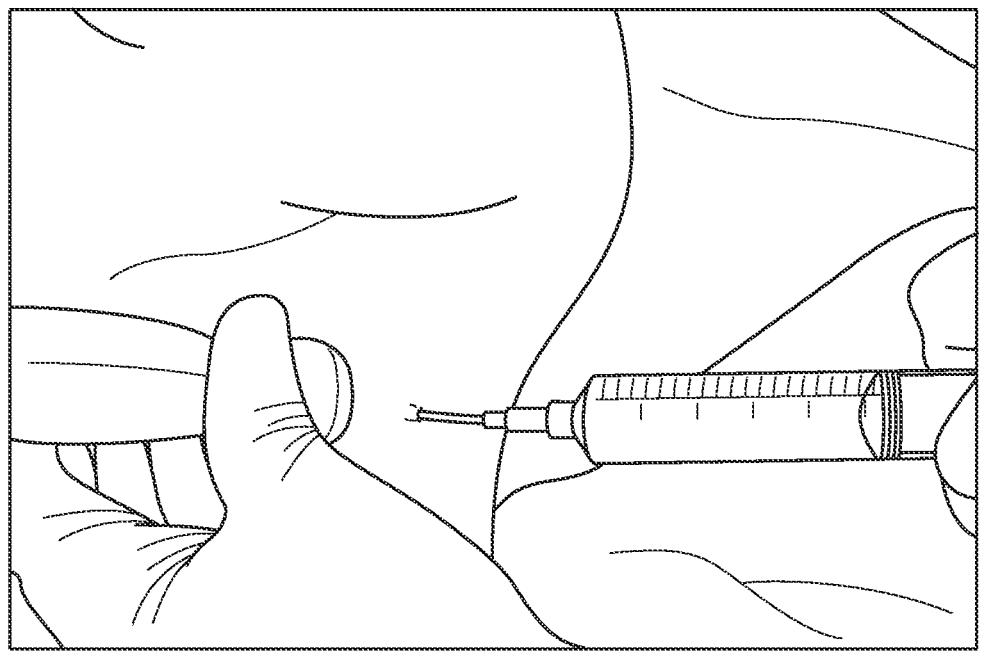
FIG. 45 illustrates injecting a pharmacological agent into a patient through the catheter according to an example of the invention.
Figure 46:
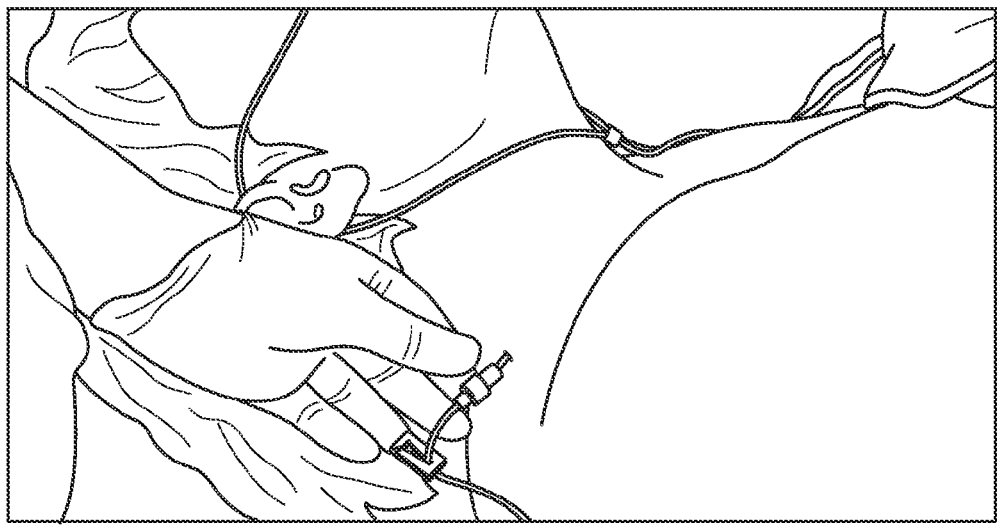
FIG. 46 illustrates attaching tubing to the catheter hub according to an example of the invention.

Step 2:

(Procedure): The operator obtained an ultrasound image of the area, and then anesthetized the skin and subcutaneous area with the 3 cc syringe filled with Lidocaine as illustrated in FIG. 41. The 1.5 inch needle attached to the 3 cc syringe extended to the nerve bundle, which was monitored using the ultrasound image. The 1.5 inch needle was withdrawn from the patient and set aside. The operator picked up the 20 cc syringe of Ropivacaine with the angiocath attached and slipped off the housing. The operator inserted the angiocath into the patent and directed the angiocath to the nerve bundle using the needle of the angiocath until the angiocath was near the nerve bundle, which was monitored using an ultrasound image as illustrated in FIG. 42. Once the operator reached the nerve bundle, the operator hydrodissected the tissue surrounding the nerve bundle using the Ropivacaine in the 20 cc syringe while monitoring the tissue surrounding the nerve bundle with an ultrasound image as illustrated in FIG. 43. The operator put their finger on the tip of the catheter hub and removed the needle while the catheter was advanced. The needle, which was connected to the syringe, was removed from the catheter with one hand, while the position of the catheter was monitored using an ultrasound image as illustrated in FIG. 44. The operator set down the empty 20 cc syringe, which was still attached to the needle, and picked up the second 20 cc syringe which contained Ropivacaine and connected the syringe to the catheter hub and injected about 20 cc of Ropivacaine into the patient through the catheter as illustrated in FIG. 45. This injection of Ropivacaine verified the catheter position and effectiveness. The operator removed and set aside the second syringe from the catheter hub and removed and set aside the ultrasound probe. The operator attached the tubing to the catheter hub as illustrated in FIG. 46.

Figure 47:
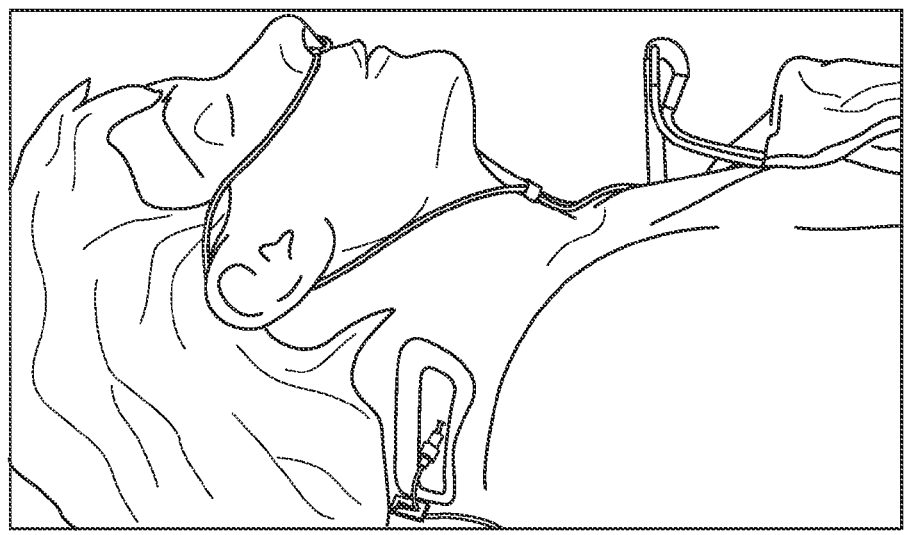
FIG. 47 illustrates the catheter being secured to the patient according to an example of the invention.

Step 3:

(Securing the Catheter): The catheter and tubing were secured to the patient with adhesive strips with the tacky substance and clear dressing was applied as illustrated in FIG. 47.

Comparative Example 2

Step 1:

(Setup): The operator opened the package that contained an Arrow StimuCath® Continuous Nerve Block Procedure Kit. The kit was double wrapped. The operator put on sterile gloves and filled the syringes. The operator set up the ultrasound probe and filled the sterile sleeve with gel. The operator placed the probe into the sterile sleeve and secured the sleeve to the ultrasound probe. The operator attached the PNS. The operator draped the patient and prepared a large area surrounding the injection site.

Step 2:

(Procedure): The operator obtained an ultrasound image of the area, and anesthetized the skin and subcutaneous. The operator inserted the needle into the patient and hydro-dissected the surrounding tissue. The operator then blindly advanced the catheter through the needle with both hands, while trying to maintain stimulation of the nerve and advance the catheter. As the needle was backed out from its position in the patient, the catheter was advanced. Once the operator believed the catheter was in place, the operator took another scan of the area with the ultrasound probe, which was put aside in order to advance the catheter. Before the operator injected a pharmacological agent through the catheter, the operator attached a connector hub to the catheter. After the hub was attached, the tubing was attached.

Step 3:

(Securing Catheter): Excess length of the catheter was coiled and the catheter was secured to the patient using adhesive strips. Clear dressing was applied to the patient.

TABLE 1

Comparison Table of Example 1 and Comparison Example 2

| Device | Terumo ® 2.5 inch 18 gauge Surflo ® I.V. Catheter | Arrow StimuCath ® Continuous Nerve Block Procedural Kit |
|---|---|---|
| Step 1 Setup: | | |
| Opening of packaging and supplies | 00:05<br>Single sterile device in package | 01:00<br>Double wrapped sterile kit |
| Gloving | 00:10<br>Non-sterile gloves | 01:00<br>Sterile gloves |
| Filling Syringes | 00:30<br>Drawing up syringes | 00:30<br>Drawing up syringes from kit |
| US Probe setup | 00:05<br>Apply non-sterile gel | 02:30<br>Fill sterile sleeve with gel<br>Place probe into sterile sleeve<br>Secure sleeve to probe |
| Attach PNS | n/a | 00:30 |
| Prep and Drape | 00:05<br>Betadine swabs - no draping | 01:00<br>Wide sterile prep with sterile draping |
| Step 2 Procedure: | | |
| Obtaining first US image | 00:30 | 00:30 |
| Anesthetize skin and SQ | 00:15 | 00:15 |
| Insertion of needle and catheter system | 00:15 | 00:15 |
| Hyrodissecting of surrounding tissue | 00:30-02:00 (variable) | 00:30-02:00 (variable) |
| Positioning catheter | 00:05<br>Catheter advanced off of needle | 01:00-10:00 (variable)<br>Blind advancement of catheter through needle with both hands<br>Trying to maintain stimulation while advancing catheter |

TABLE 1-continued

Comparison Table of Example 1 and Comparison Example 2

| Device | Terumo ® 2.5 inch 18 gauge Surflo ® I.V. Catheter | Arrow StimuCath ® Continuous Nerve Block Procedural Kit |
|---|---|---|
| Removal of needle | n/a<br>Needle withdrawn when catheter was positioned | 00:30<br>Needle is backed out while advancing catheter |
| Rescan for image | n/a<br>US image maintain at all times | 00:30<br>Need to rescan since probe was put aside to advance catheter |
| Inject through catheter | 00:30<br>Large bore with low resistance | 01:00<br>Need to attach connector hub<br>Long catheter with high resistance |
| Attach tubing to catheter | 00:15<br>Tubing connected directly to catheter hub | 00:30<br>Need to attach hub and connect tubing |
| Step 3 Securing Catheter: | | |
| Secure catheter and apply dressing | 00:15<br>Adhesive strips and clear dressing | 00:30<br>Coiling extra catheter length<br>Adhesive strips and clear dressing |
| Total time (minutes) | 03:30-05:30 | 12:00-24:00 |

Important distinctions exist between Example 1 and Example 2. Notably, Example 1 is performed by a single clinician. Example 2 requires an assistant simply due to the fact that the operator, equipment and supplies must maintain sterility with the traditional method. Furthermore, the setup and method explained in Example 2 requires that all necessary equipment and supplies are handled in a sterile fashion. If any aspect of the method is accidently contaminated, a sterile replacement for the equipment and supplies will be required, which frequently necessitates a new set up.

The steps illustrated in Example 1 are more precise and easily performed by an operator. Example 1 does not require draping or preparation of a large area on the patient, rather no draping is required and only a small portion of the patient is prepared. Furthermore, the ultrasound imager is maintained throughout the procedure in Example 1 as opposed to Example 2. The operator in Example 2 only regains the ultrasound image of the patient after the needle has been removed. Positioning the catheter as illustrated in Example 2 is highly variable with regard to time. It is rare that the catheter is in the correct position on the first attempt. More typically, the catheter and quite often the needle require repositioning which can take considerable time since real-time ultrasound imaging is not available to the operator. Furthermore, if the catheter is misplaced, then the operator may have to remove the catheter and start over with a new sterile kit.

Compared to the traditional method (Example 2), the method and device described herein using a catheter that allows for an internal introducer can result in approximately 70% to 80% savings in time. This estimate is conservative and does not take into consideration the time to reposition the catheter and needle if required, which is likely using the traditional method.

The inventions and methods described herein can be viewed as a whole, or as a number of separate inventions, that can be used independently or mixed and matched as desired. All inventions, steps, processes, devices, and methods described herein can be mixed and matched as desired. All previously described features, functions, or inventions described herein or by reference may be mixed and matched as desired.

It will be apparent to those skilled in the art that various modifications and variations can be made in the present invention without departing from the spirit or scope of the invention. For example, the cannula has a distal end that may include a sharp tip, a short beveled tip, and/or a Touhy tip. Thus, it is intended that the present invention cover all of the modifications and variations of this invention provided they come within the scope of the appended claims and their equivalents.

What is claimed is:

1. A method for administering a continuous flow or intermittent bolus of an anesthetic agent to facilitate a continuous or prolonged nerve block to a patient, comprising the steps of:

providing a cannula comprising a proximal end, a distal end comprising a curved portion, a lumen extending from the proximal end of the cannula to the distal end of the cannula, a first outside diameter, and a hub integral with the proximal end of the cannula, the hub of the cannula comprising a marker indicative of a direction of the curved portion of the cannula;

providing an over the needle catheter comprising a proximal end, a distal end, a lumen extending from the proximal end to the distal end, wherein a distal end portion of the over the needle catheter comprises a preformed region configured to move at least a portion of the over the needle catheter from a first position to a second position upon removal of the cannula in order to form a curved portion of the over the needle catheter, one or more lateral ports arranged at a location proximal to the distal end of the over the needle catheter, the lumen comprising a first inside diameter at a proximal end portion of the over the needle catheter and a second inside diameter at a distal end portion of the over the needle catheter, the first inside diameter being greater than the second inside diameter, and a hub integral with the proximal end of the over the needle catheter, the hub of the over the needle catheter comprising a marker indicative of a direction of curvature of the distal end portion of the over the needle catheter;

inserting the cannula into the lumen of the over the needle catheter such that the distal end of the cannula extends past the distal end of the over the needle catheter, wherein the first outside diameter and second inside diameter are sized to create an interference fit between the cannula and the over the needle catheter when the cannula is inserted such that a greater force is required when the first outside diameter of the cannula is adjacent to the second inside diameter of the over needle catheter;

inserting simultaneously the cannula and the over the needle catheter into the patient;

locating at least one nerve of the patient;

connecting a syringe to the hub of the cannula;

administering the anesthetic agent to the at least one nerve; and removing the cannula from the lumen of the over the needle catheter to form the curved portion of the over the needle catheter, wherein at least a portion of the curved portion of the over the needle catheter partially surrounds the at least one nerve.

2. The method of claim 1, further comprising the step of connecting an infusion pump to the hub of the over the needle catheter.

3. The method of claim 2, wherein the infusion pump is a portable infusion pump.

4. The method of claim 1, further comprising the step of coupling an electrical signal generator to a conductive element extending from the hub of the cannula.

5. The method of claim 4, further comprising the step of providing an electrical signal with the electrical signal generator.

6. The method of claim 1, wherein the marker on the hub of the catheter and the marker on the hub of the cannula comprises an arrow shape.

7. The method of claim 1, wherein the cannula comprises a tip selected from a group consisting of a sharp tip, a short beveled tip, and a Touhy tip.

8. The method of claim 1, wherein the anesthetic agent is selected from a group consisting of ropivacaine, bupivacaine, mepivacaine, lidocaine, and combinations thereof.

9. The method of claim 1, wherein the locating at least one nerve of the patient step further comprises using electrical stimulation.

10. The method of claim 9, wherein the over the needle catheter acts as an insulator when using electrical stimulation.

11. The method of claim 1, further comprising the step of aligning the marker on the hub of the catheter and the marker on the hub of the cannula.

12. The method of claim 1, wherein the at least one or more lateral ports is configured to provide the anesthetic agent.

13. The method of claim 1, wherein the curved portion of the over the needle catheter comprises a curvature relative to a longitudinal axis of the over the needle catheter in a range from about 80 degrees to about 110 degrees.

14. The method of claim 1, wherein a portion of the over the needle catheter further comprises at least one echogenic marker or radiopaque marker indicative of a location of the one or more lateral ports.

15. The method of claim 1, further comprising the step of inserting a secondary device through the lumen of the over the needle catheter.

16. A method for administering a continuous flow or intermittent bolus of an anesthetic agent to facilitate a continuous or prolonged nerve block to a patient, comprising the steps of:

providing a cannula comprising a proximal end, a distal end, a curved portion, a lumen extending from the proximal end of the cannula to the distal end of the cannula, and a hub integral with the proximal end of the cannula, the hub of the cannula comprising a marker indicative of a direction of the curved portion of the cannula, wherein the cannula is configured to provide electrical stimulation to at least one nerve of the patient;

providing an over the needle catheter comprising a proximal end, a distal end, a lumen extending from the proximal end to the distal end, one or more lateral ports arranged at a location proximal to the distal end of the over the needle catheter, and a hub integral with the proximal end of the over the needle catheter, the hub of the over the needle catheter comprising a marker indicative of an orientation of the one or more lateral ports, wherein the distal end of the over the needle catheter comprises a preformed region configured to move at least a portion of the over the needle catheter from a first position to a second position upon removal of the cannula in order to form a curved portion of the over the needle catheter;

inserting the cannula into the lumen of the over the needle catheter such that the distal end of the cannula extends past the distal end of the over the needle catheter;

aligning the marker on the hub of the over the needle catheter and the marker on the hub of the cannula;

inserting simultaneously the cannula and the over the needle catheter into the patient;

locating at least one nerve of the patient with ultrasound; and removing the cannula from the lumen of the over the needle catheter to form a curved portion of the over the needle catheter, wherein at least a portion of the curved portion of the over the needle catheter partially surrounds the at least one nerve; and administering the anesthetic agent to the at least one nerve.

17. The method of claim 16, further comprising the steps of:

coupling an electrical signal generator to a conductive element extending from the hub of the cannula; and providing an electrical signal with the electrical signal generator, wherein the electrical signal is transmitted to the distal end of the cannula.

18. The method of claim 16, wherein the over the needle catheter comprises at least one of an anti-microbial coating and an anti-bacterial coating.

19. The method of claim 16, wherein the cannula comprises at least one of an anti-microbial coating and an anti-bacterial coating.

20. The method of claim 16, wherein the curved portion of the over the needle catheter comprises a curvature relative to a longitudinal axis of the over the needle catheter in a range from about 80 degrees to about 110 degrees.

21. The method of claim 16, wherein a portion of the over the needle catheter further comprises at least one echogenic marker or radiopaque marker indicative of a location of the one or more lateral ports.

22. The method of claim 21, wherein the at least one echogenic marker or radiopaque marker comprises a first marker arranged at a proximally adjacent location to the one or more lateral ports and a second marker arranged at a distally adjacent location to the one or more lateral ports.

23. A method for administering a continuous flow or intermittent bolus of an anesthetic agent to facilitate a continuous or prolonged nerve block to a patient, comprising the steps of:

providing a cannula comprising a proximal end, a distal end, a lumen extending from the proximal end of the cannula to the distal end of the cannula, a first outside diameter, and a hub integral with the distal end of the cannula, wherein the cannula is configured to provide electrical stimulation to at least one nerve of the patient;

providing an over the needle catheter comprising a proximal end, a distal end, a lumen extending from the proximal end to the distal end, the lumen comprising a first inside diameter at a proximal end portion of the over the needle catheter and a second inside diameter at a distal end portion of the over the needle catheter, the first inside diameter being greater than the second inside diameter, and a hub integral with the proximal end of the over the needle catheter, wherein a distal end portion of the over the needle catheter comprises a preformed region configured to move at least a portion of the over the needle catheter from a first position to a second position upon removal of the cannula in order to form a curved portion of the over the needle catheter;

inserting the cannula into the lumen of the over the needle catheter such that the distal end of the cannula extends past the distal end of the over the needle catheter, wherein the first outside diameter and the second inside diameter are sized to create an interference fit between the cannula and the over the needle catheter when the cannula is inserted such that a greater force is required when the first outside diameter of the cannula is adjacent to the second inside diameter of the over the needle catheter;

inserting simultaneously the cannula and the over the needle catheter into the patient;

locating at least one nerve of the patient with at least one of: i. an electric signal generated from an electrical signal generator provided to the cannula, ii. an ultrasound, or iii. both;

administering the anesthetic agent to the at least one nerve; and removing the cannula from the lumen of the over the needle catheter to form the curved portion of the over the needle catheter, wherein at least a portion of the curved portion of the over the needle catheter partially surrounds the at least one nerve.

24. The method of claim 23, wherein the over the needle catheter comprises a reinforced material.

25. The method of claim 23, wherein the step of locating at least one nerve of the patient with at least one of: i. an electric signal generated from an electrical signal generator provided to the cannula comprises the step of coupling the electrical signal generator to a conductive element extending from the hub of cannula; and providing the electrical signal with the electrical signal generator.

26. The method of claim 23, further comprising the step of inserting a secondary device through the lumen of the over the needle catheter.

27. The method of claim 23, wherein a portion of the over the needle catheter comprises a plurality of markers indicative of length of the over the needle catheter.

28. The method of claim 23, wherein the one or more lateral ports comprises three or more lateral ports radially spaced around a circumference of the distal end portion of the over the needle catheter.

29. The method of claim 23, wherein a portion of the over the needle catheter further comprises at least one echogenic marker or radiopaque marker indicative of the distal end of the over the needle catheter.

\* \* \* \* \*

UNITED STATES PATENT AND TRADEMARK OFFICE
CERTIFICATE OF CORRECTION

Page 1 of 1

PATENT NO.        : 8,986,283 B2
APPLICATION NO.   : 14/035940
DATED             : March 24, 2015
INVENTOR(S)       : Sundar Rajendran, Dan Joel Kopacz and Siddharth Desai It is certified that error appears in the above-identified patent and that said Letters Patent is hereby corrected as shown below:

In the Claims

Claim 23, column 52, line 67, replace "the distal end" with --the proximal end--.

Signed and Sealed this
Twenty-sixth Day of January, 2016

Michelle K. Lee
*Director of the United States Patent and Trademark Office*